(12) United States Patent
Selby

(10) Patent No.: US 7,326,704 B2
(45) Date of Patent: Feb. 5, 2008

(54) IMINOBENZOXAZINES, IMINOBENZTHIAZINES AND IMINOQUINAZOLINES FOR CONTROLLING INVERTEBRATE PESTS

(75) Inventor: Thomas Paul Selby, Hockessin, DE (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/490,898

(22) Filed: Jul. 21, 2006

(65) Prior Publication Data

US 2006/0258649 A1   Nov. 16, 2006

Related U.S. Application Data

(62) Division of application No. 10/488,233, filed as application No. PCT/US02/32845 on Oct. 15, 2002, now Pat. No. 7,148,217.

(60) Provisional application No. 60/329,392, filed on Oct. 15, 2001.

(51) Int. Cl.
*A61K 31/536* (2006.01)
(52) U.S. Cl. ..................... 514/230.5; 544/90
(58) Field of Classification Search .............. 514/230.5
See application file for complete search history.

(56) References Cited

U.S. PATENT DOCUMENTS

| 4,321,371 A | 3/1982 | Parg et al. |
| 5,602,126 A | 2/1997 | Barnette et al. |
| 5,728,693 A | 3/1998 | Stevenson |

FOREIGN PATENT DOCUMENTS

| DE | 4428380 A | 8/1994 |
| DE | 19840322 A1 | 9/1998 |
| EP | 0919542 A2 | 6/1999 |
| EP | 1193254 A1 | 1/2001 |
| NL | 9202078 A | 11/1992 |
| WO | WO 96/38419 | 12/1996 |
| WO | WO 00/31082 A | 6/2000 |
| WO | WO 00/63427 | 10/2000 |
| WO | WO 01/02354 A1 | 1/2001 |
| WO | WO 01/32628 A1 | 5/2001 |
| WO | WO 01/70671 A2 | 9/2001 |

OTHER PUBLICATIONS

XP002177117 Suto, Mark J. et al.: Tetrahedron Letters, vol. 36, No. 40, 1995, pp. 7219-7216, Elsevier Science Publishers, Amsterdam, NL.

Klaubert et al., J.Med.Chem., vol. 24, No. 6. pp. 748-52, 1981.
XP004254109 Fabia et al, An expedient route to aromatic pyrrolo[2,1-c][1,4]benzodiazepines and a study of their reactivity, Tetrahedron Letters (2001), 42(31), 5183-5189.
Mazurklewicz, Roman; Synthesis and rearrangement of 4-imino-4H-3,1-benzoxazines, Monatshefte fuer Chemie 120, 973-980 (1989).
A.S.S. Salman, New heteroxyclic synthesis from cyanopyridine derivates retrieved from STN, Communications De La Faculte Des Sciences De L'Universite D'Ankara, Serio (1998), 44(1-2), 57-66.
Louis Legrand et al., Heterocyclic Sulfur Compounds-LXXXV. Steric Effects In the Reaction of Primary Amines upon 3,1-Benzothiazine-4-thiones, Phosphorus and Sulfur 1978, vol. 5, pp. 209-215.
Jiri Hanusek et al, Synthesis of Substituted 2-Benzoylamino-thiobanzamides and Their Ring Closure to Substituted 2-Phenyl-quinazoline-4-thiones, Molecules 2001, 6, 323-337.

*Primary Examiner*—Kahsay Habte

(57) ABSTRACT

This invention pertains to methods for controlling invertebrate pests comprising contacting the invertebrate pest or its environment with a biologically effective amount of a compound of Formula I

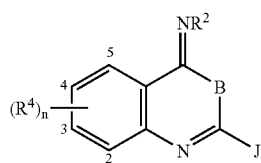

wherein
B is O, S or $NR^1$;
J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$; and
$R^1$, $R^2$, $R^4$, $R^5$ and n are as defined in the disclosure.

This invention also pertains to certain compounds of Formula I and compositions for controlling invertebrate pests comprising a biologically effective amount of a compound of Formula I and at least one additional component selected from the group consisting of surfactants, solid diluents and liquid diluents and optionally further comprising an effective amount of at least one additional biologically active compound or agent.

13 Claims, No Drawings

IMINOBENZOXAZINES, IMINOBENZTHIAZINES AND IMINOQUINAZOLINES FOR CONTROLLING INVERTEBRATE PESTS

CROSS-REFERENCE TO RELATED APPLICATIONS

This is a Division of U.S. application Ser. No. 10/488,233, filed Feb. 26, 2004, now U.S. Pat. No. 7,148,217, which is a National Stage of WO application number PCTUS02/32845, filed Oct. 15, 2002 which claims benefit of U.S. provisional application No. 60/329,392, filed Oct. 15, 2001.

BACKGROUND OF THE INVENTION

This invention relates to certain iminobenzoxazines, iminobenzthiazines and iminoquinazolines, their N-oxides, salts and compositions suitable for agronomic and nonagronomic uses, including those uses listed below, and a method of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides

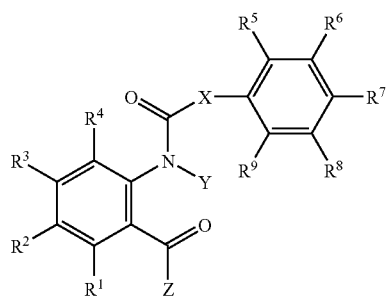

wherein, inter alia, X is a direct bond; Y is H or $C_1$-$C_6$ alkyl; Z is $NH_2$, $NH(C_1$-$C_3$ alkyl) or $N(C_1$-$C_3$ alkyl)$_2$; and $R^1$ through $R^9$ are independently H, halogen, $C_1$-$C_6$ alkyl, phenyl, hydroxy, $C_1$-$C_6$ alkoxy or $C_1$-$C_7$ acyloxy.

WO 00/31082 discloses pyrimidin-4-enamines of Formula ii as fungicides

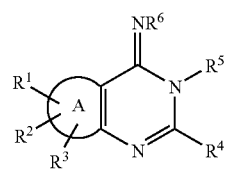

wherein, inter alia, A is a fused benzene ring; $R^1$, $R^2$ and $R^3$ are H, halogen, optionally substituted alkyl, alkenyl or alkynyl; $R^4$ is optionally substituted phenyl; $R^5$ is optionally substituted alkyl, alkenyl or alkynyl; and $R^6$ is H or optionally substituted alkyl, alkenyl or alkynyl.

SUMMARY OF THE INVENTION

This invention pertains to a method for controlling an invertebrate pest comprising contacting the invertebrate pest or its environment with a biologically effective amount of a compound of Formula I, its N-oxide or an agriculturally suitable salt of the compound (e.g., as a composition described herein)

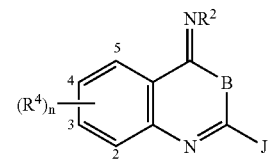

wherein
B is O, S or $NR^1$;
J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$;
$R^1$ is K;
each K is independently G; $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of halogen, G, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, and a phenyl, phenoxy or 5- or 6-membered heteroaromatic ring, each ring optionally substituted with one to three substituents independently selected from $R^6$; hydroxy; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl and $C_2$-$C_6$ alkylcarbonyl;
$R^2$ is H or K; or
$R^1$ and $R^2$ are taken together to form a linking chain of 2 to 5 members including at least one carbon member, optionally including no more than two carbon members as C(=O), and optionally one member selected from nitrogen and oxygen, optionally substituted with 1 to 4 substituents selected from $R^3$;
each $R^3$ is independently $C_1$-$C_4$ alkyl, halogen, CN, $NO_2$ or $C_1$-$C_2$ alkoxy;
G is a 5- or 6-membered nonaromatic carbocyclic or heterocyclic ring, optionally including one or two ring members selected from the group consisting of C(=O), SO and $S(O)_2$ and optionally substituted with from 1 to 4 substituents selected from $R^3$;
each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_5$ alkoxyalkyl, $C_1$-$C_4$ hydroxyalkyl, $C(O)R^{10}$, $CO_2R^{10}$, $C(O)NR^{10}R^{11}$, $NR^{10}R^{11}$, $N(R^{11})CO_2R^{10}$ or $C_3$-$C_6$ trialkylsilyl; or each $R^4$ is independently a phenyl, benzyl, phenoxy or a 5- or 6-membered heteroaromatic ring, each ring optionally substituted with from one to three substituents independently selected from $R^6$;

each $R^5$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring or ring system optionally substituted with from one to three substituents independently selected from $R^6$; or two $R^5$ groups when attached to adjacent carbon atoms are taken together as —$OCF_2O$—, —$CF_2CF_2O$—, or —$OCF_2CF_2O$—;

each $R^6$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_8$ alkyl(cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{10}$ is H, $C_1$-$C_4$ alkyl or $C_1$-$C_4$ haloalkyl;

$R^{11}$ is H or $C_1$-$C_4$ alkyl; and n is an integer from 1 to 4.

This invention also relates to such a method wherein the invertebrate pest or its environment is contacted with a biologically effective amount of a compound of Formula I or a composition comprising a compound of Formula I and a biologically effective amount of at least one additional compound or agent for controlling invertebrate pests.

This invention also pertains to a compound of Formula Is, N-oxides or salts thereof

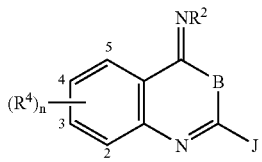

Is wherein

B is or S;

J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$;

$R^2$ is H; G; $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of halogen, G, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, and a phenyl, phenoxy or 5- or 6-membered heteroaromatic ring, each ring optionally substituted with one to three substituents independently selected from $R^6$; hydroxy; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl and $C_2$-$C_6$ alkylcarbonyl;

G is a 5- or 6-membered nonaromatic carbocyclic or heterocyclic ring, optionally including one or two ring members selected from the group consisting of $C(=O)$, SO and $S(O)_2$ and optionally substituted with 1 to 4 substituents selected from $R^3$;

each $R^3$ is independently $C_1$-$C_2$ alkyl, halogen, CN, $NO_2$ or $C_1$-$C_2$ alkoxy;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_5$ alkoxyalkyl $C_1$-$C_4$ hydroxyalkyl, $C(O)R^{10}$, $CO_2R^{10}$, $C(O)NR^{10}R^{11}$, $NR^{10}R^{11}$, $N(R^{11})CO_2R^{10}$ or $C_3$-$C_6$ trialkylsilyl; or each $R^4$ is independently a phenyl, benzyl, phenoxy or a 5- or 6-membered heteroaromatic ring, each ring optionally substituted with one to three substituents independently selected from $R^6$;

each $R^5$ is independently $C_1$-$C_6$ alkyl, $C_2$-$C_6$ alkenyl, $C_2$-$C_6$ alkynyl $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl $C_3$-$C_8$ dialkylaminocarbonyl or $C_3$-$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring optionally substituted with from one to three substituents independently selected from $R^6$; or two $R^5$ groups when attached to adjacent carbon atoms are taken together as —$OCF_2O$—, —$CF_2CF_2O$—, or —$OCF_2CF_2O$—;

each $R^6$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_8$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{10}$ is H, $C_1$-$C_4$ alkyl or $C_1$-$C_4$ haloalkyl;

$R^{11}$ is H or $C_1$-$C_4$ alkyl; and n is an integer from 1 to 4.

This invention also pertains to a composition for controlling an invertebrate pest comprising a biologically effective amount of a compound of Formula I and at least one additional component selected from the group consisting of surfactants, solid diluents and liquid diluents. This invention also pertains to such compositions optionally further comprising an effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl. "Trialkylsilyl" includes $(CH_3)_3Si$, $(CH_3CH_2)_3Si$ and $[(CH_3)_3C](CH_3)_2Si$. "(Alkyl)cycloalkylamino" means a cycloalkylamino group where the hydrogen atom is replaced by an alkyl radical; examples include groups such as (methyl)cyclopropylamino, (ethyl)cyclobutylamino, (iso-propyl)cyclopentylamino and (methyl)cyclohexylamino. As indicated in the Summary of the Invention, the cycloalkyl in cycloalkylamino and (alkyl)cycloalkylamino is $C_3$-$C_6$ cycloalkyl, while the alkyl in (alkyl)cycloalkylamino is $C_1$-$C_4$ alkyl.

The term "aromatic" indicates that each of the ring atoms is essentially in the same plane and has a p-orbital perpendicular to the ring plane, and in which (4n+2) π electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. Aromatic carbocyclic ring or fused carbobicyclic ring systems includes fully aromatic carbocycles and carbocycles in which at least one ring of a polycyclic ring system is aromatic (e.g. phenyl and naphthyl). The term "nonaromatic carbocyclic ring" denotes fully saturated carbocycles as well as partially or fully unsaturated carbocycles where the Hückel rule is not satisfied by the ring. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH_3)C(=O)$.

The total number of carbon atoms in a substituent group is indicated by the "$C_i$-$C_j$" prefix where i and j are numbers from 1 to 8. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I comprises a heterocyclic ring, all substituents are attached to this ring through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted" indicates that a moiety may be substituted or unsubstituted. The term "optionally substituted with from one to three substituents" and the like indicates that the moiety may be unsubstituted or from one to three of the available positions on the moiety may be substituted. When a moiety contains a substituent which can be hydrogen, for example $R^4$, then, when this substituent is taken as hydrogen, it is recognized that this is equivalent to said moiety being unsubstituted.

Compounds of Formula I can exist as one or more stereoisomers. The various stereoisomers include enantiomers, diastereomers, atropisomers and geometric isomers. Of note are geometric isomers in which $R^2$ of the imino moiety may be syn or anti relative to B, or a mixture of syn and anti geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of Formula I may be present as a mixture of stereoisomers, individual stereoisomers, or as an optically active form. Some compounds of Formula I can exist as one or more tautomers, and all tautomeric forms of such compounds are part of the present invention. Accordingly, the compounds of the invention may be present as a mixture of tautomers or the individual tautomers.

The present invention comprises compounds selected from Formula I, N-oxides and salts thereof. One skilled in the art will appreciate that not all nitrogen containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, Vol. 3, pp 18-19, A. J. Boulton and A. McKillop, Eds., Pergamon Press; M. R. Grimmett and B. R. T. Keene in *Advances in Heterocyclic Chemistry*, Vol. 43, pp 139-151, A. R. Katritzky, Ed., Academic Press; M. Tisler and B. Stanaovnik in *Advances in Heterocyclic Chemistry*, Vol. 9, pp 285-291, A. R. Katritzky and A. J. Boulton, Eds., Academic Press; and G. W. H. Cheeseman and E. S. G. Werstiuk in *Advances in Heterocyclic Chemistry*, Vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic moiety such as a carboxylic acid or phenol.

As noted above, J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$. The term "optionally substituted" in connection with these J groups refers to groups which are unsubstituted or have at least one non-hydrogen substituent that does not extinguish the biological activity possessed by the unsubstituted analog. An example of phenyl optionally substituted with 1 to 4 $R^5$ is the ring illustrated as U-1 in Exhibit 1, wherein $R^v$ is $R^5$ and r is an integer from 0 to 4. An example of a naphthyl group optionally substituted with 1 to 4 $R^5$ is illustrated as U-85 in Exhibit 1, wherein $R^v$ is $R^5$ and r is an integer from 0 to 4. Examples of 5- or 6-membered heteroaromatic rings optionally substituted with 1 to 4 $R^5$ include the rings U-2 through U-53 illustrated in Exhibit 1 wherein $R^v$ is $R^5$ and r is an integer from 0 to 4. Note that J-1 through J-5 below also denote 5- or 6-membered heteroaromatic rings. Note that U-2 through U-20 are examples of J-1, U-21 through U-35 and U-40 are examples of J-2, U-36 through U-39 are examples of J-3, U-41 through U-48 are examples of J-4 and U-49 through U-53 are examples of J-5. Examples of aromatic 8-, 9- or 10-membered fused heterobicyclic ring systems optionally substituted with 1 to 4 $R^5$ include U-54 through U-84 illustrated in Exhibit 1 wherein $R^v$ is $R^5$ and r is an integer from 0 to 4.

The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon atom of the U group. Note that when the attachment point on the U group is illustrated as floating, the U group can be attached to the remainder of Formula I through any available carbon of the U group by replacement of a hydrogen atom.

Exhibit 1

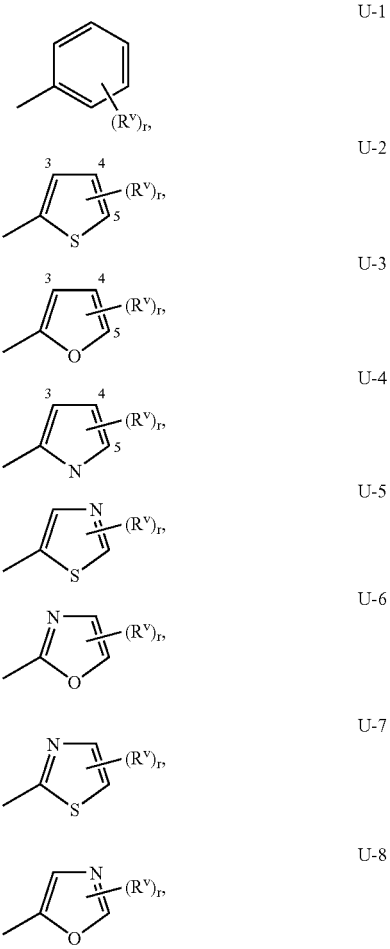

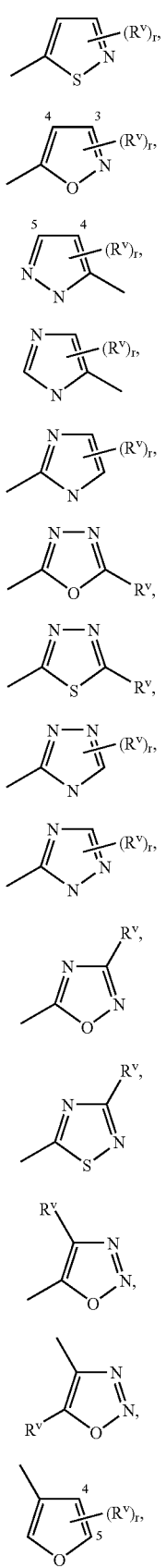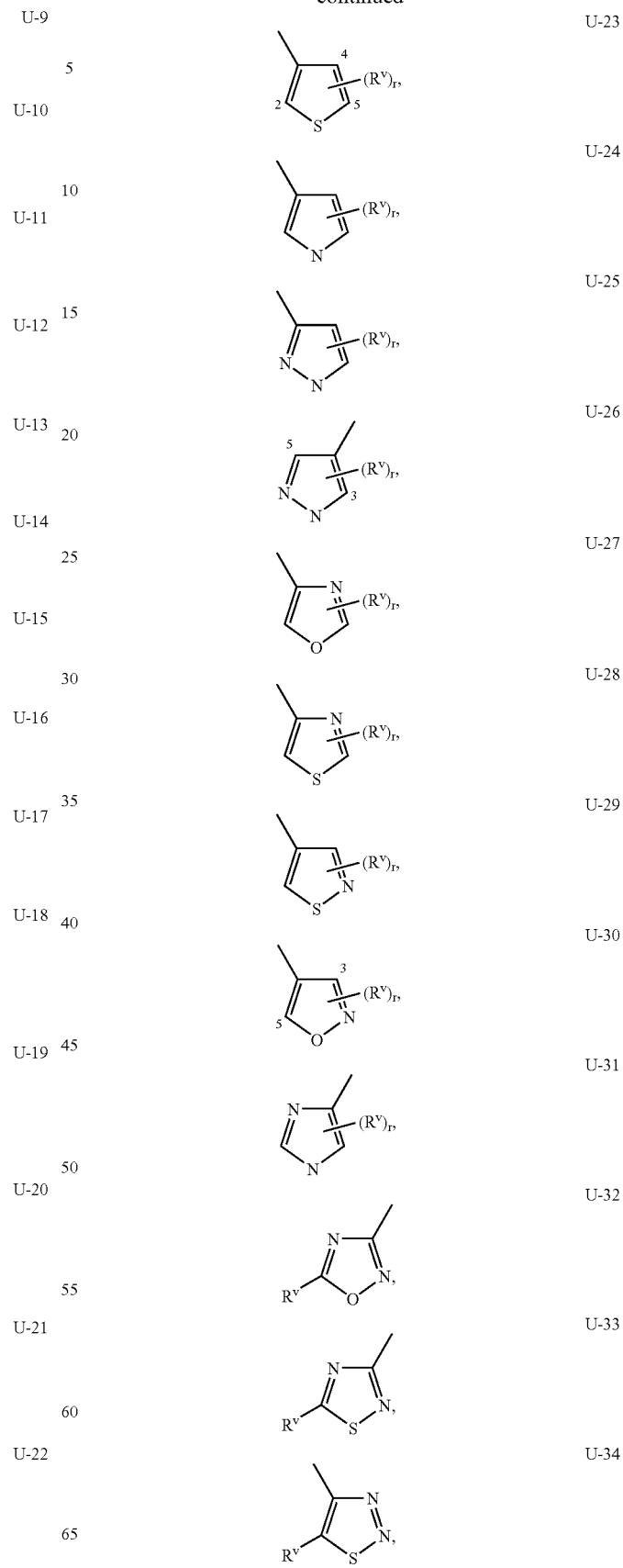

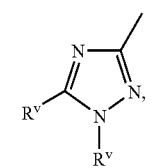
U-35
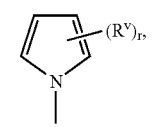
U-36
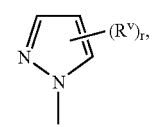
U-37
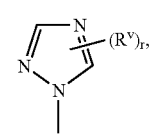
U-38
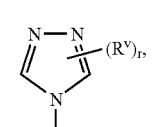
U-39
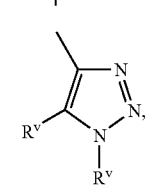
U-40
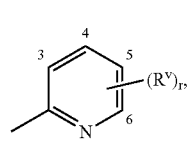
U-41
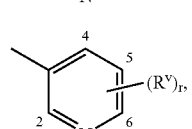
U-42
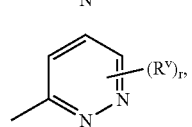
U-43
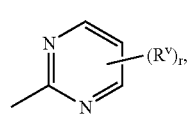
U-44
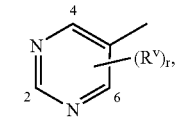
U-45
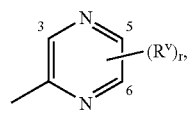
U-46
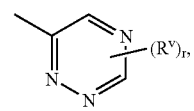
U-47
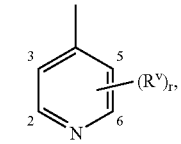
U-48
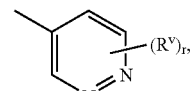
U-49
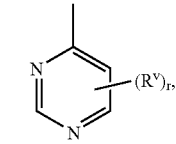
U-50
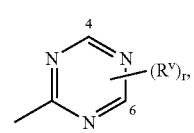
U-51
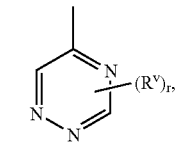
U-52
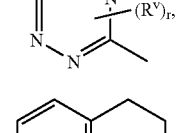
U-53
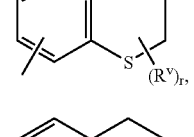
U-54
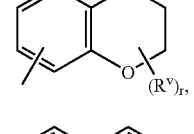
U-55
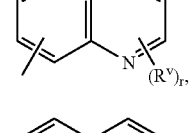
U-56
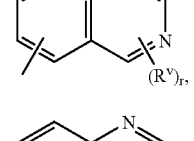
U-57
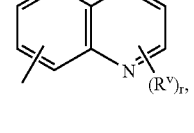
U-58

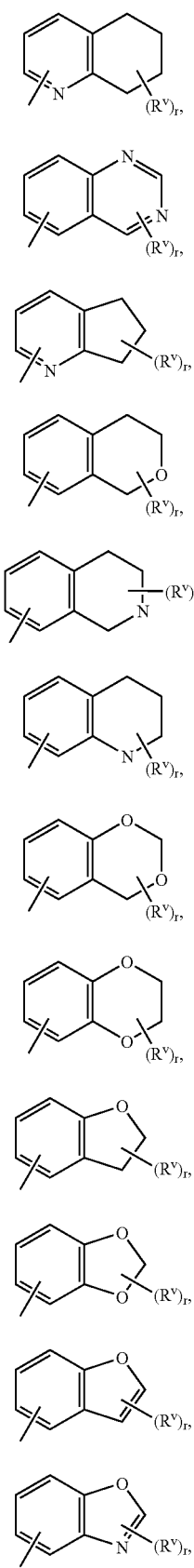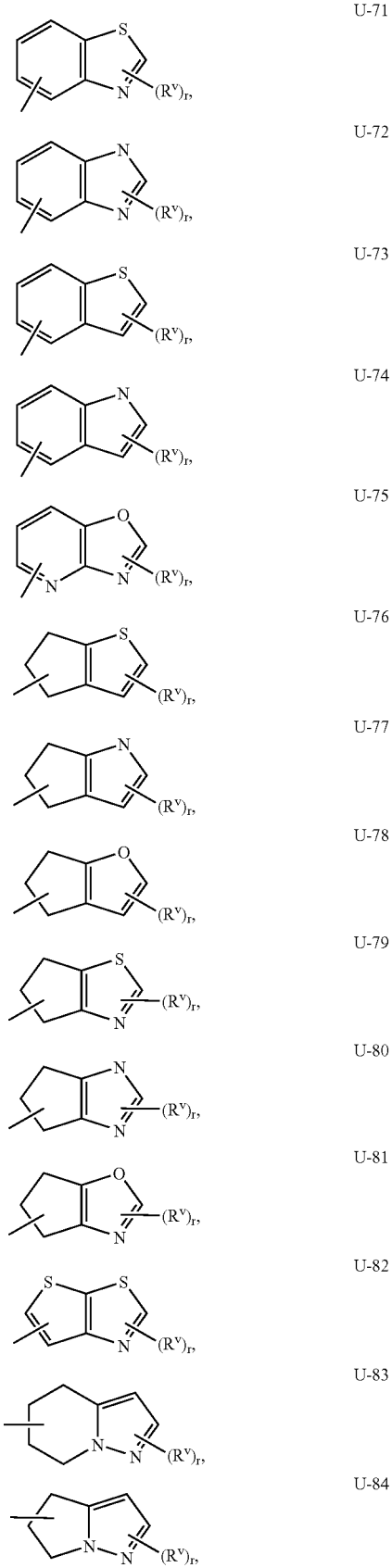

-continued

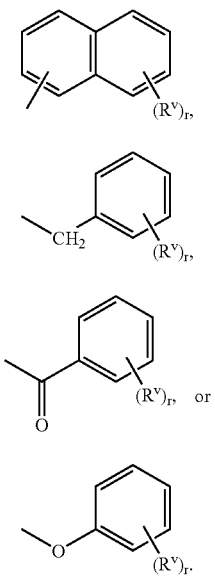

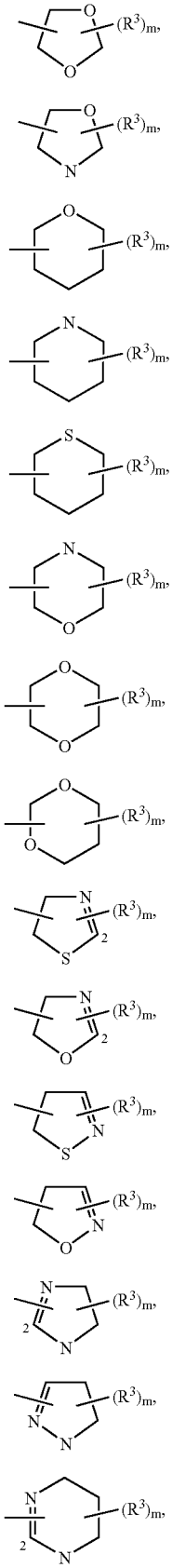

As noted above G is a 5- or 6-membered nonaromatic carbocyclic or heterocyclic ring, optionally including one or two ring members selected from the group consisting of C(=O), SO and S(O)$_2$ and optionally substituted with 1 to 4 substituents selected from R$^3$. Examples of such G groups include those illustrated as G-1 through G-41 in Exhibit 2 wherein m is an integer from 0 to 4. The term "optionally substituted" in connection with these G groups refers to groups which are unsubstituted or have at least one non-hydrogen substituent that does not extinguish the biological activity possessed by the unsubstituted analog. Note that when the attachment point on these G groups is illustrated as floating, the G group can be attached to the remainder of Formula I through any available carbon or nitrogen of the G group by replacement of a hydrogen atom. The optional substituents can be attached to any available carbon or nitrogen by replacing a hydrogen atom. Note that when G comprises a ring selected from G-24 through G-29 and G-32 through G-35, A is selected from O, S or NR$^3$. Note that when G is G-3, G-5, G-7, G-9, G-16 through G-18, G-23, and G-24 through G-29, and G-32 through G-35 (when A is NR$^3$), the nitrogen atoms that require substitution to fill their valence are substituted with H or R$^3$.

Exhibit 2

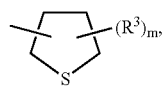

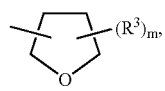

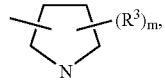

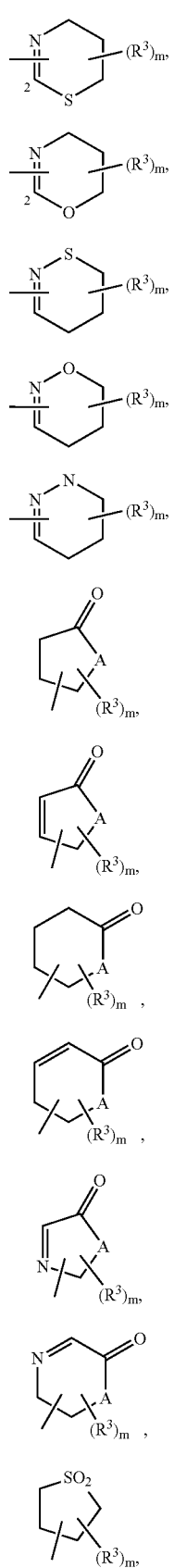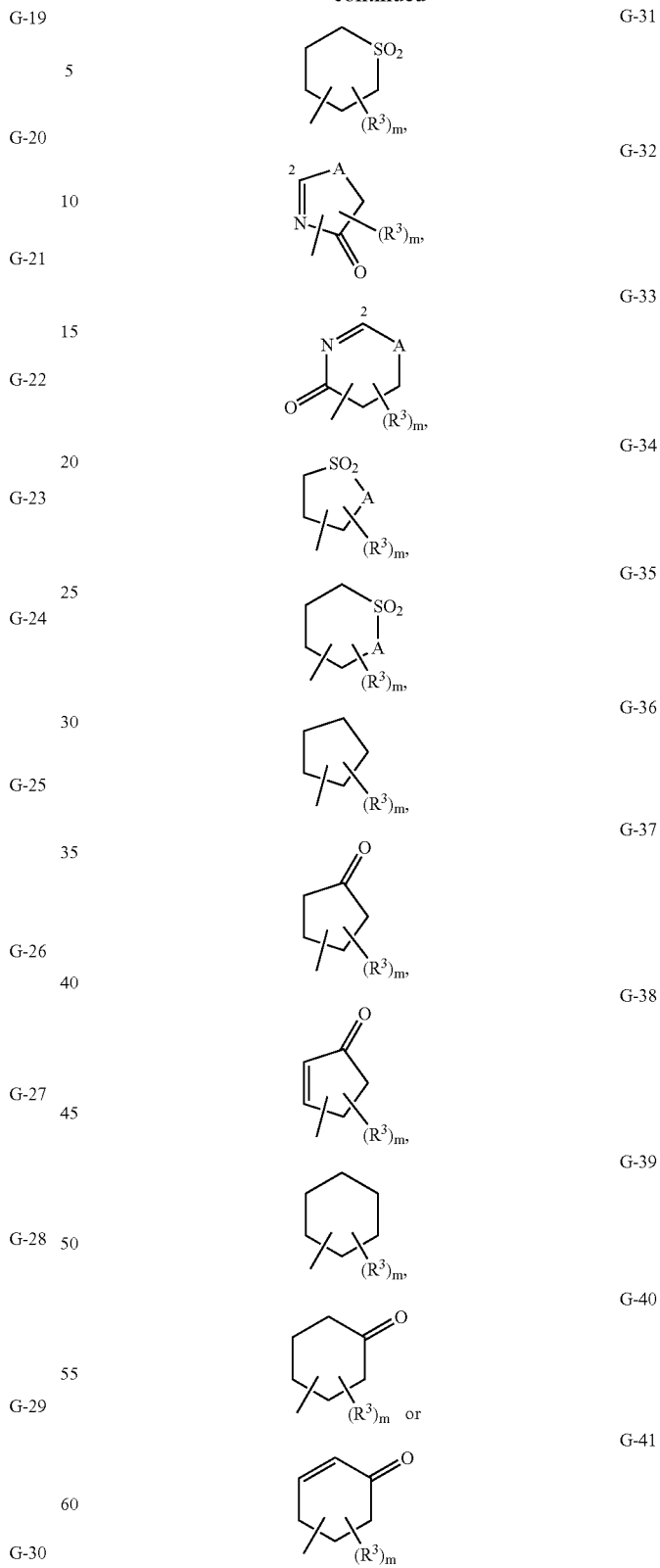
As noted above, certain $R^1$ and $R^2$ groups can be optionally substituted with one or more substituents. The term "optionally substituted" in connection with these groups refers to R¹ and/or R² groups that are unsubstituted or have at least one non-hydrogen substituent. Examples of optionally substituted R¹ and/or R² groups are those that are optionally substituted by replacement of a hydrogen on a carbon atom of the R¹ and/or R² group with one or more (up to the total number of hydrogens available for replacement in any specific R¹ and/or R² group) substituents independently selected from the substituents listed in the Summary of the Invention above. Although these substituents are listed, it is noted that they do not need to be present since they are optional substituents. Of note are R¹ and/or R² groups that are unsubstituted. Of note are R¹ and/or R² groups substituted with one to five substituents. Also of note are R¹ and/or R² groups substituted with one substituent.

As noted above, each R¹ and R² can be independently (among others) $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from (among others) a phenyl, phenoxy or 5- or 6-membered heteroaromatic ring, each ring optionally substituted with one to three substituents independently selected from $R^6$. The term "optionally substituted" in connection with these groups refers to groups which are unsubstituted or have at least one non-hydrogen substituent that does not extinguish the biological activity possessed by the unsubstituted analog. Examples of such substituents include the rings illustrated as U-1 through U-53 and U-88 illustrated in Exhibit 1, except that such rings are optionally substituted with 1 to 3 substituents independently selected from $R^6$ rather than $(R^v)_r$. Note that $R^6$ substituents do not need to be present since they are optional substituents.

As noted above, each $R^4$ is independently (among others) a phenyl, benzyl, phenoxy or a 5- or 6-membered heteroaromatic ring, each ring optionally substituted with one to three substituents independently selected from $R^6$. The term "optionally substituted" in connection with these $R^4$ groups refers to groups which are unsubstituted or have at least one non-hydrogen substituent that does not extinguish the biological activity possessed by the unsubstituted analog. Examples of such $R^4$ groups include the rings illustrated as U-1 through U-53, U-86 and U-88 illustrated in Exhibit 1, except that such rings are optionally substituted with 1 to 3 substituents independently selected from $R^6$ rather than $(R^v)_r$. Note that $R^6$ substituents do not need to be present since they are optional substituents.

As noted above, each $R^5$ is independently (among others) a phenyl, benzyl, benzoyl, phenoxy, 5- or 6-membered heteroaromatic ring or an aromatic 8-, 9- or 10-membered fused heterobicyclic ring system, each ring or ring system optionally substituted with one to three substituents independently selected from $R^6$. Examples of such $R^5$ groups include the rings and ring systems illustrated as U-1 through U-88 illustrated in Exhibit 1, except that such rings and ring systems are optionally substituted with 1 to 3 substituents independently selected from $R^6$ rather than $(R^v)_r$. Note that $R^6$ substituents do not need to be present since they are optional substituents.

Preferred for reasons of cost, ease of synthesis or application, and/or biological efficacy are:

Preferred 1. Methods comprising compounds of Formula I wherein
  $R^2$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, CN, $C_1$-$C_2$ alkoxy, $C_1$-$C_2$ alkylthio, $C_1$-$C_2$ alkylsulfinyl and $C_1$-$C_2$ alkylsulfonyl;

one $R^4$ group is attached to the phenyl ring at the 2-position or 5-position, and said $R^4$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl; and
  n is 1 or 2.

Preferred 2. Methods of Preferred 1 wherein J is a phenyl group optionally substituted with 1 to 4 $R^5$.

Preferred 3. Methods of Preferred 2 wherein
  B is O; and
  each $R^5$ is independently halogen, $C_1$-$C_4$ alkyl, $C_1$-$C_2$ alkoxy, $C_1$-$C_4$ haloalkyl, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or
  each $R^5$ is independently a phenyl or a 5- or 6-membered heteroaromatic ring, each ring optionally substituted with one to three substituents independently selected from $R^6$; or
  two $R^5$ groups when attached to adjacent carbon atoms are taken together as —$OCF_2O$—, —$F_2CF_2O$—, or $CF_2CF_2O$—.

Preferred 4. Methods of Preferred 3 wherein
  $R^2$ is $C_1$-$C_4$ alkyl optionally substituted with halogen, CN, $OCH_3$ or $S(O)_pCH_3$;
  one $R^4$ group is attached to the phenyl ring at the 2-position and said $R^4$ is $CCH_3$, $CF_3$, $OCF_3$, $OCHF_2$, $S(O)_pCF_3$, $S(O)_pCHF_2$, CN or halogen;
  a second $R^4$ is H, F, Cl, Br, I, CN or $CF_3$;
  each $R^5$ is independently halogen, methyl, $CF_3$, $OCF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$; or a phenyl, pyrazole, imidazole, triazole, pyridine or pyrimidine ring, each ring optionally substituted with one to three substituents independently selected from $C_1$-$C_4$ alkyl, $C_1$-$C_4$ haloalkyl, halogen and CN; and
  p is 0, 1 or 2.

Preferred 5. Methods of Preferred 4 wherein $R^2$ is H, Me, Et, i-propyl or t-butyl.

Preferred 6. Methods of Preferred 1 wherein
  J is a 5- or 6-membered heteroaromatic ring selected from the group consisting of J-1, J-2, J-3, J-4 and J-5, each J optionally substituted with 1 to 3 $R^5$

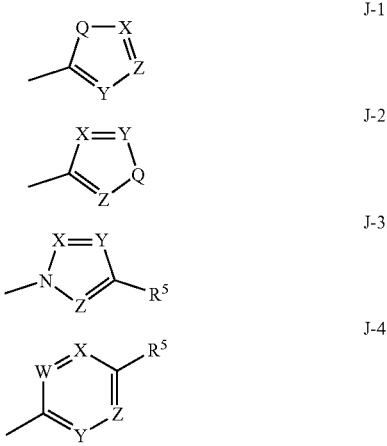

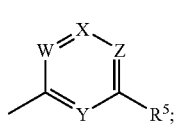
J-5

Q is O, S, NH o NR⁵; and
W, X, Y and Z are independently N, CH or CR⁵, provided that in J-4 and J-5 at least one of W, X, Y or Z is N.

Preferred 7. Methods of Preferred 6 wherein
B is O; and
each $R^5$ is independently $C_1$-$C_4$ alkyl, $C_1$-$C_4$ haloalkyl, halogen, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or a phenyl or a 5- or 6-membered heteroaromatic ring, each ring optionally substituted with one to three substituents independently selected from $R^6$.

Preferred 8. Methods of Preferred 7 wherein
J substituted with 1 to 3 $R^5$ is selected from the group consisting of J-6, J-7, J-8, J-9, J-10, J-11, J-12 and J-13

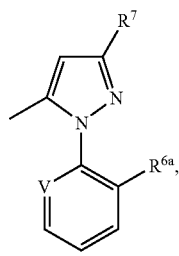
J-6

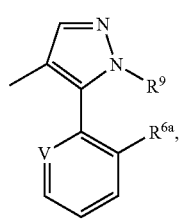
J-7

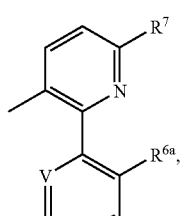
J-8

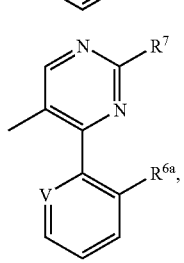
J-9

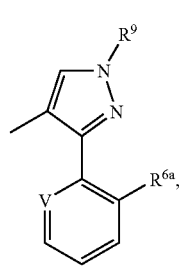
J-10

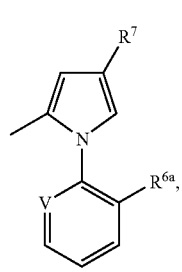
J-11

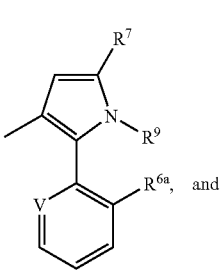
J-12, and

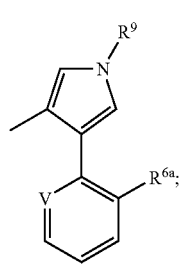
J-13

V is N, CH, CF, CCl, CBr or CI;
each $R^{6a}$ is independently H or $R^6$;
$R^6$ is $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ haloalkoxy or $C_1$-$C_4$ haloalkylthio;
each $R^7$ is independently $C_1$-$C_6$ alkyl, $C_1$-$C_6$ haloalkyl, halogen, CN, $C_1$-$C_4$ alkoxy, $C_1$-$C_4$ haloalkoxy or $C_1$-$C_4$ haloalkylthio;
$R^9$ is $C_2$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl;
$R^{10}$ is $C_1$-$C_4$ alkyl or $C_1$-$C_4$ haloalkyl;
$R^{11}$ is $C_1$-$C_4$ alkyl; and
n is 1 or 2.

Note that $R^7$ and $R^9$ are subsets of $R^5$. Note that the F, Cl, Br or I atoms encompassed within V are a subset of $R^6$. Of note are methods of Preferred 8 wherein V is N. Also of note are methods of Preferred 8 wherein V is CH, CF, CCl or CBr. Of particular note are methods of Preferred 8 wherein V is N or CH.

Preferred 9. Methods of Preferred 8 wherein
$R^2$ is $C_1$-$C_4$ alkyl optionally substituted with halogen, CN, $OCH_3$ or $S(O)_pCH_3$; or $CH_2C\equiv CH$;

one $R^4$ group is attached to the phenyl ring at the 2-position and said $R^4$ is $CH_3$, $CF_3$, $OCF_3$, $OCHF_2$, $S(O)_pCF_3$, $S(O)_pCHF_2$, CN or halogen;

a second $R^4$ is H, F, Cl, Br, I, CN or $CF_3$;

$R^{6a}$ is H, $C_1$-$C_4$ alkyl, $C_1$-$C_4$ haloalkyl, halogen or CN;

$R^7$ is $CH_3$, $CF_3$, $OCH_2CF_3$, $OCHF_2$ or halogen;

$R^9$ is $CH_2CF_3$, $CHF_2$ or $CF_3$; and p is 0, 1 or 2.

Of note are methods of Preferred 9 wherein one $R^4$ group is attached to the phenyl ring at the 2-position and said $R^4$ is $CH_3$, Cl or Br; and a second $R^4$ is H, F, Cl, Br, I, CN or $CF_3$.

Preferred 10. Methods of Preferred 9 wherein J substituted with 1 to 3 $R^5$ is J-6; V is N or CH; and $R^7$ is $CH_3$, $CF_3$, $OCH_2CF_3$, $OCHF_2$ or halogen.

Preferred 11. Methods of Preferred 10 wherein $R^{6a}$ is F, Cl or Br; and $R^7$ is halogen or $CF_3$.

Preferred 12. Methods of Preferred 9 wherein J substituted with from 1 to 3 $R^5$ is J-7; and $R^9$ is $C_2$-$C_6$ alkyl or $C_1$-$C_6$ haloalkyl.

Of note are methods of Preferred 12 wherein V is N or CH; $R^{6a}$ is Cl or Br; and $R^9$ is $CF_3$, $CHF_2$, $CH_2CF_3$, $CF_2CHF_2$.

Preferred 13. Methods of Preferred 9 wherein J substituted with from 1 to 3 $R^5$ is J-8; V is N; $R^{6a}$ is Cl or Br; and $R^7$ is halogen or $CF_3$.

Preferred 14. Methods of Preferred 9 wherein J substituted with from 1 to 3 $R^5$ is J-9; $R^{6a}$ is Cl or Br; and $R^7$ is $CF_3$.

Preferred 15. Methods of Preferred 9 wherein J substituted with from 1 to 3 $R^5$ is J-10; $R^{6a}$ is Cl or Br; and $R^9$ is $CH_2CF_3$, $CHF_2$ or $CF_3$.

Preferred 16. Methods of Preferred 9 wherein J substituted with from 1 to 3 $R^5$ is J-11; $R^{6a}$ is Cl or Br; and $R^7$ is halogen, $OCH_2CF_3$, $OCHF_2$ or $CF_3$.

Preferred 17. Methods of Preferred 9 wherein J substituted with from 1 to 3 $R^5$ is J-12; $R^{6a}$ is Cl or Br; $R^7$ is halogen, $OCH_2CF_3$, $OCHF_2$ or $CF_3$; and $R^9$ is $CH_2CF_3$, $CHF_2$ or $CF_3$.

Preferred 18. Methods of Preferred 9 wherein J substituted with from 1 to 3 $R^5$ is J-13; $R^{6a}$ is Cl or Br; and $R^9$ is $CH_2CF_3$, $CHF_2$ or $CF_3$.

Specifically preferred methods are those comprising compounds selected from the group consisting of:

N-[2-[3-bromo-1-(3-chloro-2-pyridinyl)-1H-pyrazol-5-yl]-6-chloro-8-methyl-4H-3,1-benzoxazin-4-ylidene]methanamine, N-[2-[3-bromo-1-(3-chloro-2-pyridinyl)-1H-pyrazol-5-yl]-6-chloro-8-methyl-4H-3,1-benzoxazin-4-ylidene]-2-propanamine, N-[2-[3-bromo-1-(3-chloro-2-pyridinyl)-1H-pyrazol-5-yl]-6-chloro-8-methyl-4H-3,1-benzoxazin-4-ylidene]ethanamine, N-[6-chloro-2-[3-chloro-1-(3-chloro-2-pyridinyl)-1H-pyrazol-5-yl]-8-methyl-4H-3,1-benzoxazin-4-ylidene]methanamine, N-[6-chloro-2-[3-chloro-1-(3-chloro-2-pyridinyl)-1H-pyrazol-5-yl]-8-methyl-4H-3,1-benzoxazin-4-ylidene]-2-propanamine, N-[6-chloro-2-[3-chloro-1-(3-chloro-2-pyridinyl)-1H-pyrazol-5-yl]-8-methyl-4H-3,1-benzoxazin-4-ylidene]ethanamine, N-[6-chloro-2-[1-(3-chloro-2-pyridinyl)-3-(trifluoromethyl)-1H-pyrazol-5-yl]-8-methyl-4H-3,1-benzoxazin-4-ylidene]methanamine, N-[6-chloro-2-[1-(3-chloro-2-pyridinyl)-3-(trifluoromethyl)-1H-pyrazol-5-yl]-8-methyl-4H-3,1-benzoxazin-4-ylidene]-2-propanamine, N-[6-chloro-2-[1-(3-chloro-2-pyridinyl)-3-(trifluoromethyl)-1H-pyrazol-5-yl]-8-methyl-4H-3,1-benzoxazin-4-ylidene]ethanamine, N-[6-chloro-2-[1-(3-chloro-2-pyridinyl)-3-(trifluoromethyl)-1H-pyrazol-5-yl]-8-methyl-4H-3,1-benzoxazin-4-ylidene]-2-methyl-2-propanamine, N-[2-[3-bromo-1-(3-chloro-2-pyridinyl)-1H-pyrazol-5-yl]-8-methyl-4H-3,1-benzoxazin-4-ylidene]-2-propanamine, N-[2-[3-bromo-1-(3-chloro-2-pyridinyl)-1H-pyrazol-5-yl]-8-methyl-4H-3,1-benzoxazin-4-ylidene]-2-methyl-2-propanamine, N-[2-[1-(3-chloro-2-pyridinyl)-3-(trifluoromethyl)-1H-pyrazol-5-yl]-8-methyl-4H-3,1-benzoxazin-4-ylidene]-2-propanamine and N-[2-[1-(3-chloro-2-pyridinyl)-3-(trifluoromethyl)-1H-pyrazol-5-yl]-8-methyl-4H-3,1-benzoxazin-4-ylidene]-2-methyl-2-propanamine.

Also preferred are:

Preferred 19. Methods of Preferred 1 wherein

B is $NR^1$;

J substituted with from 1 to 3 $R^5$ is J-6 (as defined above in Preferred 8);

each $R^1$ is independently $C_1$-$C_6$ alkyl;

$R^2$ is H or $C_1$-$C_6$ alkyl; or $R^1$ and $R^2$ are taken together to form a linking chain of 2 to 5 members including at least one carbon member, optionally including no more than two carbon members as C(=O), and optionally one member selected from nitrogen and oxygen, optionally substituted with 1 to 4 substituents selected from $R^3$;

each $R^3$ is independently $C_1$-$C_2$ alkyl, halogen, CN, $NO_2$ or $C_1$-$C_2$ alkoxy; and one $R^4$ group is attached to the phenyl ring at the 2-position and said $R^4$ is $CH_3$, Cl or Br; and a second $R^4$ is H, F, Cl, Br, I or $CF_3$.

Of further note are methods comprising compounds of Preferred 19, $R^1$ and $R^2$ can be taken together to form a linking chain selected from the group consisting of —$CH_2CH_2$—, —$CH_2CH_2CH_2$—, —$CH_2CH_2C(=O)$—, H=C($CH_3$)—, —C($CH_3$)=CH—, and —CH=N—; such that the left end of the moiety is attached at the $R^1$ location and the right end of the moiety is attached at the $R^2$ location.

Specifically preferred is the method of Preferred 19 comprising the compound:

7,9-Dichloro-5-[1-(3-chloro-2-pyridinyl)-3-(trifluoromethyl)-1H-pyrazol-5-yl]-2,3-dihydroimidazo[1,2-c]quinazoline.

This invention also pertains to compositions for controlling an invertebrate pest comprising a biologically effective amount of a compound of Formula I. Preferred compositions are those comprising the compounds described in Preferred 1 through Preferred 19 and those listed in the specifically preferred methods above.

Preferred compounds for ease of synthesis and/or biological efficacy are:

Preferred A. Compounds of Formula I wherein

B is O;

$R^2$ is H or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $C_1$-$C_2$ alkoxy, $C_1$-$C_2$ alkylthio, $C_1$-$C_2$ alkylsulfinyl and $C_1$-$C_2$ alkylsulfonyl;

one R⁴ group is attached to the phenyl ring at the 2-position or 5-position, and said R⁴ is $C_1$-$C_4$ alkyl, $C_1$-$C_4$ haloalkyl, halogen, CN, NO₂, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl;

each R⁵ is independently halogen, $C_1$-$C_4$ alkyl, $C_1$-$C_2$ alkoxy, $C_1$-$C_4$ haloalkyl, CN, NO₂, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or each R⁵ is independently a phenyl or a 5- or 6-membered heteroaromatic ring, each ring optionally substituted with one to three substituents independently selected from R⁶; or two R⁵ groups when attached to adjacent carbon atoms are taken together as —OCF₂O—, CF₂CF₂O—, or —CF₂CF₂O—; and n is 1 or 2.

Preferred B. Compounds of Preferred A wherein

J is a phenyl group optionally substituted with from 1 to 4 R⁵;

R² is $C_1$-$C_4$ alkyl optionally substituted with halogen, CN, OCH₃ or S(O)ₚCH₃;

one R⁴ group is attached to the phenyl ring at the 2-position and said R⁴ is CH₃, CF₃, OCF₃, OCHF₂, S(O)ₚCF₃, S(O)ₚCHF₂, CN or halogen;

a second R⁴ is H, F, Cl, Br, I, or CF₃;

each R⁵ is independently halogen, methyl, CF₃, OCF₃, OCHF₂, S(O)ₚCF₃, S(O)ₚCHF₂, OCH₂CF₃, OCF₂CHF₂, S(O)ₚCH₂CF₃ or S(O)ₚCF₂CHF₂; or a phenyl, pyrazole, imidazole, triazole, pyridine or pyrimidine ring, each ring optionally substituted with one to three substituents independently selected from $C_1$-$C_4$ alkyl, $C_1$-$C_4$ haloalkyl, halogen and CN; and p is 0, 1 or 2.

Preferred C. Compounds of Preferred B wherein R² is H, Me, Et, i-propyl or t-butyl.

Preferred D. Compounds of Preferred A wherein

J is a 5- or 6-membered heteroaromatic ring selected from the group consisting of J-1, J-2, J-3, J-4 and J-5, each J optionally substituted with 1 to 3 R⁵

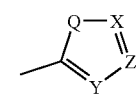
J-1

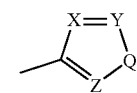
J-2

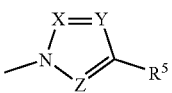
J-3

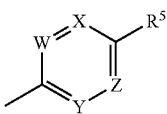
J-4

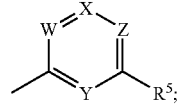
J-5

Q is O, S, NH or NR⁵; and

W, X, Y and Z are independently N, CH or CR⁵, provided that in J-4 and J-5 at least one of W, X, Y or Z is N; and each R⁵ is independently $C_1$-$C_4$ alkyl, $C_1$-$C_4$ haloalkyl, halogen, CN, NO₂, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or a phenyl or a 5- or 6-membered heteroaromatic ring, each ring optionally substituted with one to three substituents independently selected from R⁶.

Preferred E. Compounds of Preferred D wherein

J substituted with 1 to 3 R⁵ is selected from the group consisting of J-6, J-7, J-8, J-9, J-10, J-11, J-12 and J-13

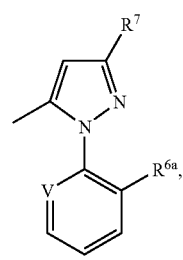
J-6

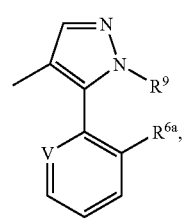
J-7

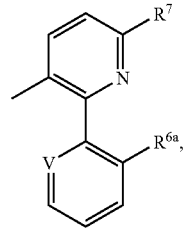
J-8

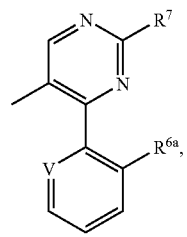
J-9

-continued

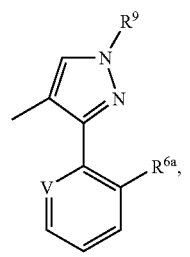
J-10

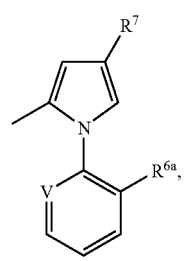
J-11

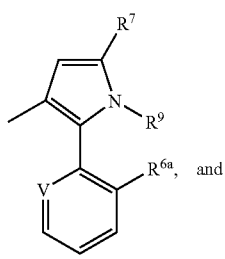
J-12

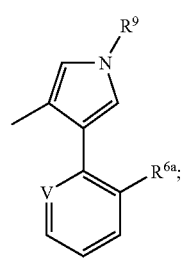
J-13

V is N, CH, CF, CCl, CBr or Cl;
each $R^{6a}$ is independently H or $R^6$;
$R^6$ is $C_1$-$C_6$ alkyl, $C_3$-$C_6$ cycloalkyl $C_1$-$C_6$ haloalkyl, halogen, CN, $C_1$-$C_4$ alkoxy, $C_1$-$C_4$ haloalkoxy or $C_1$-$C_4$ haloalkylthio;
each $R^7$ is independently $C_1$-$C_6$ alkyl, $C_1$-$C_6$ haloalkyl, halogen, CN, $C_1$-$C_4$ alkoxy, $C_1$-$C_4$ haloalkoxy or $C_1$-$C_4$ haloalkylthio;
$R^9$ is $C_2$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl;
$R^{10}$ is $C_1$-$C_4$ alkyl or $C_1$-$C_4$ haloalkyl;
$R^{11}$ is $C_1$-$C_4$ alkyl; and
n is 1 or 2.

Note that $R^7$ and $R^9$ are subsets of $R^5$. Note that the F, Cl, Br or I atoms encompassed within V are a subset of $R^6$. Of note are compounds of Preferred E wherein V is N. Also of note are compounds of Preferred E wherein V is CH, CF, CCl or CBr. Of particular note are compounds of Preferred E wherein V is N or CH.

Preferred F. Compounds of Preferred E wherein
$R^2$ is $C_1$-$C_4$ alkyl optionally substituted with halogen, CN, $OCH_3$ or $S(O)_pCH_3$; or $CH_2C\equiv CH$;
one $R^4$ group is attached to the phenyl ring at the 2-position and said $R^4$ is $CH_3$, $CF_3$, $OCF_3$, $OCHF_2$, $S(O)_pCF_3$, $S(O)_pCHF_2$, CN or halogen;
a second $R^4$ is H, F, Cl, Br, I or $CF_3$;
$R^{6a}$ is H, $C_1$-$C_4$ alkyl, $C_1$-$C_4$ haloalkyl, halogen or CN;
$R^7$ is $CH_3$, $CF_3$, $OCH_2CF_3$, $OCHF_2$ or halogen;
$R^9$ is $CH_2CF_3$, $CHF_2$ or $CF_3$; and
p is 0, 1 or 2.

Of note are compounds of Preferred F wherein one $R^4$ group is attached to the phenyl ring at the 2-position and said $R^4$ is $CH_3$, Cl or Br; and a second $R^4$ is H, F, Cl, Br, I or $CF_3$.

Preferred G. Compounds of Preferred F wherein J substituted with from 1 to 3 $R^5$ is J-6; V is N or CH; and $R^7$ is $CH_3$, $CF_3$, $OCH_2CF_3$, $OCHF_2$ or halogen.

Preferred H. Compounds of Preferred G wherein $R^{6a}$ is F, Cl or Br; and $R^7$ is halogen or $CF_3$.

Preferred I. Compounds of Preferred F wherein J substituted with 1 to 3 $R^5$ is J-7; and $R^9$ is $C_2$-$C_6$ alkyl or $C_1$-$C_6$ haloalkyl.

Of note are compounds of Preferred I wherein V is N or CH; $R^{6a}$ is Cl or Br; and $R^9$ is $CF_3$, $CHF_2$, $CH_2CF_3$, $CF_2CHF_2$.

Preferred J. Compounds of Preferred F wherein J substituted with 1 to 3 $R^5$ is J-8; V is N; $R^{6a}$ is Cl or Br; and $R^7$ is halogen or $CF_3$.

Preferred K. Compounds of Preferred F wherein J substituted with 1 to 3 $R^5$ is J-9; $R^{6a}$ is Cl or Br; and $R^7$ is $CF_3$.

Preferred L. Compounds of Preferred F wherein J substituted with 1 to 3 $R^5$ is J-10; $R^{6a}$ is Cl or Br; and $R^9$ is $CH_2CF_3$, $CHF_2$ or $CF_3$.

Preferred M. Compounds of Preferred F wherein J substituted with 1 to 3 $R^5$ is J-11; $R^{6a}$ is Cl or Br; and $R^7$ is halogen, $OCH_2CF_3$, $OCHF_2$ or $CF_3$.

Preferred N. Compounds of Preferred F wherein J substituted with 1 to 3 $R^5$ is J-12; $R^{6a}$ is Cl or Br; $R^7$ is halogen, $OCH_2CF_3$, $OCHF_2$ or $CF_3$; and $R^9$ is $CH_2CF_3$, $CHF_2$ or $CF_3$.

Preferred O. Compounds of Preferred F wherein J substituted with 1 to 3 $R^5$ is J-13; $R^{6a}$ is Cl or Br; and $R^9$ is $CHF_2CF_3$, $CH_2$ or $CF_3$.

Specifically preferred are compounds selected from the group consisting of:
N-[2-[3-bromo-1-(3-chloro-2-pyridinyl)-1H-pyrazol-5-yl]-6-chloro-8-methyl-4H-3,1-benzoxazin-4-ylidene]methanamine,
N-[2-[3-bromo-1-(3-chloro-2-pyridinyl)-1H-pyrazol-5-yl]-6-chloro-8-methyl-4H-3,1-benzoxazin-4-ylidene]-2-propanamine,
N-[2-[3-bromo-1-(3-chloro-2-pyridinyl)-1H-pyrazol-5-yl]-6-chloro-8-methyl-4H-3,1-benzoxazin-4-ylidene]ethanamine,
N-[6-chloro-2-[3-chloro-1-(3-chloro-2-pyridinyl)-1H-pyrazol-5-yl]-8-methyl-4H-3,1-benzoxazin-4-ylidene]methanamine,
N-[6-chloro-2-[3-chloro-1-(3-chloro-2-pyridinyl)-1H-pyrazol-5-yl]-8-methyl-4H-3,1-benzoxazin-4-ylidene]-2-propanamine,
N-[6-chloro-2-[3-chloro-1-(3-chloro-2-pyridinyl)-1H-pyrazol-5-yl]-8-methyl-4H-3,1-benzoxazin-4-ylidene]ethanamine,
N-[6-chloro-2-[1-(3-chloro-2-pyridinyl)-3-(trifluoromethyl)-1H-pyrazol-5-yl]-8-methyl-4H-3,1-benzoxazin-4-ylidene]methanamine,
N-[6-chloro-2-[1-(3-chloro-2-pyridinyl)-3-(trifluoromethyl)-1H-pyrazol-5-yl]-8-methyl-4H-3,1-benzoxazin-4-ylidene]-2-propanamine, N-[6-chloro-2-[1-(3-chloro-2-pyridinyl)-3-(trifluoromethyl)-1H-pyrazol-5-yl]-8-methyl-4H-3,1-benzoxazin-4-ylidene]ethanamine,
N-[6-chloro-2-[1-(3-chloro-2-pyridinyl)-3-(trifluoromethyl)-1H-pyrazol-5-yl]-8-methyl-4H-3,1-benzoxazin-4-ylidene]-2-methyl-2-propanamine,
N-[2-[3-bromo-1-(3-chloro-2-pyridinyl)-1H-pyrazol-5-yl]-8-methyl-4H-3,1-benzoxazin-4-ylidene]-2-propanamine,
N-[2-[3-bromo-1-(3-chloro-2-pyridinyl)-1H-pyrazol-5-yl]-8-methyl-4H-3,1-benzoxazin-4-ylidene]-2-methyl-2-propanamine,
N-[2-[1-(3-chloro-2-pyridinyl)-3-(trifluoromethyl)-1H-pyrazol-5-yl]-8-methyl-4H-3,1-benzoxazin-4-ylidene]-2-propanamine and
N-[2-[1-(3-chloro-2-pyridinyl)-3-(trifluoromethyl)-1H-pyrazol-5-yl]-8-methyl-4H-3,1-benzoxazin-4-ylidene]-2-methyl-2-propanamine.

Of note are compounds of Formula I wherein
B is $NR^1$;
J substituted with 1 to 3 $R^5$ is J-6 (as defined above in Preferred 8);
each $R^1$ is independently $C_1$-$C_6$ alkyl;
$R^2$ is H or $C_1$-$C_6$ alkyl; or
$R^1$ and $R^2$ are taken together to form a linking chain of 2 to 5 members including at least one carbon member, optionally including no more than two carbon members as C(=O), and optionally one additional member selected from nitrogen and oxygen, optionally substituted with from 1 to 4 substituents selected from $R^3$;
each $R^3$ is independently $C_1$-$C_2$ alkyl, halogen, CN, $NO_2$ or $C_1$-$C_2$ alkoxy; and one $R^4$ group is attached to the phenyl ring at the 2-position and said $R^4$ is $CH_3$, Cl or Br; and a second $R^4$ is H, F, Cl, Br, I or $CF_3$.

Of further note are compounds wherein in Formula I, $R^1$ and $R^2$ can be taken together to form a linking chain selected from the group consisting of —$CH_2CH_2$—, —$H_2CH_2CH_2$—, —$H_2CH_2C$(=O), —CH=C($CH_3$), —C($CH_3$)=CH—, and —CH=N—; such that the left end of the moiety is attached at the $R^1$ location and the right end of the moiety is attached at the $R^2$ location.

Specifically preferred is the compound:
7,9-Dichloro-5-[1-(3-chloro-2-pyridinyl)-3-(trifluoromethyl)-1H-pyrazol-5-yl]-2,3-dihydroimidazo[1,2-c]quinazoline.

One or more of the following methods and variations as described in Schemes 1-35 can be used to prepare the compounds of Formula I. The definitions of B, J, V, $R^1$ through $R^6$ and n in the compounds of Formulae I, II and 2-96 below are as defined above in the Summary of the Invention. Compounds of Formulae Ia-f, IIa-c, 3a, 4a-t, 10a, 18a, 19a-c and 20a are various subsets of the compounds of Formula I, II, 3, 4, 10, 18, 19 and 20, respectively.

Compounds of Formula Ia or Ib (compounds of Formula I wherein B is O or S respectively) can be prepared from compounds of Formula IIa or Formula IIb respectively by cyclization in the presence of dehydration agents such as $POCl_3$, $POCl_3$/$PCl_5$, $SOCl_2$ or oxalyl chloride. This cyclization is typically conducted in solvents such as dichloroethane, dichloromethane, chloroform, benzene, toluene, xylenes, hexanes, cyclohexane, 1,4-dioxane, tetrahydrofuran and chlorobenzene in the temperature range from 0° C. to the reflux temperature of the mixture. Alternatively, the dehydrative cyclization can be effected by treatment of Formula IIa or Formula IIb with triphenyl phosphine and either bromine or iodine, optionally in the presence of tertiary amine bases such as triethylamine or diisopropylethylamine. See *Monatsh. Chem.* 1989, 120, 973-980 and *J. Org. Chem.* 2000, 65, 1022-1030 for representative procedures.

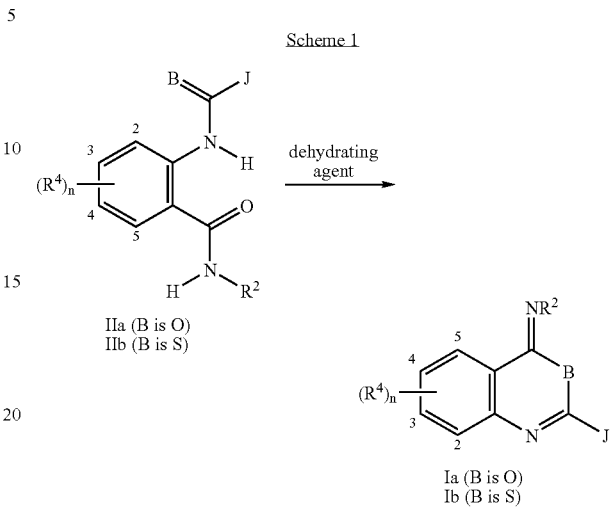

Scheme 1

Coupling of an amine of Formula 2 with an acid chloride of Formula 3 in the presence of an acid scavenger can provide the compound of Formula IIa (Scheme 2). Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. The coupling can be run in a suitable inert solvent such as tetrahydrofuran, dioxane, diethylether or dichloromethane to afford the anilide of Formula IIa.

In a subsequent step, amides of Formula IIa can be converted to thioamides of Formula IIb using a variety of standard thio transfer reagents including phosphorus pentasulfide and Lawesson's reagent.

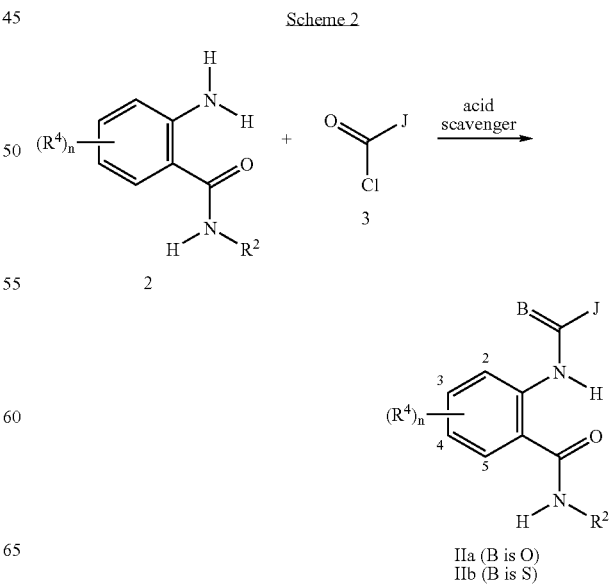

Scheme 2

An alternate procedure for the preparation of compounds of Formula IIa involves coupling of an amine of Formula 2 with an acid of Formula 4 in the presence of a dehydrating agent such as dicyclohexylcarbodiimide (DCC), 1,1'-carbonyldiimidazole, bis(2-oxo-3-oxazolidinyl)phosphinic chloride or benzotriazol-1-yloxy-tris-(dimethylamino)-phosphonium hexafluorophosphate (Scheme 3). Polymer supported reagents are again useful here, such as polymer-bound cyclohexylcarbodiimide. The coupling can be run in a suitable inert solvent such as dichloromethane or N,N-dimethylformamide. Synthetic procedures of Schemes 2 and 3 are only representative examples of useful methods for the preparation of Formula II compounds as the synthetic literature is extensive for this type of reaction.

Scheme 3

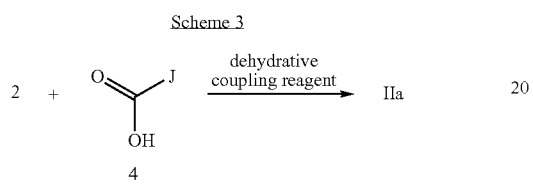

One skilled in the art will also realize that acid chlorides of Formula 3 may be prepared from acids of Formula 4 by numerous well-known methods. For example, acid chlorides of Formula 3 are readily made from carboxylic acids of Formula 4 by reacting the carboxylic acid 4 with thionyl chloride or oxalyl chloride in an inert solvent such as toluene or dichloromethane in the presence of a catalytic amount of N,N-dimethylformamide.

Amines of Formula 2 are typically available from the corresponding 2-nitrobenzamides of Formula 5 via catalytic hydrogenation of the nitro group (Scheme 4). Typical procedures involve reduction with hydrogen in the presence of a metal catalyst such as palladium on carbon or platinum oxide and in hydroxylic solvents such as ethanol and isopropanol. They can also be prepared by reduction with zinc in acetic acid. These procedures are well documented in the chemical literature.

Scheme 4

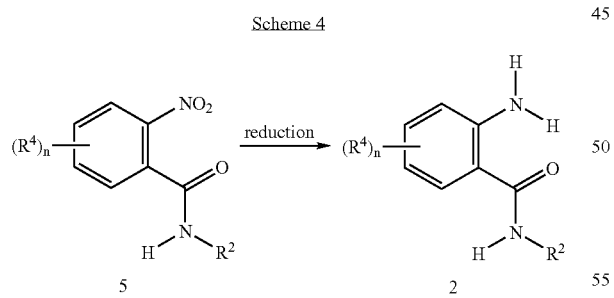

The intermediate 2-nitrobenzamides of Formula 5 are readily prepared from commercially available 2-nitrobenzoic acids (Scheme 5). Typical methods for amide formation can be applied here. These include direct dehydrative coupling of acids of Formula 6 with amines of Formula 7 using for example DCC, and conversion of the acids to activated forms such as the acid chlorides or anhydrides and subsequent coupling with amines to form amides of Formula 5. Alkyl chloroformates, such as ethyl chloroformate or isopropyl chloroformate, are especially useful reagents for this type of reaction involving activation of the acid. The chemical literature is extensive on methods for amide formation.

Scheme 5

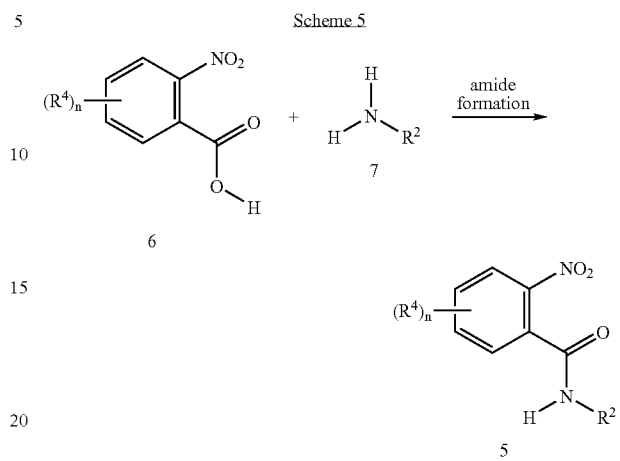

Intermediate anthranilic amides of Formula 2 may also be prepared from isatoic anhydrides of Formula 8 as shown in Scheme 6. Typical procedures involve combination of equimolar amounts of the amine 7 with the isatoic anhydride in polar aprotic solvents such as pyridine and N,N-dimethylformamide at temperatures ranging from room temperature to 100° C. Isatoic anhydrides of Formula 8 may be made by methods described in Coppola, *Synthesis* 1980, 505-36.

Scheme 6

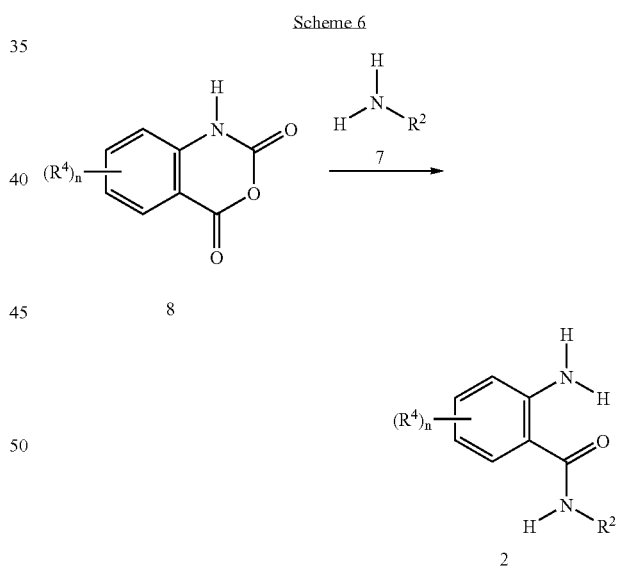

As shown in Scheme 7, an alternate procedure for the preparation of compounds of Formula IIa involves reaction of an amine of Formula 7 with a benzoxazinone of Formula 10. The reaction of Scheme 7 can be run neat or in a variety of suitable solvents including tetrahydrofuran, diethyl ether, pyridine, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and*

*Medicinal Chemistry* 2000, 8, 2095-2103 and references cited therein. See also Coppola, *J. Heterocyclic Chemistry* 1999, 36, 563-588.

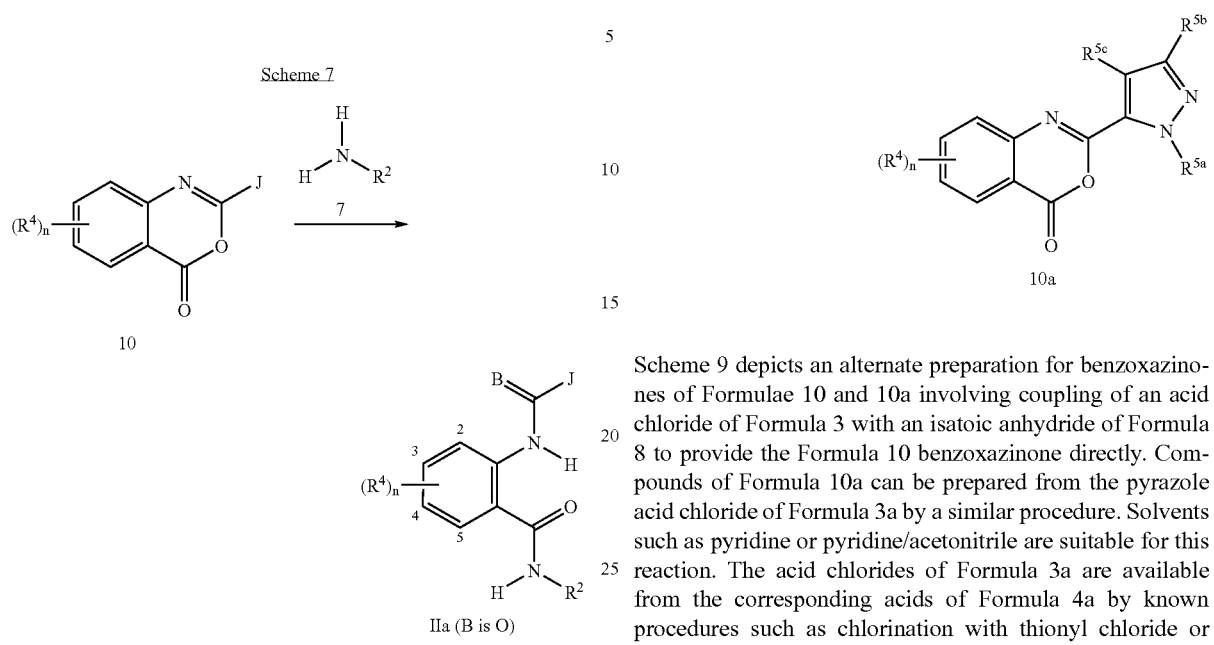

Benzoxazinones of Formula 10 can be prepared by a variety of procedures. Two procedures that are especially useful are detailed in Schemes 8 and 9. In Scheme 8, a benzoxazinone of Formula 10 is prepared directly via coupling of a carboxylic acid of Formula 4 with an anthranilic acid of Formula 11. This involves sequential addition of methanesulfonyl chloride to a carboxylic acid of Formula 4 in the presence of an amine base such as triethylamine or pyridine, followed by the addition of an anthranilic acid of Formula 11, followed by a second addition of triethylamine and methanesulfonyl chloride. This procedure generally affords good yields of the benzoxazinone and is especially useful for preparing compounds of Formula 10a from pyrazolecarboxylic acids of Formula 4a.

Scheme 9 depicts an alternate preparation for benzoxazinones of Formulae 10 and 10a involving coupling of an acid chloride of Formula 3 with an isatoic anhydride of Formula 8 to provide the Formula 10 benzoxazinone directly. Compounds of Formula 10a can be prepared from the pyrazole acid chloride of Formula 3a by a similar procedure. Solvents such as pyridine or pyridine/acetonitrile are suitable for this reaction. The acid chlorides of Formula 3a are available from the corresponding acids of Formula 4a by known procedures such as chlorination with thionyl chloride or oxalyl chloride.

Preparation of the isatoic anhydrides of Formula 8 can be achieved from isatins of Formula 13 as outlined in Scheme 10. Isatins of Formula 13 are available from aniline derivatives of Formula 12 following literature procedures. Oxidation of isatin 13 with hydrogen peroxide generally affords good yields of the corresponding isatoic anhydride 8 (*Angew. Chem. Int. Ed. Engl.* 1980, 9, 222-223). Isatoic anhydrides are also available from the anthranilic acids 11 via many known procedures involving reaction of 11 with phosgene or a phosgene equivalent.

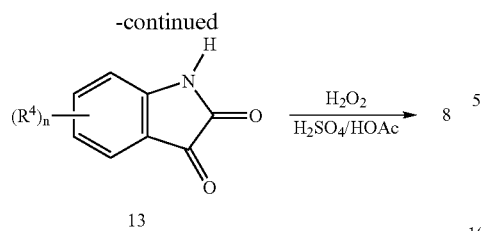

Compounds of Formula Ic or Id (compounds of Formula I wherein B is $NR^1$) can be prepared from anthranilonitriles of Formula 14 by cyclization with an amide of Formula 15 in the presence of dehydration agents such as $POCl_3$, $POCl_3/PCl_5$ or $SOCl_2$ (Scheme 11). This cyclization is typically conducted in solvents such as dichloroethane, dichloromethane, chloroform, benzene, toluene, xylenes, hexanes, cyclohexane, 1,4-dioxane, tetrahydrofuran and chlorobenzene in the temperature range from 0° C. to the reflux temperature of the mixture. The resultant compounds of Formula Ic (wherein $R^2$ is H) can be treated with electrophiles of Formula 16 (wherein Lg is a leaving group such as halogen and alkyl or aryl suphonates), optionally in the presence of an acid scavenger, to provide compounds of Formula Id (wherein $R^2$ is other than H). Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. These reactions are typically conducted in solvents such as dichloroethane, dichloromethane, chloroform, benzene, toluene, xylenes, hexanes, cyclohexane, 1,4-dioxane, tetrahydrofuran dimethylsufoxide N,N-dimethylformamide, N,N-dimethylacetamide and chlorobenzene in the temperature range from 0° C. to the reflux temperature of the mixture. Compounds of Formula Id may be prepared from compounds of Formulae 14 and 15 (wherein $R^1$ is H) by similar procedures. Alkylation of Formula Id with an alkylating agent with two leaving groups (e.g. ethylene dibromide or propylene dibromide) provides compounds of Formula Ie wherein, for example, the moiety $R^1$-$R^2$ is $CH_2CH_2$ or $CH_2CH_2CH_2$.

Compounds of Formula 14 are well known in the art and are commercially available or available by well-established procedures. Amides of Formula 15 can be prepared from acids of Formula 4 or acid chlorides of Formula 3 by reaction with amines of the formula $R^1NH_2$ according to methods described for Schemes 2, 3 and 5.

A shown in Scheme 11a, compounds of Formula If may also be prepared by the dehydration of compounds of Formula IIc. Formula IIc compounds can be prepared from anilines with an ortho-heterocycle containing a NH moiety (Formula 16) and compounds of Formula 3 in the presence of an acid scavenger according to methods described for Scheme 2. In some instances, the dehydration of IIc can occur under the coupling conditions to provide Formula If directly. See Example 3 for a more detailed example of this reaction sequence.

Scheme 11

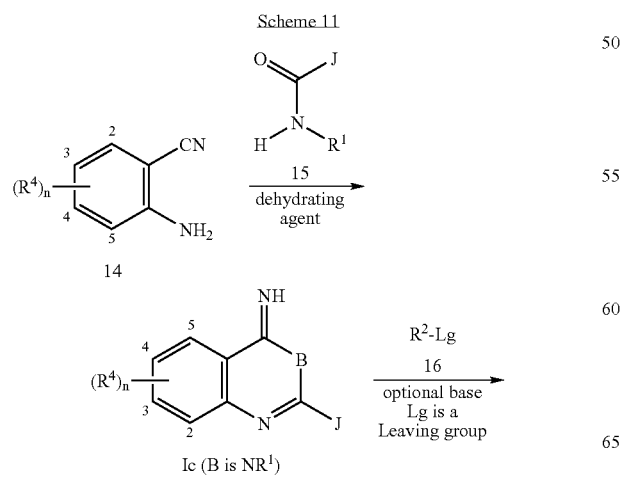

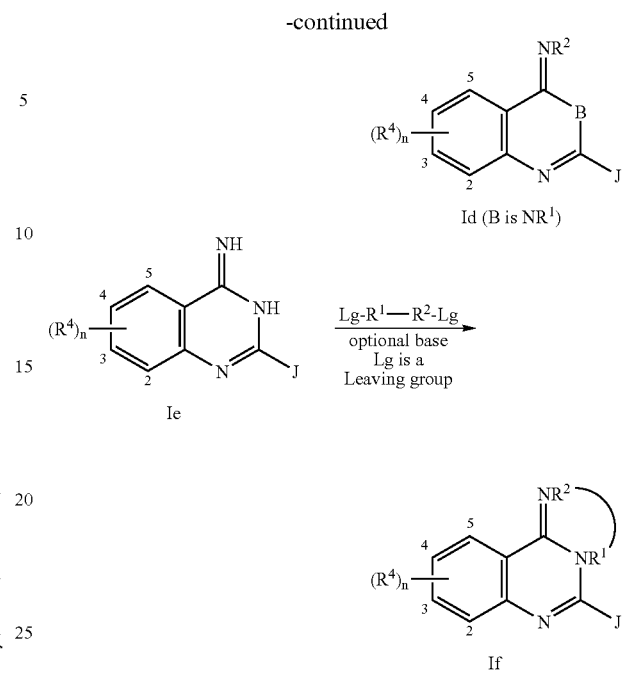

Scheme 11a

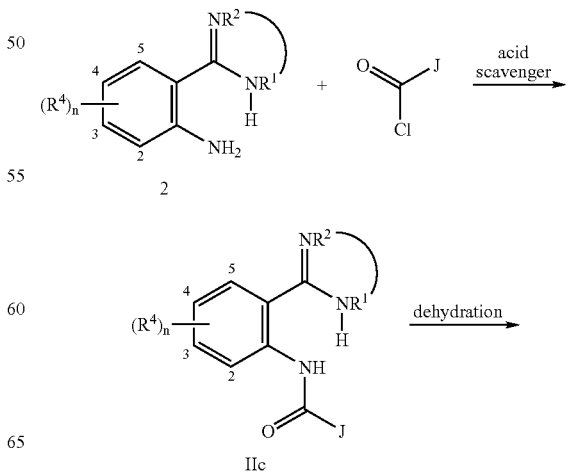

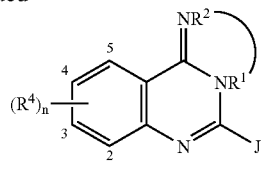

If

Benzoic acids of Formula 4, wherein J is an optionally substituted phenyl ring, are well known in the art and are commercially available or available by well-established procedures. Heterocyclic acids of Formula 4, wherein J is an optionally substituted heterocycle, can be prepared by procedures outlined in Schemes 12-35. Both general and specific references to a wide variety of heterocyclic acids including thiophenes, furans, pyridines, pyrimidines, triazoles, imidazoles, pyrazoles, thiazoles, oxazoles, isothiazoles, thiadiazoles, oxadiazoles, triazines, pyrazines, pyridazines, and isoxazoles can be found in the following compendia: *Rodd's Chemistry of Chemistry of Carbon Compounds*, Vol. *IVa* to *IVl.*, S. Coffey editor, Elsevier Scientific Publishing, New York, 1973; *Comprehensive Heterocyclic Chemistry*, Vol. 1-7, A. R. Katritzky and C. W. Rees editors, Pergamon Press, New York, 1984; *Comprehensive Heterocyclic Chemistry II*, Vol. 1-9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. Heterocyclic acids particularly useful for preparing compounds of Formula I of this invention include pyridine acids, pyrimidine acids and pyrazole acids. Procedures for the synthesis of representative examples of each are detailed in Schemes 12-35. A variety of heterocyclic acids and general methods for their synthesis may be found in PCT Patent Application Publication WO 98/57397.

Syntheses of pyrazoles of Formula 4a are described in Scheme 12. The synthesis of compounds of Formula 4a in Scheme 12 involves as the key step introduction of the $R^{5a}$ substituent via alkylation or arylation of the pyrazole of Formula 17 with compounds of Formula 18 (wherein Lg is a leaving group as defined above). Oxidation of the methyl group affords the pyrazole carboxylic acid. Some of the more preferred $R^{5b}$ groups include haloalkyl.

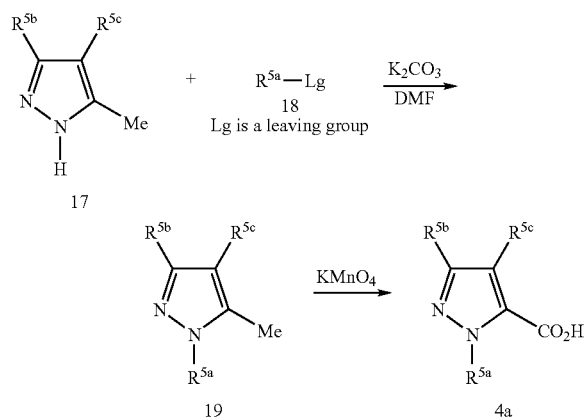

Synthesis of pyrazoles of Formula 4a is also described in Scheme 13. These acids may be prepared via metallation and carboxylation of compounds of Formula 20 as the key step. The $R^{5a}$ group is introduced in a manner similar to that of Scheme 12, i.e. via alkylation or arylation with a compound of Formula 18. Representative $R^{5b}$ groups include e.g. cyano, haloalkyl and halogen.

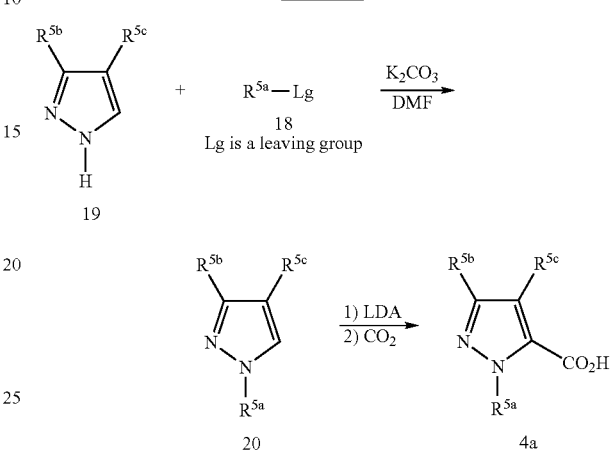

This procedure is particularly useful for preparing 1-(2-pyridinyl)pyrazolecarboxylic acids of Formula 4b (related to Preferred moiety J-6) as shown in Scheme 14. Reaction of a pyrazole of Formula 19 with a 2,3-dihalopyridine of Formula 18a affords good yields of the 1-pyridylpyrazole of Formula 20a with good specificity for the desired regiochemistry. Metallation of 20a with lithium diisopropylamide (LDA) followed by quenching of the lithium salt with carbon dioxide affords the 1-(2-pyridinyl)pyrazolecarboxylic acid of Formula 4b. See Example 1.

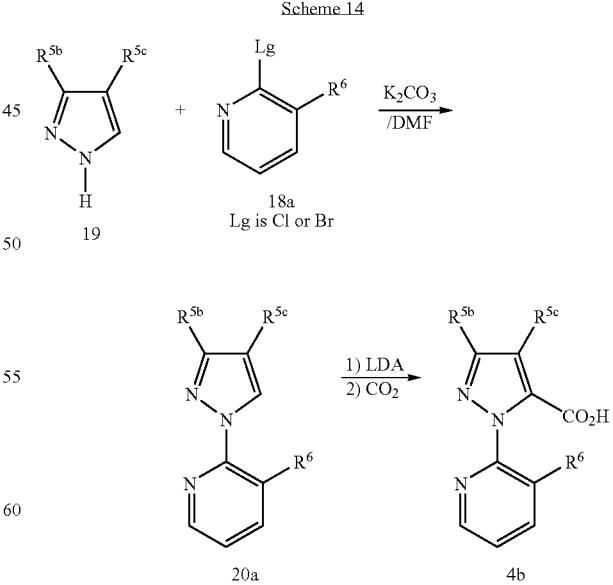

The synthesis of pyrazoles of Formula 4c is described in Scheme 15. They can be prepared via reaction of an optionally substituted phenyl hydrazine of Formula 21 with a ketopyruvate of Formula 22 to yield pyrazole esters of Formula 23. Hydrolysis of the esters affords the pyrazole acids of Formula 4c. This procedure is particularly useful for the preparation of compounds in which $R^{5a}$ is optionally substituted phenyl and $R^{5b}$ is haloalkyl.

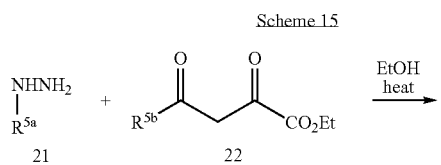

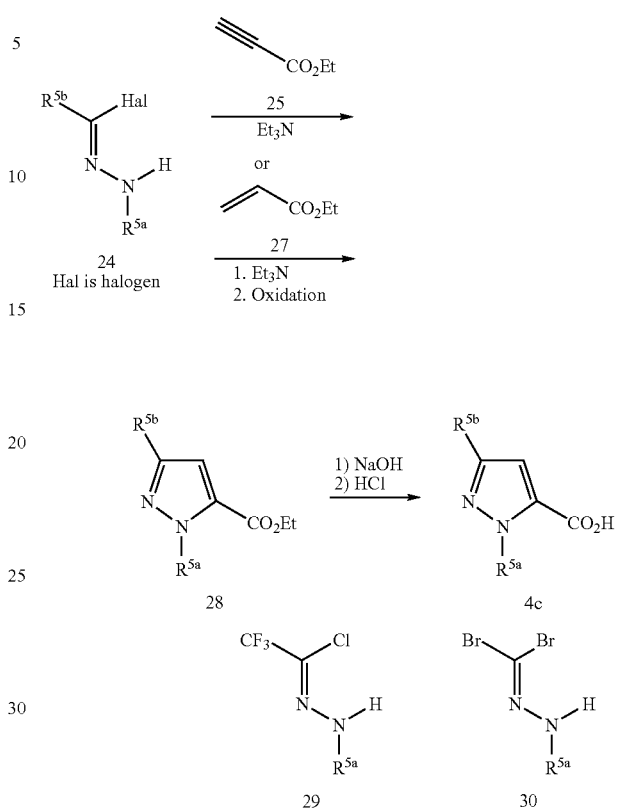

A variation of this sequence using a furyl group as a masked carboxylic acid is described in Example 2.

An alternate synthesis of pyrazole acids of Formula 4c is described in Scheme 16. They can be prepared via 3+2 cycloaddition of an appropriately substituted nitrilimine of Formula 24 with either substituted propiolates of Formula 25 or acrylates of Formula 27. Cycloaddition kith an acrylate requires additional oxidation of the intermediate pyrazoline to the pyrazole. Hydrolysis of the esters of Formula 28 affords the pyrazole acids of Formula 4c. Preferred iminohalides for this reaction include the trifluoromethyl iminochloride of Formula 29 and the iminodibromide of Formula 30. Compounds such as 29 are known (*J. Heterocycl. Chem.* 1985, 22(2), 565-8). Compounds such as 30 are available by known methods (*Tetrahedron Letters* 1999, 40, 2605). These procedures are particularly useful for the preparation of compounds where $R^{5a}$ is optionally substituted phenyl and $R^{5b}$ is haloalkyl or bromo.

The starting pyrazoles of Formula 19 are known compounds or can be prepared according to known methods. The pyrazole of Formula 19a (the compound of Formula 19 wherein $R^{5b}$ is $CF_3$ and $R^{5c}$ is H) is commercially available. The pyrazoles of Formula 19c (compounds of Formula 19 wherein $R^{5b}$ is Cl or Br and $R^{5c}$ is H) can be prepared by literature procedures (*Chem. Ber.* 1966, 99(10), 3350-7). A useful alternative method for the preparation of compound 19c is depicted in Scheme 17. Metallation of the sulfamoyl pyrazole of Formula 31 with n-butyllithium followed by direct halogenation of the anion with either hexachloroethane (for $R^{5b}$ being Cl) or 1,2-dibromotetrachloroethane (for $R^{5b}$ being Br) affords the halogenated derivatives of Formula 32. Removal of the sulfamoyl group with trifluoroacetic acid (TFA) at room temperature proceeds cleanly and in good yield to afford the pyrazoles of Formula 19c. One skilled in the art will recognize that Formula 19c is a tautomer of Formula 19b.

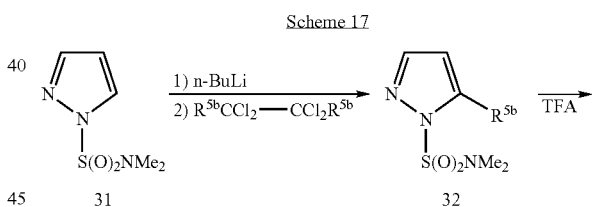

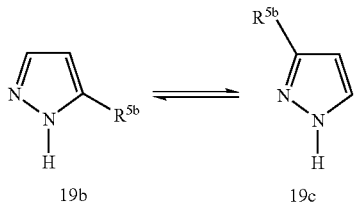

($R^{5b}$ is Cl or Br)

The synthesis of representative pyridine acids (4d) is depicted in Scheme 18. This procedure involves the known synthesis of pyridines from β-ketoesters of Formula 37 and 4-amino-butenones of Formula 36. Substituent groups $R^{5a}$ and $R^{5b}$ include e.g. alkyl and haloalkyl.

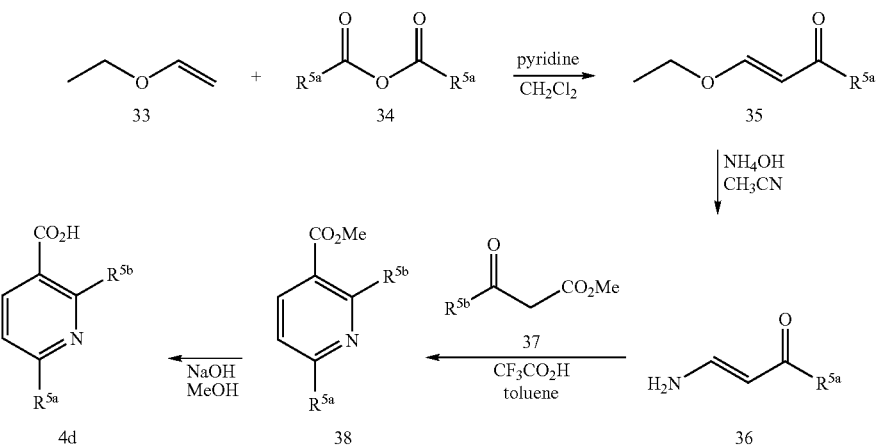

The synthesis of representative pyrimidine acids (4e) is depicted in Scheme 19. This procedure involves the known synthesis of pyrimidines from enamino-β-ketoesters of Formula 40 and amidines of Formula 41. Substituent groups $R^{5a}$ and $R^{5b}$ include e.g. alkyl and haloalkyl.

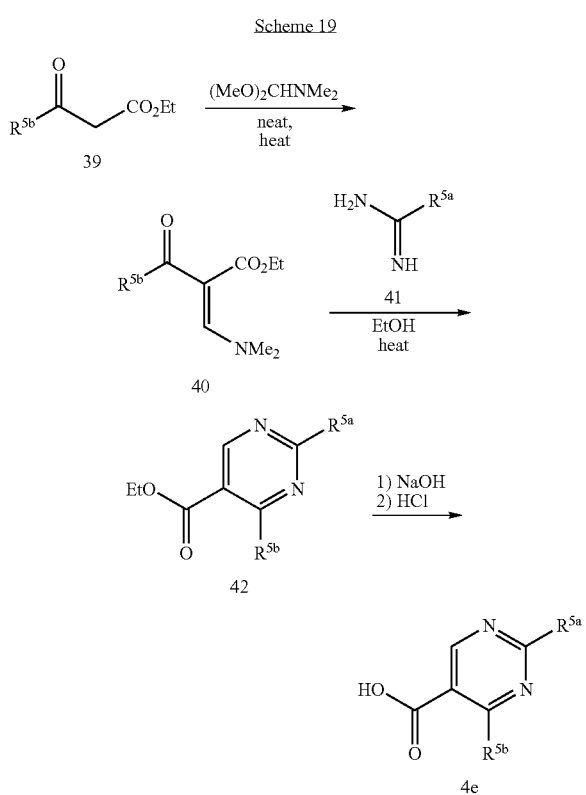

The synthesis of representative pyrazole acids of Formula 4f is depicted in Scheme 20. Reaction of a dimethylaminoylidene ketoester of Formula 45 with a substituted hydrazine (46) affords the pyrazole of Formula 47. Preferred $R^{5d}$ substituents include alkyl and haloalkyl, with 2,2,2-trifluoroethyl especially preferred. The esters of Formula 47 are converted to the acids of Formula 4f by standard hydrolysis methods.

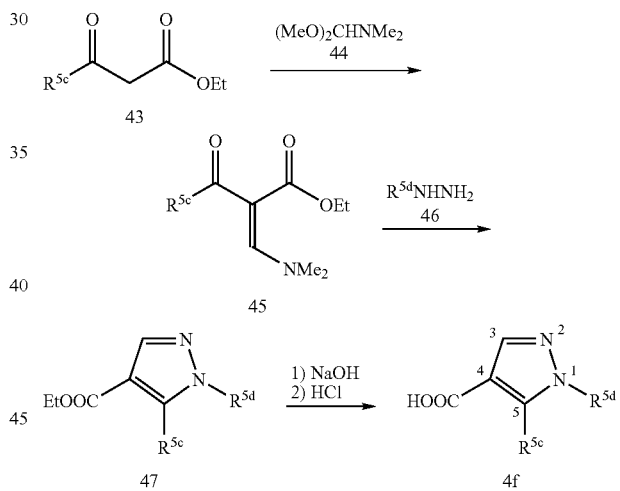

The synthesis of pyrazole acids of Formula 4g, which are related to the preferred moiety J-7 wherein $R^5$ is a substituted 2-pyridyl moiety attached to the 5-position of the pyrazole ring, is depicted in Scheme 21. This synthesis is conducted according to the general synthesis described for Scheme 20.

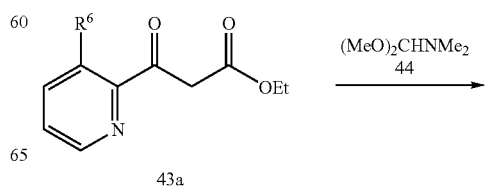

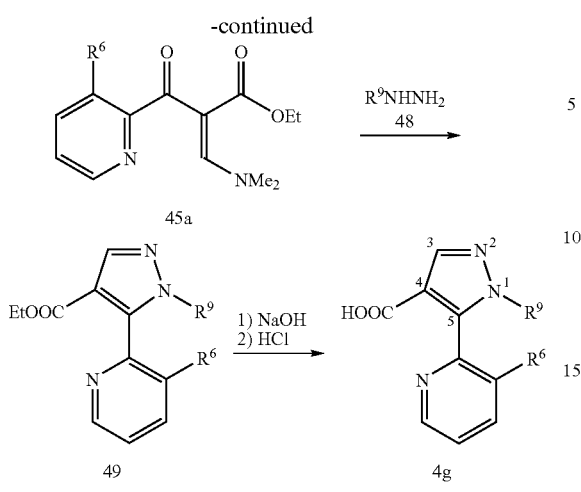

The synthesis of representative pyrazole acids of Formula 4h, as well as an alternative synthesis of Formula 4f, is depicted in Scheme 22.

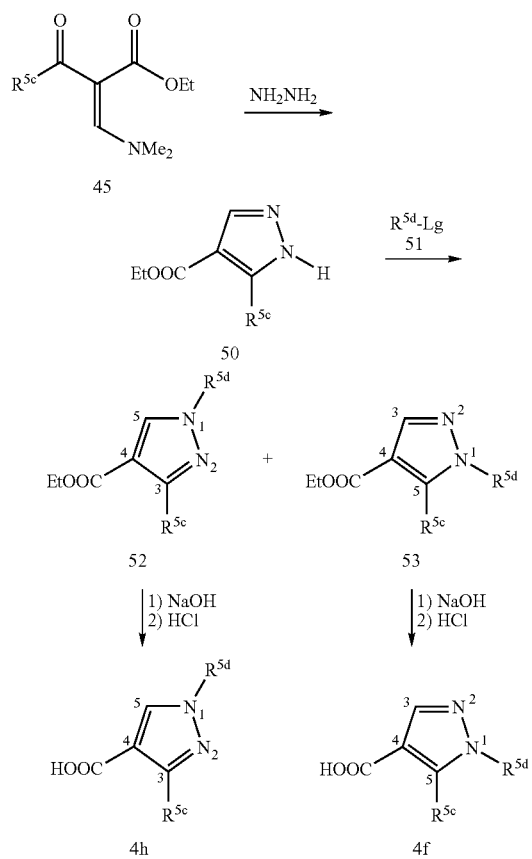

Reaction of the dimethylaminoylidene ketoester of Formula 45 with hydrazine affords the pyrazole of Formula 50. Reaction of the pyrazole 50 with an alkylating agent of Formula 51 affords a mixture of pyrazoles of Formulae 52 and 53. This mixture of pyrazole isomers is readily separated by chromatographic methods and converted to the corresponding acids 4h and 4f, respectively. Preferred $R^{5d}$ substituents include alkyl and haloalkyl groups.

The synthesis of pyridinylpyrazole acids of Formula 4i, which are related to the preferred moiety J-10 wherein $R^5$ is a substituted 2-pyridinyl and attached to the 3-position of the pyrazole ring, as well as an alternative synthesis of Formula 4g, is depicted in Scheme 23. This synthesis is conducted according to the general synthesis described for Scheme 22.

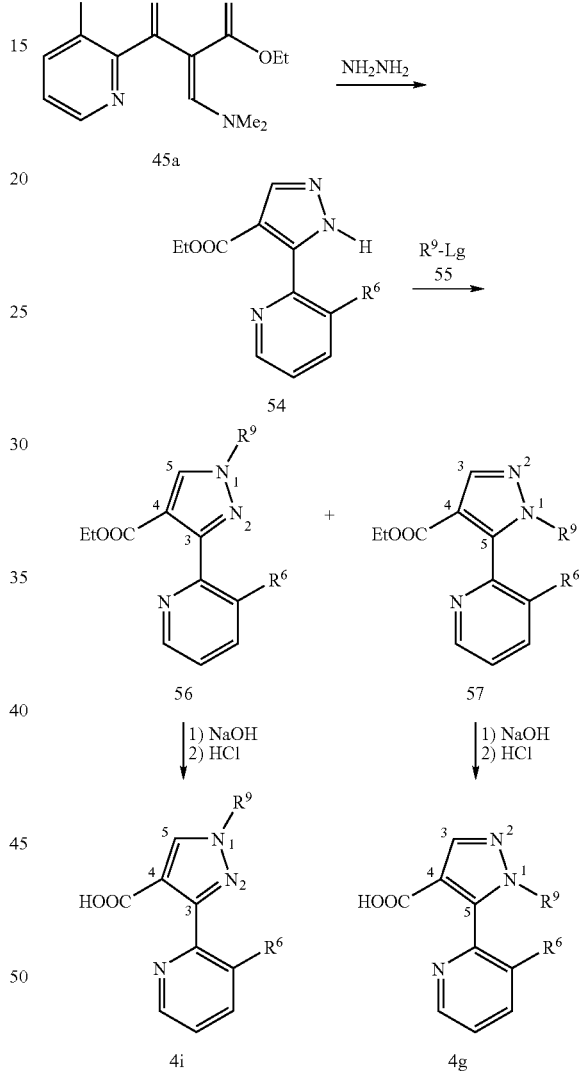

A general synthesis of pyrrole acids of Formula 4j is depicted in Scheme 24. Treatment of a compound of Formula 58 with 2,5-dimethoxytetrahydrofuran (59) affords a pyrrole of Formula 60. Formylation of the pyrrole 60 to provide the aldehyde of Formula 61 can be accomplished by using standard Vilsmeier-Haack formylation conditions, such as treatment With N,N-dimethylformamide (DMF) and phosphorus oxychloride. Halogenation of the compound of Formula 61 with N-halosuccinimides (NXS) such as N-chlorosuccinimide or N-bromosuccinimide occurs preferentially at the 4-position of the pyrrole ring. Oxidation of the halogenated aldehyde affords the pyrrole acid of Formula 4j.

The oxidation can be accomplished by using a variety of standard oxidation conditions.

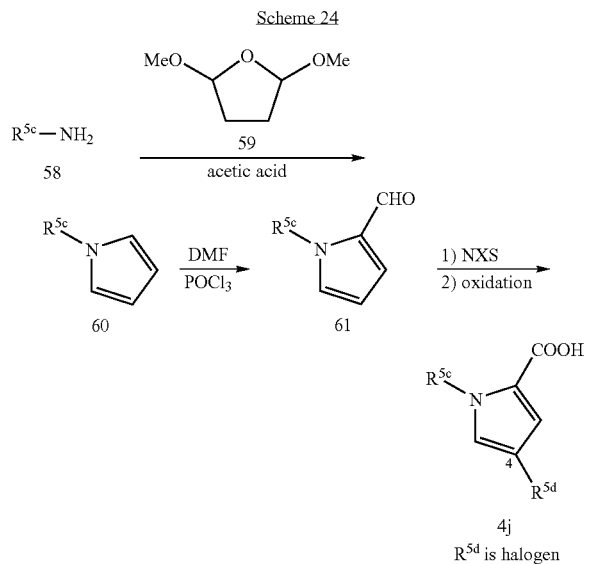

The synthesis of certain pyridinylpyrrole acids of Formula 4k, which are related to the preferred moiety J-11 wherein $R^5$ is a substituted 2-pyridinyl and attached to the nitrogen of the pyrrole ring, is depicted in Scheme 25. This synthesis is conducted according to the general synthesis described for Scheme 24. The compound of Formula 58a, 3-Chloro-2-aminopyridine, is a known compound (see *J. Heterocycl. Chem.* 1987, 24(5), 1313-16).

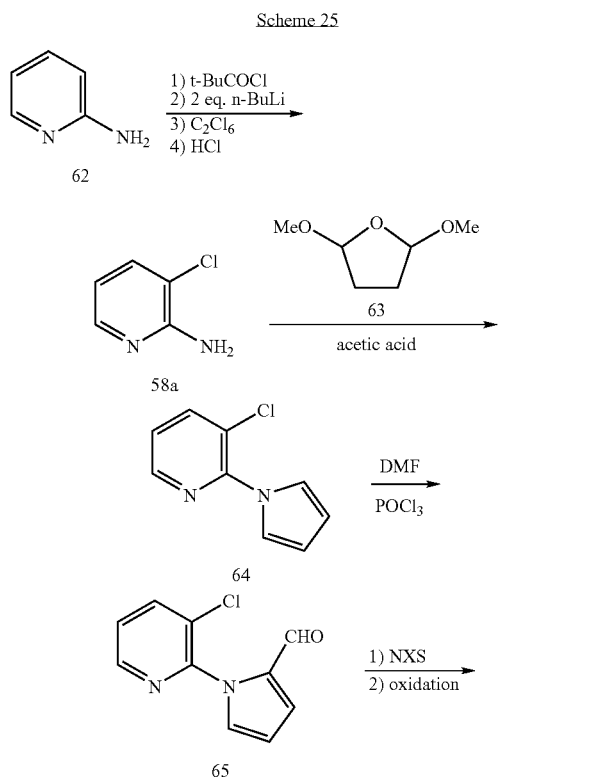

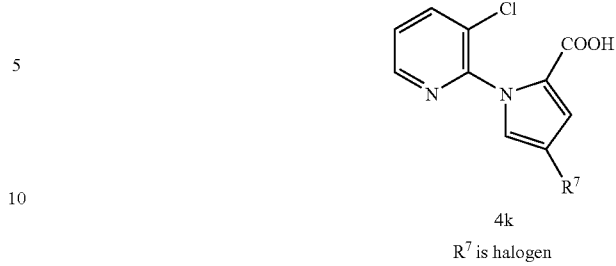

The synthesis of pyrrole acids of Formula 4m is depicted in Scheme 26. Cycloaddition of an allene of Formula 69 with a phenylsulfonyl hydrazide of Formula 68 (see Pavri, N. P.; Trudell, M. L. *J. Org. Chem.* 1997, 62, 2649-2651) affords a pyrroline of Formula 70. Treatment of the pyrroline of Formula 70 with tetrabutylammonium fluoride (TBAF) gives a pyrrole of Formula 71. Reaction of the pyrrole 71 with an alkylating agent $R^{5d}$-Lg (wherein Lg is a leaving group as defined above) followed by hydrolysis affords a pyrrole acid of Formula 4m.

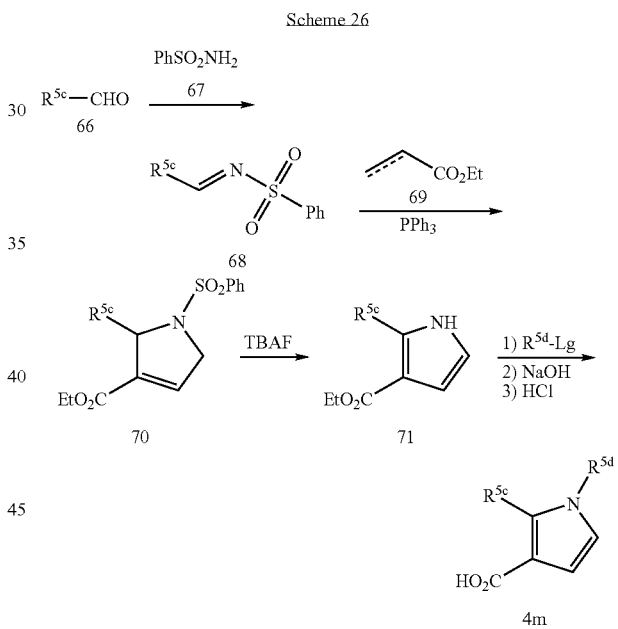

The synthesis of pyrrole acids of Formula 4n, which are related to the preferred moiety J-12 wherein $R^5$ is a substituted phenyl or a substituted 2-pyridyl and is attached to the 2-position of the pyrrole ring, is depicted in Scheme 27. The synthesis is conducted according to the general method described for Scheme 26.

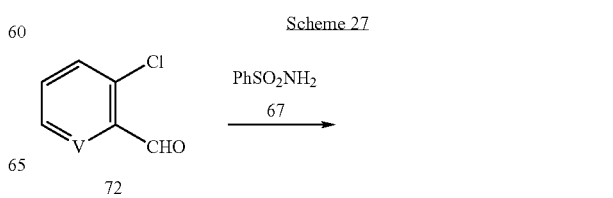

-continued

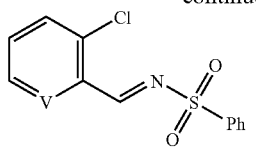 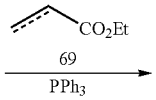
73

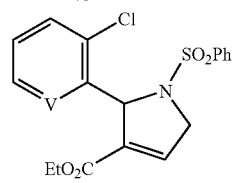 
74

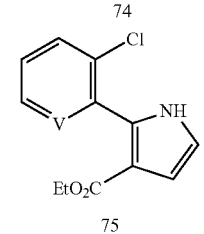 
75

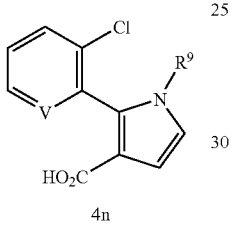
4n

The synthesis of pyrrole acids of Formula 4o is depicted in Scheme 28. Reaction of an α,β-unsaturated ester of Formula 76 with p-tolylsulfonylmethyl isocyanide (TosMIC) provides a pyrrole of Formula 78. For a leading reference, see Xu, Z. et al, *J. Org. Chem.,* 1988, 63, 5031-5041. Reaction of the pyrrole of Formula 78 with an alkylating agent $R^{5d}$-Lg (wherein Lg is a leaving group as defined above) followed by hydrolysis affords a pyrrole acid of Formula 4o.

Scheme 28

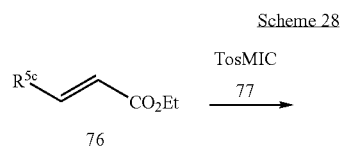
76

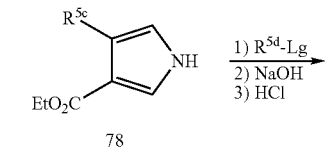
78

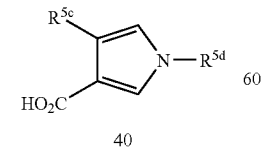
40

The synthesis of pyrrole acids of Formula 4p, which are related to the preferred moiety J-13, wherein $R^5$ is a substituted phenyl or a substituted 2-pyridinyl ring, is depicted in Scheme 29. The synthesis is conducted according to the general method described for Scheme 28.

Scheme 29

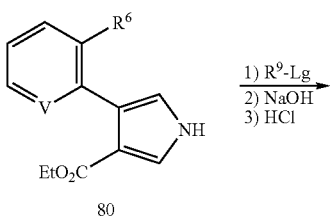 
79

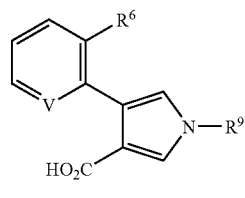
80

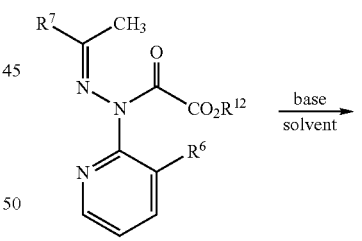
4p

Pyrazolecarboxylic acids of Formula 4q wherein $R^7$ is $CF_3$ can be prepared by the method outlined in Scheme 30.

Scheme 30

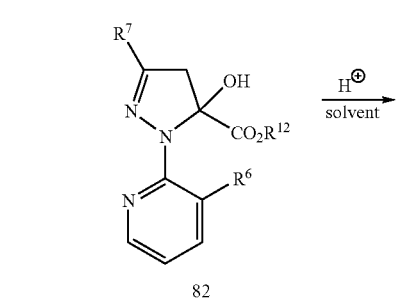
81
$R^{12}$ is $C_1$-$C_4$ alkyl

82

-continued

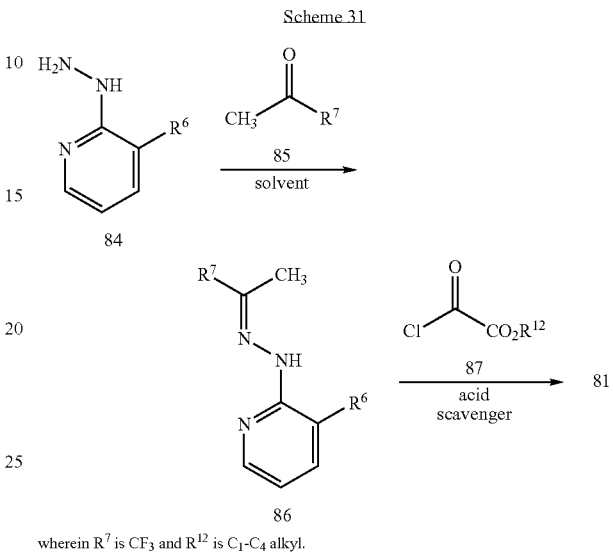

ester of acid conversion
83 $R^{13}$ is $C_1$-$C_4$ alkyl
4q $R^{13}$ is H

Reaction of a compound of Formula 81 wherein $R^{12}$ is $C_1$-$C_4$ alkyl with a suitable base in a suitable organic solvent affords the cyclized product of Formula 82 after neutralization with an acid such as acetic acid. The suitable base can be, for example but not limitation, sodium hydride, potassium t-butoxide, dimsyl sodium ($CH_3S(O)CH_2^-Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethylperhydro-1,3,2-diazaphosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 82 to give the compound of Formula 83, followed by converting the carboxylic ester function to carboxylic acid, affords the compound of Formula 4q. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C.). For the dehydration in the method of Scheme 30, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For the method of Scheme 30, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 4q. The carboxylic acid can be isolated by methods known to those skilled in the art, including crystallization, extraction and distillation.

Compounds of Formula 81 can be prepared by the method outlined in Scheme 31.

Scheme 31

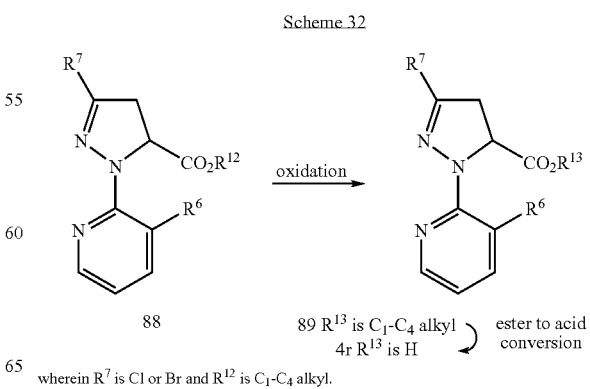

wherein $R^7$ is $CF_3$ and $R^{12}$ is $C_1$-$C_4$ alkyl.

Treatment of a hydrazine compound of Formula 84 with a ketone of Formula 85 in a solvent such as water, methanol or acetic acid gives the hydrazone of Formula 86. One skilled in the art will recognize that this reaction may require catalysis by an optional acid and may also require elevated temperatures depending on the molecular substitution pattern of the hydrazone of Formula 86. Reaction of the hydrazone of Formula 86 with the compound of Formula 87 in a suitable organic solvent such as, for example but not limitation, dichloromethane or tetrahydrofuran in the presence of an acid scavenger such as triethylamine provides the compound of Formula 81. The reaction is usually conducted at a temperature between about 0 and 100° C. Hydrazine compounds of Formula 84 can be prepared by standard methods, such as by contacting the corresponding halo compound of Formula 18a (Scheme 14) with hydrazine.

Pyrazolecarboxylic acids of Formula 4r wherein $R^7$ is Cl or Br can be prepared by the method outlined in Scheme 32.

Scheme 32

88 → oxidation → 89 $R^{13}$ is $C_1$-$C_4$ alkyl
4r $R^{13}$ is H
ester to acid conversion wherein $R^7$ is Cl or Br and $R^{12}$ is $C_1$-$C_4$ alkyl.

Oxidization of the compound of Formula 88 optionally in the presence of acid to give the compound of Formula 89 followed by conversion of the carboxylic ester function to the carboxylic acid provides the compound of Formula 4r. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 88 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfinic acid, phosphoric acid and the like, and organic acids, such as acetic acid, benzoic acid and the like. The acid, when used, should be used in greater than 0.1 equivalents versus the compound of Formula 88. To obtain complete conversion, one to five equivalents of acid can be used. The preferred oxidant is potassium persulfate and the oxidation is preferably carried out in the presence of sulfuric acid. The reaction can be carried out by mixing the compound of Formula 88 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 89 can be isolated by methods known to those skilled in the art, including crystallization, extraction and distillation. Methods suitable for converting the ester of Formula 89 to the carboxylic acid of Formula 4r are already described for Scheme 30.

Compounds of Formula 88 can be prepared from corresponding compounds of Formula 90 as shown in Scheme 33.

Scheme 33

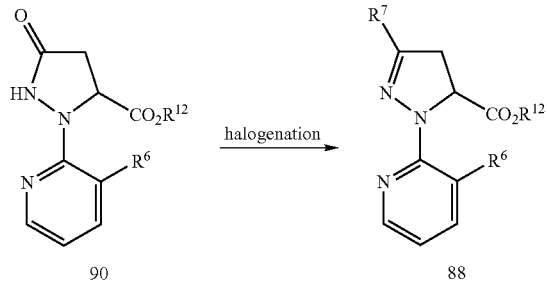

wherein $R^7$ is Cl or Br and $R^{12}$ is $C_1$-$C_4$ alkyl.

Treatment of a compound of Formula 90 with a halogenating reagent, usually in the presence of a solvent, affords the corresponding halo compound of Formula 88. Halogenating reagents that can be used include phosphorus oxyhalides, phosphorus trihalides, phosphorus pentahalides, thionyl chloride, dihalotrialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 90 should be used, preferably between about 0.33 and 1.2 equivalents. To obtain complete conversion, at least 0.20 equivalents of phosphorus pentahalide versus the compound of Formula 90 should be used, preferably between about 0.20 and 1.0 equivalents. Compounds of Formula 90 wherein $R^{12}$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 90 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than two hours. The reaction mass is then neutralized with an inorganic base, such as sodium bicarbonate, sodium hydroxide and the like, or an organic base, such as sodium acetate. The desired product, a compound of Formula 88, can be isolated by methods known to those skilled in the art, including crystallization, extraction and distillation.

Alternatively, compounds of Formula 88 wherein $R^7$ is Br or Cl can be prepared by treating the corresponding compounds of Formula 88 wherein $R^7$ is a different halogen (e.g., Cl for making Formula 88 wherein $R^7$ is Br) or a sulfonate group such as p-toluenesulfonate with hydrogen bromide or hydrogen chloride, respectively. By this method the $R^7$ halogen or sulfonate substituent on the Formula 88 starting compound is replaced with Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^7$ in the starting compound of Formula 88 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 88 wherein $R^7$ is Br) can facilitate the reaction. The product of Formula 88 is isolated by the usual methods known to those skilled in the art, including extraction, distillation and crystallization.

Starting compounds of Formula 88 wherein $R^7$ is Cl or Br can be prepared from corresponding compounds of Formula 90 as already described. Starting compounds of Formula 88 wherein $R^7$ is a sulfonate group can likewise be prepared from corresponding compounds of Formula 90 by standard methods such as treatment with a sulfonyl chloride (e.g., p-toluenesulfonyl chloride) and base such as a tertiary amine (e.g., triethylamine) in a suitable solvent such as dichloromethane.

Pyrazolecarboxylic acids of Formula 4s wherein $R^7$ is $OCH_2CF_3$ or Formula 4t wherein $R^7$ is $OCHF_2$ can be prepared by the method outlined in Scheme 34. In this method, instead of being halogenated as shown in Scheme 33, the compound of Formula 90 is oxidized to the compound of Formula 91. The reaction conditions for this oxidation are as already described for the conversion of the compound of Formula 88 to the compound of Formula 89 in Scheme 32.

The compound of Formula 91 is then alkylated to form the compound of Formula 93 ($R^7$ is $OCH_2CF_3$) by contact with an alkylating agent $CF_3CH_2Lg$ (92) in the presence of a base. In the alkylating agent 92, Lg is a nucleophilic reaction leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]-undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C.

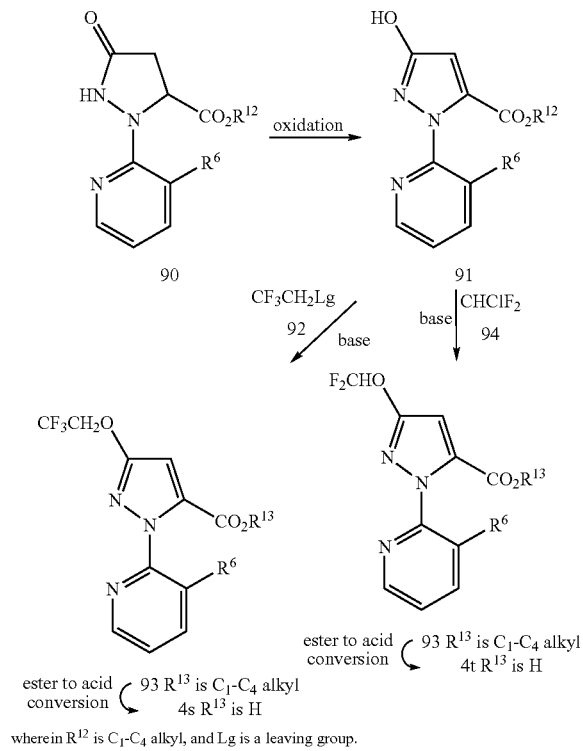

wherein $R^{12}$ is $C_1$-$C_4$ alkyl, and Lg is a leaving group.

The compound of Formula 91 can also be alkylated to form the compound of Formula 95 ($R^7$ is $OCHF_2$) by contact with difluorocarbene, prepared from $CHClF_2$ in the presence of a base. The reaction is generally conducted in a solvent, which can comprise ethers, such as tetrahydrofuran or dioxane, and polar aprotic solvents, such as acetonitrile, N,N-dimethylformamide, and the like. The base can be selected from inorganic bases such as potassium carbonate, sodium hydroxide or sodium hydride. Preferably the reaction is conducted using potassium carbonate with N,N-dimethylformamide as the solvent. The esters of Formula 93 or 95 can be isolated by conventional techniques such as extraction. The esters can then be converted to the carboxylic acids of Formula 4 or 4t by the methods already described for the conversion of Formula 83 to Formula 4q in Scheme 30.

As outlined in Scheme 35, compounds of Formula 90 can be prepared from compounds of Formula 84 (see Scheme 31).

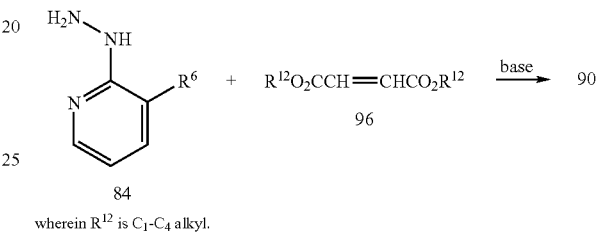

wherein $R^{12}$ is $C_1$-$C_4$ alkyl.

In this method, a hydrazine compound of Formula 84 is contacted with a compound of Formula 96 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 84 should be used, preferably between 0.9 and 1.3 equivalents. Greater than 1.0 equivalents of the compound of Formula 96 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 84 and the base in the solvent. The mixture can be heated or cooled to a desired temperature and the compound of Formula 96 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 84 and Formula 96. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —CO$_2$R$^{12}$ function on the compound of Formula 90 may be hydrolyzed to —CO$_2$H; for example, the presence of water in the reaction mixture can promote such hydrolysis. If the carboxylic acid (—CO$_2$H) is formed, it can be converted back to —CO$_2$R$^{12}$ wherein R$^{12}$ is C$_1$-C$_4$ alkyl using esterification methods well known in the art. The desired product, a compound of Formula 90, can be isolated by methods known to those skilled in the art, such as crystallization, extraction or distillation.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

It is believed that one skilled in the art using the preceding description can prepare compounds of Formula I of the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s means singlet, d means doublet, t means triplet, q means quartet, m means multiplet, dd means doublet of doublets, dt means doublet of triplets br s means broad singlet.

EXAMPLE 1

Preparation of N-[2-[1-(3-chloro-2-pyridinyl)-3-(trifluoromethyl)-1H-pyrazol-5-yl]-8-methyl-4H-3,1-benzoxazin-4-ylidene]-2-propanamine Step A: Preparation of 3-chloro-2-[3-(trifluoromethyl)-1H-pyrazol-1-yl]pyridine To a mixture of 2,3-dichloropyridine (99.0 g, 0.67 mol) and 3-trifluoromethyl pyrazole (83 g, 0.61 mol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the desired intermediate as a clear yellow oil (113.4 g).

$^1$H NMR (CDCl$_3$): δ 6.78 (s,1H), 7.36 (t,1H), 7.93 (d,1H), 8.15 (s,1H), 8.45 (d,1H).

Step B: Preparation of 1-(3-chloro-2-pyridinyl)-3-(trifluoromethyl)-1H-pyrazole-5-carboxylic Acid To a solution of the pyrazole product from Step A (105.0 g, 425 mmol) in dry tetrahydrofuran (700 mL) at -75° C. was added via cannula a -30° C. solution of lithium diisopropylamide (425 mmol) in dry tetrahydrofuran (300 mL). The deep red solution was stirred for 15 minutes, after which time carbon dioxide was bubbled through at -63° C. until the solution became pale yellow and the exothermicity ceased. The reaction was stirred for an additional 20 minutes and then quenched with water (20 mL). The solvent was removed under reduced pressure, and the reaction mixture partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional acid was added to lower the pH to 2.5-3. The orange oil congealed into a granular solid, which was filtered, washed successively with water and 1N hydrochloric acid, and dried under vacuum at 50° C. to afford the title product as an off-white solid (130 g). (Product from another run following similar procedures melted at 175-176° C.)

$^1$H NMR (DMSO-d$_6$): δ 7.61 (s,1H), 7.76 (dd,1H), 8.31 (d,1H), 8.60 (d,1H).

Step C: Preparation of 8-methyl-2H-3,1-benzoxazine-2,4(1H)-dione

To a solution of 2-amino-3-methylbenzoic acid (6 g) in dry 1,4-dioxane (50 mL) was added dropwise a solution of trichloromethyl chloroformate (8 mL) in dry 1,4-dioxane (25 mL), with ice-water cooling to keep the reaction temperature below 25° C. A white precipitate began to form during the addition. The reaction mixture was stirred at room temperature overnight. The precipitated solids were removed by filtration and washed with 1,4-dioxane (2×20 mL) and hexane (2×15 mL) and air-dried to yield 6.51 g of off-white solid.

$^1$H NMR (DMSO-d$_6$) δ 2.33 (s,3H), 7.18 (t,1H), 7.59 (d,1H), 7.78 (d,1H), 11.0 (br s,1H).

Step D: Preparation of 1-(3-chloro-2-pyridinyl-N-[2-methyl-6-[[(1-methylethyl)amino]carbonyl]phenyl]-3-(trifluoromethyl)-1H-pyrazole-5-carboxamide To a solution of the carboxylic acid product prepared as in Step B (28 g, 96 mmol) in dichloromethane (240 mL) was added N,N-dimethylformamide (12 drops) and oxalyl chloride (15.8 g, 124 mmol). The reaction mixture was stirred at room temperature until gas evolution ceased (approximately 1.5 hours). The reaction mixture was concentrated in vacuo to provide the crude acid chloride as an oil that was used without further purification. The crude acid chloride was dissolved in acetonitrile (95 mL) and added to a solution of the benzoxazin-2,4-dione prepared as in Step C in acetonitrile (95 mL). The resulting mixture was stirred at room temperature (approximately 30 minutes). Pyridine (95 mL) was added and the mixture heated to about 90° C. (approximately 1 hour). The reaction mixture was cooled to about 35° C. and isopropylamine (25 mL) was added. The reaction mixture exothermically warmed during the addition and then was maintained at about 50° C. (approximately 1 hour). The reaction mixture was then poured into ice water and stirred. The resulting precipitate was collected by filtration, washed with water and dried in vacuo overnight to provide 37.5 g of the title compound as a tan solid.

$^1$H NMR (CDCl$_3$): δ 1.23 (d,6H), 2.21 (s,3H), 4.2 (m,1H), 5.9 (d,1H), 7.2 (t,1H), 7.3 (m,2H), 7.31 (s,1H), 7.4 (m,1H), 7.8 (d,1H), 8.5 (d,1H), 10.4 (s,1H).

Step E: Preparation of N-[2-[1-(3-chloro-2-pyridinyl)-3-(trifluoromethyl)-1H-pyrazol-5-yl]-8-methyl-4H-3,1-benzoxazin-4-ylidene]-2-propanamine A stirred solution of the title compound from Step D (1.2 g, 2.6 mmol) in 8 mL of phosphorous oxychloride was heated at reflux for 8 hours. The hot reaction solution was poured onto a large excess of ice and 100 ml of ethyl acetate added almost immediately (before allowing all of the ice to melt). After stirring and allowing the remaining ice to melt, the ethyl acetate layer was separated, washed with water, aqueous saturated sodium bicarbonate and brine. Followed by drying over magnesium sulfate, the solvent was removed in vacuo to give a crude yellow oily solid residue. Purification by flash chromatography on silica gel (4:1 hexane/ ethyl acetate as eluant) afforded 450 mg of the title compound, a compound of the invention, isolated as a white solid melting at 175-176° C.

$^1$H N NMR (CDCl$_3$): δ 1.23 (d, 6H), 1.75 (s, 3H), 4.07 (m, 1H), 7.15-7.28 (m, 3H), 7.45 (m, 1H), 7.90 (d, 1H), 7.95 (d, 1H), 8.55 (d, 1H).

EXAMPLE 2

Preparation of N-[2-[1-(2-chlorophenyl)-3-(trifluoromethyl)-1H-pyrazol-5-yl]-8-methyl-4H-3,1-benzoxazin-4-ylidene]-2-propanamine Step A: Preparation of 1-(2-chlorophenyl)-5-(2-furanyl)-3-(trifluoromethyl)-1H-pyrazole To a solution of 1-(2-furyl)-4,4,4-trifluorobutane-1,3-dione (105 g, 0.51 mole) in glacial acetic acid (220 mL) was added sodium acetate (42 g 0.51 mole). The temperature rose to about 34° C. 2-Chlorophenylhydrazine hydrochloride (90 g, 0.5 mole) was added portionwise over a period of 10 minutes to give a creamy suspension. The mixture was warmed to about 60° C. for about 45 minutes. The bulk of the acetic acid was removed by stripping on a rotary evaporator at a bath temperature of 65° C. The remaining oily residue was added to about 800 ml of water with vigorous stirring and a heterogeneous mixture resulted. After about 15 minutes, dichloromethane (500 mL) was added and the mixture was partitioned. The aqueous phase was extracted with 300 ml of dichloromethane. The combined organic phases were washed with water and saturated sodium bicarbonate solution and then dried with MgSO$_4$ and filtered. Volatiles were removed on a rotary evaporator. The crude product consisted of 151 g of a dark red oil, which contained approximately 89% of the desired product and 11% of the regioisomeric pyrazole (determined by NMR analysis).

Step B: Preparation of 1-(2-chlorophenyl)-3-(trifluoromethyl)-1H-pyrazole-5-carboxylic Acid A sample of the crude product from Step A (approximately 89%, 56.0 g, 0.18 mole) was dissolved in acetonitrile (400 mL) and a solution of NaH$_2$PO$_4$ (120 g, 0.87 mole) in 520 mL of water was added. Sodium hypochlorite solution (5.25% in water, 128 g, 2.6 mole) was added dropwise over 10-15 minutes. The orange solution was maintained at room temperature for 30 minutes. The reaction mixture was cooled in an ice bath and a solution of NaClO$_2$ in 560 mL of water was added dropwise, keeping the temperature below 11° C. Gas evolution was observed and an aqueous sodium hydroxide scrubber was used to quench evolved chlorine. After the addition was complete, the reaction mixture was kept cold for one hour then allowed to reach room temperature overnight. To the reaction mixture was added 80 mL of concentrated hydrochloric acid dropwise to bring the pH below 3. The reaction mixture was extracted twice with ethyl acetate and the combined organic extracts were added dropwise rapidly with stirring to a cooled (<15° C.) solution of 300 g of NAHSO$_3$ in 1-300 mL of water. The mixture was partitioned and the aqueous phase extracted with ethyl acetate. The combined organic phases were washed with saturated brine, dried (MgSO$_4$), filtered and concentrated in vacuo. The residue was taken up in chlorobutane and reconcentrated (twice). The resulting brown solid was triturated in 100 mL of ethyl ether in hexane (1%). Small portions of chlorobutane were added to help granulate the solid. The product was collected via filtration, washed with hexanes and dried. The product consisted of 40.8 g of tan solid, which was essentially pure based upon $^1$H NMR.

Step C: Preparation of 1-(2-chlorophenyl)-3-(trifluoromethyl)-1H-pyrazole-5-carbonyl chloride A sample of crude 1-(2-chlorophenyl)-3-(trifluoromethyl)-1H-pyrazole-5-carboxylic acid (40.8 g, 0.14 mole) was dissolved in methylene chloride (300 mL). The solution was treated with oxalyl chloride (15.7 mL, 0.18 mole), followed by N,N-dimethylformamide (12 drops). Off-gassing began shortly after adding the N,N-dimethylformamide catalyst. The reaction mixture was stirred for about 20 minutes under ambient conditions, then was heated to reflux for a period of 35 minutes. Volatiles were removed by concentrating the reaction mixture on a rotary evaporator at a bath temperature of 55° C. The crude product, approximately 43 g of a light-yellow oil, was used directly in the next step.

Step D: Preparation of 1-(2-chlorophenyl)-N-[2-methyl-6-[[(1-methylethyl)amino]carbonyl]phenyl]-3-(trifluoromethyl)-1H-pyrazole-5-carboxamide To a sample of the title compound of Example 1, Step C (22.3 g, 0.126 mole), suspended in acetonitrile (100 mL) was added crude 1-(2-chlorophenyl)-3-(trifluoromethyl)-1H-pyrazole-5-carbonyl chloride (43 g). The mixture was diluted with 350 mL of pyridine and heated to approximately 95° C. for a period of 2 hours. The mixture was cooled to 29° C., then was treated with isopropylamine (32.2 mL, 0.38 mole). The reaction mass self-heated to 60° C. and was maintained at about 50° C. for one hour, then stirred overnight. The reaction mixture was poured into 1 L of water and stirred. The resulting solid was collected by filtration and washed with water. The wet cake was taken up in a mixture of dichloromethane and methanol, the water removed, and the organic phase was dried with molecular sieves and filtered. Volatiles were removed on a rotary evaporator. The crude product was triturated with 1:1 ether/ hexane, collected by filtration and washed with hexanes to yield 42.6 g of a light tan solid melting at 230-231° C.

$^1$H NMR (DMSO-d$_6$) δ 10.3 (s,1H), 7.1-7.5 (m,8H), 5.9 (d,1H), 4.2 (m,1H), 2.21 (s,3H), 1.21 (d,6H).

Step E Preparation of N-[2-[1-(2-chlorophenyl)-3-(trifluoromethyl)-1H-pyrazol-5-yl]-8-methyl-4H-3,1-benzoxazin-4-ylidene]-2-propanamine To the title compound of Step D (1.2 g, 2.7 mmol) dissolved in 8 mL of dichloromethane, 5 mL of thionyl chloride was added and the solution heated at reflux for 8 hours. The solvent was removed in vacuo and remaining residue partitioned between 70 mL of ethyl acetate and water. The organic layer was separated, washed with water, saturated aqueous sodium bicarbonate and brine. The organic phase was dried over magnesium sulfate and the solvent was removed in vacuo to give a crude oily solid residue. Purification by flash chromatography on silica gel (2:1 hexane/ethyl acetate) and filtering from hexane afforded 700 mg of the title compound, a compound of the invention, isolated as a white solid melting at 133-135° C.

$^1$H NMR (CDCl$_3$): δ 7.90 (d, 1H), 7.57-7.43 (m, 4H), 7.30-7.13 (m, 3H), 4.0 (m, 1H), 1.80 (s, 3H), 1.21 (d, 6H).

EXAMPLE 3

Preparation of 7,9-Dichloro-5-[1-(3-chloro-2-pyridinyl)-3-(trifluoromethyl)-1H-pyrazol-5-yl]-2,3-dihydroimidazo[1,2-c]quinazoline

Step A: Preparation of 2,4-Dichloro-6-(4,5-dihydro-1H-imidazol-2-yl)benzenamine To a solution of ethylene diamine (1.2 mL, 18 mmol) in ethyl ether (50 mL) at −20° C. was added n-butyl lithium (6.4 mL, 2.5 M in hexanes, 16 mmol). The mixture was stirred at 0° C. for 0.3 hour before the addition of 2,4-dichloro-6-trifluoromethyl aniline (0.92 g, 4.2 mmol). The mixture was stirred at 0° C. for an additional 1.5 hours, at which point water (0.36 mL, 20 mmol) was added and the solvent was removed under reduced pressure. Purification by flash column chromatography (silica gel, 1% to 10% methanol in dichloromethane) to give the title compound of Step A (0.35 g) as a yellow solid.

$^1$H NMR (CDCl$_3$) δ 7.30 (d,1H), 7.23 (d,1H), 6.8 (bs,2H), 4.7-4.6 (bs,1H), 3.77 (bs,4H).

Step B: Preparation of 7,9-Dichloro-5-[1-(3-chloro-2-pyridinyl)-3-(trifluoromethyl)-1H-pyrazol-5-yl]-2,3-dihydroimidazo[1,2-c]quinazoline To a solution of 1-(3-chloro-2-pyridinyl)-3-(trifluoromethyl)-1H-pyrazole-5-carboxylic acid (0.6 g, 2.02 mol) (see Example 1, Step B) in dichloromethane (10 mL) containing dimethylformamide (1 drop) was added oxalyl chloride (198 μL, 2.22 mmol). The mixture was stirred at ambient temperature for two hours before being concentrated under reduced pressure and redissolved in dichloromethane (5 mL). Seven tenths of this solution was added to a solution of the title compound of Step A (0.3 g, 1.3 mmol), triethylamine (272 mL, 1.95 mmol) and dimethylaminopyridine (16 mg, 0.13 mmol) in dichloromethane (5 mL) and the mixture was stirred at ambient temperature overnight. A saturated solution of sodium bicarbonate was then added and the mixture was filtered through a column of Celite®. Concentration of the filtrate provided material that was purified using flash column chromatography (silica gel, 1% then 2% then 5% methanol in dichloromethane then again in 10% then 20% acetone in chloroform then 5% methanol in dichloromethane). Isolation of the first-eluting material gave the title compound of Example 3, a compound of the invention, as a yellow solid (62 mg). A second-eluting material (31 mg) was 1-(3-Chloro-2-pyridinyl)-N-[2,4-dichloro-6-(4,5-dihydro-1H-imidazol-2-yl)phenyl]-3-(trifluoromethyl)-1H-pyrazole-5-carboxamide, the precursor to Example 3.

$^1$H NMR (CDCl$_3$) δ 8.5-8.4 (d,1H), 7.9 (d,1H), 7.46 (d,1H), 7.41 (d,1H), 7.4 (dd,1H), 7.31 (s,1H), 3.77 (s,4H).

By the procedures described herein together with methods known in the art, the following compounds of Tables 1-21 can be prepared. The following abbreviations are used in the Tables which follow: t means tertiary, s means secondary, n means normal, i means iso, Me means methyl, Et means ethyl, Pr means propyl, i-Pr means isopropyl, and Bu means butyl.

TABLE 1

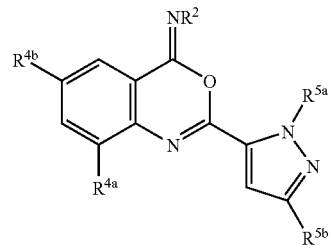

| R$^2$ | R$^{4a}$ | R$^{4b}$ | R$^{5a}$ |
|---|---|---|---|
| R$^{5b}$ is CF$_3$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R$^{5b}$ is OCF$_3$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |

TABLE 1-continued

| R² | R⁴ᵃ | R⁴ᵇ | R⁵ᵃ |
|---|---|---|---|
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R⁵ᵇ is CF(CF₃)₂ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |

TABLE 2

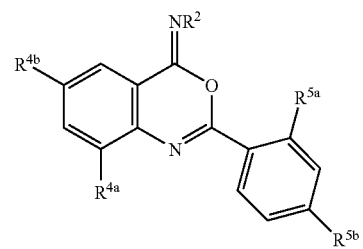

| R² | R⁴ᵃ | R⁴ᵇ | R⁵ᵃ |
|---|---|---|---|
| R⁵ᵇ is CF₃ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |

TABLE 2-continued

| R² | R⁴ᵃ | R⁴ᵇ | R⁵ᵃ |
|---|---|---|---|
| R⁵ᵇ is OCF₃ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R⁵ᵇ is CF(CF₃)₂ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |

TABLE 3

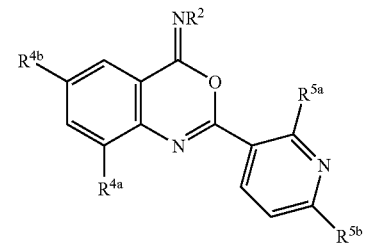

| R² | R⁴ᵃ | R⁴ᵇ | R⁵ᵃ |
|---|---|---|---|
| R⁵ᵇ is CF₃ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |

TABLE 3-continued

| | | | |
|---|---|---|---|
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| $R^{5b}$ is $OCF_3$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| $R^{5b}$ is $CF(CF_3)_2$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |

TABLE 4

| $R^2$ | $R^{4a}$ | $R^{4b}$ | $R^{5a}$ |
|---|---|---|---|
| $R^{5b}$ is $CF_3$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| $R^{5b}$ is $OCF_3$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| $R^{5b}$ is $CF(CF_3)_2$ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |

TABLE 4-continued

| | | | |
|---|---|---|---|
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |

TABLE 5

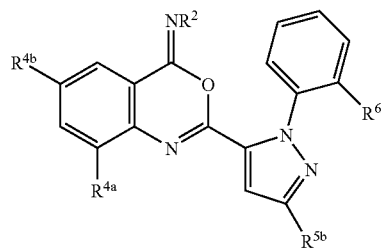

| $R^2$ | $R^{4a}$ | $R^{4b}$ | $R^5$ | $R^6$ |
|---|---|---|---|---|
| Me | $CH_3$ | H | $CF_3$ | Cl |
| Et | $CH_3$ | H | $CF_3$ | Cl |
| i-Pr | $CH_3$ | H | $CF_3$ | Cl |
| t-Bu | $CH_3$ | H | $CF_3$ | Cl |
| Me | $CH_3$ | H | $CF_3$ | Br |
| Et | $CH_3$ | H | $CF_3$ | Br |
| i-Pr | $CH_3$ | H | $CF_3$ | Br |
| t-Bu | $CH_3$ | H | $CF_3$ | Br |
| Me | $CH_3$ | H | Cl | Cl |
| Et | $CH_3$ | H | Cl | Cl |
| i-Pr | $CH_3$ | H | Cl | Cl |
| t-Bu | $CH_3$ | H | Cl | Cl |
| Me | $CH_3$ | H | Cl | Br |
| Et | $CH_3$ | H | Cl | Br |
| i-Pr | $CH_3$ | H | Cl | Br |
| t-Bu | $CH_3$ | H | Cl | Br |
| Me | $CH_3$ | H | Br | Cl |
| Et | $CH_3$ | H | Br | Cl |
| i-Pr | $CH_3$ | H | Br | Cl |
| t-Bu | $CH_3$ | H | Br | Cl |
| Me | $CH_3$ | H | Br | Br |
| Et | $CH_3$ | H | Br | Br |
| i-Pr | $CH_3$ | H | Br | Br |
| t-Bu | $CH_3$ | H | Br | Br |
| Me | $CH_3$ | F | $CF_3$ | Cl |
| Et | $CH_3$ | F | $CF_3$ | Cl |
| i-Pr | $CH_3$ | F | $CF_3$ | Cl |
| t-Bu | $CH_3$ | F | $CF_3$ | Cl |
| Me | $CH_3$ | F | $CF_3$ | Br |
| Et | $CH_3$ | F | $CF_3$ | Br |
| i-Pr | $CH_3$ | F | $CF_3$ | Br |
| t-Bu | $CH_3$ | F | $CF_3$ | Br |
| Me | $CH_3$ | F | Cl | Cl |
| Et | $CH_3$ | F | Cl | Cl |
| i-Pr | $CH_3$ | F | Cl | Cl |
| t-Bu | $CH_3$ | F | Cl | Cl |
| Me | $CH_3$ | F | Cl | Br |
| Et | $CH_3$ | F | Cl | Br |
| i-Pr | $CH_3$ | F | Cl | Br |
| t-Bu | $CH_3$ | F | Cl | Br |
| Me | $CH_3$ | F | Br | Cl |
| Et | $CH_3$ | F | Br | Cl |
| i-Pr | $CH_3$ | F | Br | Cl |
| t-Bu | $CH_3$ | F | Br | Cl |
| Me | $CH_3$ | F | Br | Br |
| Et | $CH_3$ | F | Br | Br |
| i-Pr | $CH_3$ | F | Br | Br |
| t-Bu | $CH_3$ | F | Br | Br |
| Me | $CH_3$ | Br | $CF_3$ | Cl |
| Et | $CH_3$ | Br | $CF_3$ | Cl |
| i-Pr | $CH_3$ | Br | $CF_3$ | Cl |
| t-Bu | $CH_3$ | Br | $CF_3$ | Cl |
| Me | $CH_3$ | Br | $CF_3$ | Br |
| Et | $CH_3$ | Br | $CF_3$ | Br |
| i-Pr | $CH_3$ | Br | $CF_3$ | Br |
| t-Bu | $CH_3$ | Br | $CF_3$ | Br |
| Me | $CH_3$ | Br | Cl | Cl |
| Et | $CH_3$ | Br | Cl | Cl |
| i-Pr | $CH_3$ | Br | Cl | Cl |
| t-Bu | $CH_3$ | Br | Cl | Cl |
| Me | $CH_3$ | Br | Cl | Br |
| Et | $CH_3$ | Br | Cl | Br |
| i-Pr | $CH_3$ | Br | Cl | Br |
| t-Bu | $CH_3$ | Br | Cl | Br |
| Me | $CH_3$ | Br | Br | Cl |
| Et | $CH_3$ | Br | Br | Cl |
| i-Pr | $CH_3$ | Br | Br | Cl |
| t-Bu | $CH_3$ | Br | Br | Cl |
| Me | $CH_3$ | Br | Br | Br |
| Et | $CH_3$ | Br | Br | Br |
| i-Pr | $CH_3$ | Br | Br | Br |
| t-Bu | $CH_3$ | Br | Br | Br |
| Me | $CH_3$ | I | $CF_3$ | Cl |
| Et | $CH_3$ | I | $CF_3$ | Cl |
| i-Pr | $CH_3$ | I | $CF_3$ | Cl |
| t-Bu | $CH_3$ | I | $CF_3$ | Cl |
| Me | $CH_3$ | I | $CF_3$ | Br |
| Et | $CH_3$ | I | $CF_3$ | Br |
| i-Pr | $CH_3$ | I | $CF_3$ | Br |
| t-Bu | $CH_3$ | I | $CF_3$ | Br |
| Me | $CH_3$ | I | Cl | Cl |
| Et | $CH_3$ | I | Cl | Cl |
| i-Pr | $CH_3$ | I | Cl | Cl |
| t-Bu | $CH_3$ | I | Cl | Cl |
| Me | $CH_3$ | I | Cl | Br |
| Et | $CH_3$ | I | Cl | Br |
| i-Pr | $CH_3$ | I | Cl | Br |
| t-Bu | $CH_3$ | I | Cl | Br |
| Me | $CH_3$ | I | Br | Cl |
| Et | $CH_3$ | I | Br | Cl |
| i-Pr | $CH_3$ | I | Br | Cl |
| t-Bu | $CH_3$ | I | Br | Cl |
| Me | $CH_3$ | I | Br | Br |
| Et | $CH_3$ | I | Br | Br |
| i-Pr | $CH_3$ | I | Br | Br |
| t-Bu | $CH_3$ | I | Br | Br |
| Me | $CH_3$ | $CF_3$ | $CF_3$ | Cl |
| Et | $CH_3$ | $CF_3$ | $CF_3$ | Cl |
| i-Pr | $CH_3$ | $CF_3$ | $CF_3$ | Cl |
| t-Bu | $CH_3$ | $CF_3$ | $CF_3$ | Cl |
| Me | $CH_3$ | $CF_3$ | $CF_3$ | Br |
| Et | $CH_3$ | $CF_3$ | $CF_3$ | Br |
| i-Pr | $CH_3$ | $CF_3$ | $CF_3$ | Br |
| t-Bu | $CH_3$ | $CF_3$ | $CF_3$ | Br |
| Me | $CH_3$ | $CF_3$ | Cl | Cl |
| Et | $CH_3$ | $CF_3$ | Cl | Cl |
| i-Pr | $CH_3$ | $CF_3$ | Cl | Cl |
| t-Bu | $CH_3$ | $CF_3$ | Cl | Cl |
| Me | $CH_3$ | $CF_3$ | Cl | Br |

TABLE 5-continued

| $R^2$ | $R^{4a}$ | $R^{4b}$ | $R^5$ | $R^6$ |
|---|---|---|---|---|
| Et | $CH_3$ | F | Br | Br |
| i-Pr | $CH_3$ | F | Br | Br |
| t-Bu | $CH_3$ | F | Br | Br |
| Me | $CH_3$ | Br | $CF_3$ | Cl |
| Et | $CH_3$ | Br | $CF_3$ | Cl |
| i-Pr | $CH_3$ | Br | $CF_3$ | Cl |
| t-Bu | $CH_3$ | Br | $CF_3$ | Cl |
| Me | $CH_3$ | Br | $CF_3$ | Br |
| Et | $CH_3$ | Br | $CF_3$ | Br |
| i-Pr | $CH_3$ | Br | $CF_3$ | Br |
| t-Bu | $CH_3$ | Br | $CF_3$ | Br |
| Me | $CH_3$ | Br | Cl | Cl |
| Et | $CH_3$ | Br | Cl | Cl |
| i-Pr | $CH_3$ | Br | Cl | Cl |
| t-Bu | $CH_3$ | Br | Cl | Cl |
| Me | $CH_3$ | Br | Cl | Br |
| Et | $CH_3$ | Br | Cl | Br |
| i-Pr | $CH_3$ | Br | Cl | Br |
| t-Bu | $CH_3$ | Br | Cl | Br |
| Me | $CH_3$ | Br | Br | Cl |
| Et | $CH_3$ | Br | Br | Cl |
| i-Pr | $CH_3$ | Br | Br | Cl |
| t-Bu | $CH_3$ | Br | Br | Cl |
| Me | $CH_3$ | Br | Br | Br |
| Et | $CH_3$ | Br | Br | Br |
| i-Pr | $CH_3$ | Br | Br | Br |
| t-Bu | $CH_3$ | Br | Br | Br |
| Me | $CH_3$ | I | $CF_3$ | Cl |
| Et | $CH_3$ | I | $CF_3$ | Cl |
| i-Pr | $CH_3$ | I | $CF_3$ | Cl |
| t-Bu | $CH_3$ | I | $CF_3$ | Cl |
| Me | $CH_3$ | I | $CF_3$ | Br |
| Et | $CH_3$ | I | $CF_3$ | Br |
| i-Pr | $CH_3$ | I | $CF_3$ | Br |
| t-Bu | $CH_3$ | I | $CF_3$ | Br |
| Me | $CH_3$ | I | Cl | Cl |
| Et | $CH_3$ | I | Cl | Cl |
| i-Pr | $CH_3$ | I | Cl | Cl |
| t-Bu | $CH_3$ | I | Cl | Cl |
| Me | $CH_3$ | I | Cl | Br |
| Et | $CH_3$ | I | Cl | Br |
| i-Pr | $CH_3$ | I | Cl | Br |
| t-Bu | $CH_3$ | I | Cl | Br |
| Me | $CH_3$ | I | Br | Cl |
| Et | $CH_3$ | I | Br | Cl |
| i-Pr | $CH_3$ | I | Br | Cl |
| t-Bu | $CH_3$ | I | Br | Cl |
| Me | $CH_3$ | I | Br | Br |
| Et | $CH_3$ | I | Br | Br |
| i-Pr | $CH_3$ | I | Br | Br |
| t-Bu | $CH_3$ | I | Br | Br |
| Me | $CH_3$ | $CF_3$ | $CF_3$ | Cl |
| Et | $CH_3$ | $CF_3$ | $CF_3$ | Cl |
| i-Pr | $CH_3$ | $CF_3$ | $CF_3$ | Cl |
| t-Bu | $CH_3$ | $CF_3$ | $CF_3$ | Cl |
| Me | $CH_3$ | $CF_3$ | $CF_3$ | Br |
| Et | $CH_3$ | $CF_3$ | $CF_3$ | Br |
| i-Pr | $CH_3$ | $CF_3$ | $CF_3$ | Br |
| t-Bu | $CH_3$ | $CF_3$ | $CF_3$ | Br |
| Me | $CH_3$ | $CF_3$ | Cl | Cl |
| Et | $CH_3$ | $CF_3$ | Cl | Cl |
| i-Pr | $CH_3$ | $CF_3$ | Cl | Cl |
| t-Bu | $CH_3$ | $CF_3$ | Cl | Cl |
| Me | $CH_3$ | $CF_3$ | Cl | Br |

TABLE 5-continued

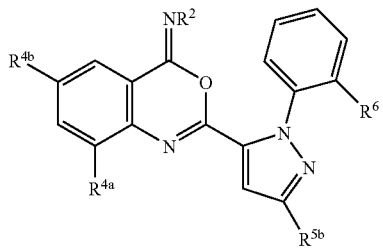

| R² | R⁴ᵃ | R⁴ᵇ | R⁵ | R⁶ |
|---|---|---|---|---|
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| Me | CH₃ | CF₃ | Br | Br |
| Et | CH₃ | CF₃ | Br | Br |
| i-Pr | CH₃ | CF₃ | Br | Br |
| t-Bu | CH₃ | CF₃ | Br | Br |
| n-Pr | CH₃ | Cl | Cl | Cl |
| n-Bu | CH₃ | Cl | Cl | Cl |
| s-Bu | CH₃ | Cl | Cl | Cl |
| i-Bu | CH₃ | Cl | Cl | Cl |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| t-Bu | Cl | H | Cl | Cl |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |

TABLE 5-continued

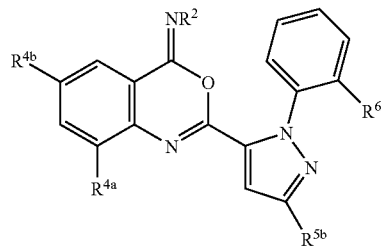

| R² | R⁴ᵃ | R⁴ᵇ | R⁵ | R⁶ |
|---|---|---|---|---|
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |

TABLE 5-continued

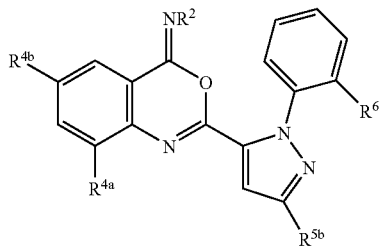

| R² | R⁴ᵃ | R⁴ᵇ | R⁵ | R⁶ |
|---|---|---|---|---|
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Cl | Br | Cl | Cl |
| Et | Cl | Br | Cl | Cl |
| i-Pr | Cl | Br | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| t-Bu | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |

TABLE 5-continued

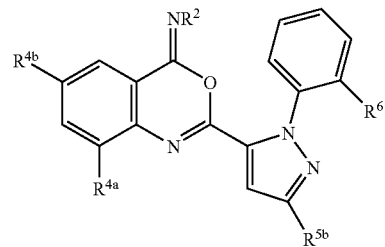

| R² | R⁴ᵃ | R⁴ᵇ | R⁵ | R⁶ |
|---|---|---|---|---|
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |

TABLE 5-continued

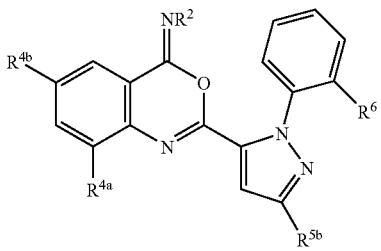

| R² | R⁴ᵃ | R⁴ᵇ | R⁵ | R⁶ |
|---|---|---|---|---|
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| Me | Br | Br | CF₃ | Cl |
| Et | Br | Br | CF₃ | Cl |
| i-Pr | Br | Br | CF₃ | Cl |
| t-Bu | Br | Br | CF₃ | Cl |
| Me | Br | Br | CF₃ | Br |
| Et | Br | Br | CF₃ | Br |
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| t-Bu | Cl | Br | CF₃ | Br |
| t-Bu | Cl | Br | Cl | Cl |

TABLE 6

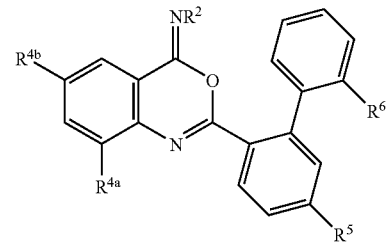

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |

TABLE 6-continued

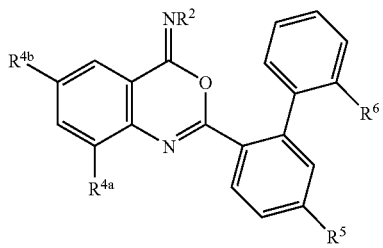

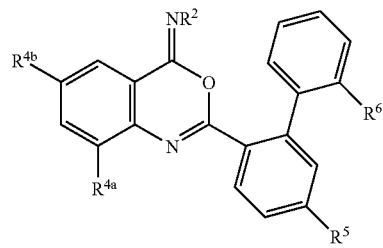

| $R^2$ | $R^{4a}$ | $R^{4b}$ | $R^5$ | $R^6$ | | $R^2$ | $R^{4a}$ | $R^{4b}$ | $R^5$ | $R^6$ |
|---|---|---|---|---|---|---|---|---|---|---|
| Me | CH₃ | Br | Br | Cl | | Me | Cl | Cl | Br | Br |
| Et | CH₃ | Br | Br | Cl | | Et | Cl | Cl | Br | Br |
| i-Pr | CH₃ | Br | Br | Cl | | i-Pr | Cl | Cl | Br | Br |
| t-Bu | CH₃ | Br | Br | Cl | | t-Bu | Cl | Cl | Br | Br |
| Me | CH₃ | Br | Br | Br | | Me | Cl | Br | CF₃ | Cl |
| Et | CH₃ | Br | Br | Br | | Et | Cl | Br | CF₃ | Cl |
| i-Pr | CH₃ | Br | Br | Br | | i-Pr | Cl | Br | CF₃ | Cl |
| t-Bu | CH₃ | Br | Br | Br | | t-Bu | Cl | Br | CF₃ | Cl |
| Me | CH₃ | I | CF₃ | Cl | | Me | Cl | Br | CF₃ | Br |
| Et | CH₃ | I | CF₃ | Cl | | Et | Cl | Br | CF₃ | Br |
| i-Pr | CH₃ | I | CF₃ | Cl | | i-Pr | Cl | Br | CF₃ | Br |
| t-Bu | CH₃ | I | CF₃ | Cl | | t-Bu | Cl | Br | CF₃ | Br |
| Me | CH₃ | I | CF₃ | Br | | Me | Cl | H | Cl | Br |
| Et | CH₃ | I | CF₃ | Br | | Et | Cl | H | Cl | Br |
| i-Pr | CH₃ | I | CF₃ | Br | | i-Pr | Cl | H | Cl | Br |
| t-Bu | CH₃ | I | CF₃ | Br | | t-Bu | Cl | H | Cl | Br |
| Me | CH₃ | I | Cl | Cl | | Me | Cl | H | Br | Cl |
| Et | CH₃ | I | Cl | Cl | | Et | Cl | H | Br | Cl |
| i-Pr | CH₃ | I | Cl | Cl | | i-Pr | Cl | H | Br | Cl |
| t-Bu | CH₃ | I | Cl | Cl | | t-Bu | Cl | H | Br | Cl |
| Me | CH₃ | I | Cl | Br | | Me | Cl | H | Br | Br |
| Et | CH₃ | I | Cl | Br | | Et | Cl | H | Br | Br |
| i-Pr | CH₃ | I | Cl | Br | | i-Pr | Cl | H | Br | Br |
| t-Bu | CH₃ | I | Cl | Br | | t-Bu | Cl | H | Br | Br |
| Me | CH₃ | I | Br | Cl | | Me | Cl | H | CF₃ | Cl |
| Et | CH₃ | I | Br | Cl | | Et | Cl | H | CF₃ | Cl |
| i-Pr | CH₃ | I | Br | Cl | | i-Pr | Cl | H | CF₃ | Cl |
| t-Bu | CH₃ | I | Br | Cl | | t-Bu | Cl | H | CF₃ | Cl |
| Me | CH₃ | I | Br | Br | | Me | Cl | H | CF₃ | Br |
| Et | CH₃ | I | Br | Br | | Et | Cl | H | CF₃ | Br |
| i-Pr | CH₃ | I | Br | Br | | i-Pr | Cl | H | CF₃ | Br |
| t-Bu | CH₃ | I | Br | Br | | t-Bu | Cl | H | CF₃ | Br |
| Me | CH₃ | CF₃ | CF₃ | Cl | | Me | Cl | H | Cl | Cl |
| Et | CH₃ | CF₃ | CF₃ | Cl | | Et | Cl | H | Cl | Cl |
| i-Pr | CH₃ | CF₃ | CF₃ | Cl | | i-Pr | Cl | H | Cl | Cl |
| t-Bu | CH₃ | CF₃ | CF₃ | Cl | | t-Bu | Cl | H | Cl | Cl |
| Me | CH₃ | CF₃ | CF₃ | Br | | Me | CH₃ | Cl | CF₃ | Cl |
| Et | CH₃ | CF₃ | CF₃ | Br | | Et | CH₃ | Cl | CF₃ | Cl |
| i-Pr | CH₃ | CF₃ | CF₃ | Br | | i-Pr | CH₃ | Cl | CF₃ | Cl |
| t-Bu | CH₃ | CF₃ | CF₃ | Br | | t-Bu | CH₃ | Cl | CF₃ | Cl |
| Me | CH₃ | CF₃ | Cl | Cl | | Me | CH₃ | Cl | CF₃ | Br |
| Et | CH₃ | CF₃ | Cl | Cl | | Et | CH₃ | Cl | CF₃ | Br |
| i-Pr | CH₃ | CF₃ | Cl | Cl | | i-Pr | CH₃ | Cl | CF₃ | Br |
| t-Bu | CH₃ | CF₃ | Cl | Cl | | t-Bu | CH₃ | Cl | CF₃ | Br |
| Me | CH₃ | CF₃ | Cl | Br | | Me | CH₃ | Cl | Cl | Cl |
| Et | CH₃ | CF₃ | Cl | Br | | Et | CH₃ | Cl | Cl | Cl |
| i-Pr | CH₃ | CF₃ | Cl | Br | | i-Pr | CH₃ | Cl | Cl | Cl |
| t-Bu | CH₃ | CF₃ | Cl | Br | | t-Bu | CH₃ | Cl | Cl | Cl |
| Me | CH₃ | CF₃ | Br | Cl | | Me | CH₃ | Cl | Cl | Br |
| Et | CH₃ | CF₃ | Br | Cl | | Et | CH₃ | Cl | Cl | Br |
| i-Pr | CH₃ | CF₃ | Br | Cl | | i-Pr | CH₃ | Cl | Cl | Br |
| t-Bu | CH₃ | CF₃ | Br | Cl | | t-Bu | CH₃ | Cl | Cl | Br |
| Me | CH₃ | CF₃ | Br | Br | | Me | CH₃ | Cl | Br | Cl |
| Et | CH₃ | CF₃ | Br | Br | | Et | CH₃ | Cl | Br | Cl |
| i-Pr | CH₃ | CF₃ | Br | Br | | i-Pr | CH₃ | Cl | Br | Cl |
| t-Bu | CH₃ | CF₃ | Br | Br | | t-Bu | CH₃ | Cl | Br | Cl |
| n-Pr | CH₃ | Cl | Cl | Cl | | Me | CH₃ | Cl | Br | Br |
| n-Bu | CH₃ | Cl | Cl | Cl | | Et | CH₃ | Cl | Br | Br |
| s-Bu | CH₃ | Cl | Cl | Cl | | i-Pr | CH₃ | Cl | Br | Br |
| i-Bu | CH₃ | Cl | Cl | Cl | | t-Bu | CH₃ | Cl | Br | Br |
| Me | Cl | Cl | Br | Cl | | Me | Cl | F | CF₃ | Cl |
| Et | Cl | Cl | Br | Cl | | Et | Cl | F | CF₃ | Cl |
| i-Pr | Cl | Cl | Br | Cl | | i-Pr | Cl | F | CF₃ | Cl |
| t-Bu | Cl | Cl | Br | Cl | | t-Bu | Cl | F | CF₃ | Cl |
| | | | | | | Me | Cl | F | CF₃ | Br |

TABLE 6-continued

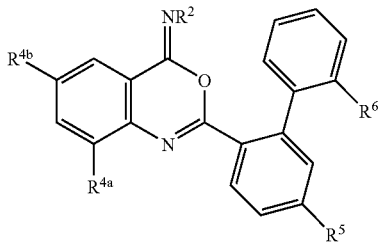

| R² | R⁴ᵃ | R⁴ᵇ | R⁵ | R⁶ |
|---|---|---|---|---|
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Cl | Br | Cl | Cl |
| Et | Cl | Br | Cl | Cl |
| i-Pr | Cl | Br | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| t-Bu | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |

TABLE 6-continued

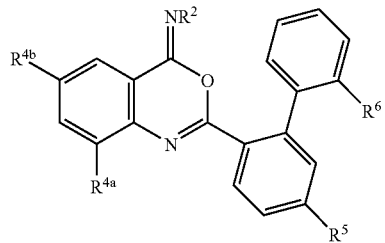

| $R^2$ | $R^{4a}$ | $R^{4b}$ | $R^5$ | $R^6$ |
|---|---|---|---|---|
| i-Pr | Cl | $CF_3$ | $CF_3$ | Br |
| t-Bu | Cl | $CF_3$ | $CF_3$ | Br |
| Me | Cl | $CF_3$ | Cl | Cl |
| Et | Cl | $CF_3$ | Cl | Cl |
| i-Pr | Cl | $CF_3$ | Cl | Cl |
| t-Bu | Cl | $CF_3$ | Cl | Cl |
| Me | Cl | $CF_3$ | Cl | Br |
| Et | Cl | $CF_3$ | Cl | Br |
| i-Pr | Cl | $CF_3$ | Cl | Br |
| t-Bu | Cl | $CF_3$ | Cl | Br |
| Me | Cl | $CF_3$ | Br | Cl |
| Et | Cl | $CF_3$ | Br | Cl |
| i-Pr | Cl | $CF_3$ | Br | Cl |
| t-Bu | Cl | $CF_3$ | Br | Cl |
| Me | Cl | $CF_3$ | Br | Br |
| Et | Cl | $CF_3$ | Br | Br |
| i-Pr | Cl | $CF_3$ | Br | Br |
| t-Bu | Cl | $CF_3$ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | $CF_3$ | Cl |
| Et | Br | F | $CF_3$ | Cl |
| i-Pr | Br | F | $CF_3$ | Cl |
| t-Bu | Br | F | $CF_3$ | Cl |
| Me | Br | F | $CF_3$ | Br |
| Et | Br | F | $CF_3$ | Br |
| i-Pr | Br | F | $CF_3$ | Br |
| t-Bu | Br | F | $CF_3$ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | $CF_3$ | Cl |
| Et | Br | Cl | $CF_3$ | Cl |
| i-Pr | Br | Cl | $CF_3$ | Cl |
| t-Bu | Br | Cl | $CF_3$ | Cl |
| Me | Br | Cl | $CF_3$ | Br |
| Et | Br | Cl | $CF_3$ | Br |
| i-Pr | Br | Cl | $CF_3$ | Br |
| t-Bu | Br | Cl | $CF_3$ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |

TABLE 6-continued

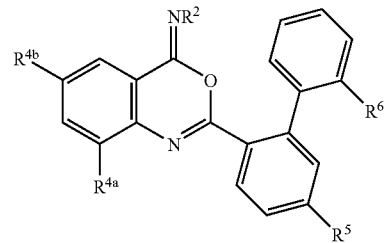

| $R^2$ | $R^{4a}$ | $R^{4b}$ | $R^5$ | $R^6$ |
|---|---|---|---|---|
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| Me | Br | Br | $CF_3$ | Cl |
| Et | Br | Br | $CF_3$ | Cl |
| i-Pr | Br | Br | $CF_3$ | Cl |
| t-Bu | Br | Br | $CF_3$ | Cl |
| Me | Br | Br | $CF_3$ | Br |
| Et | Br | Br | $CF_3$ | Br |
| i-Pr | Br | Br | $CF_3$ | Br |
| t-Bu | Br | Br | $CF_3$ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| t-Bu | Cl | Br | $CF_3$ | Br |
| t-Bu | Cl | Br | Cl | Cl |

TABLE 7

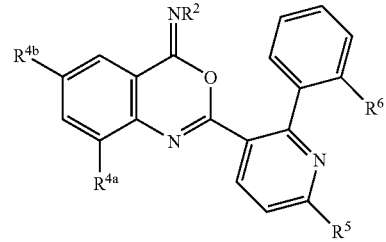

| $R^2$ | $R^{4a}$ | $R^{4b}$ | $R^5$ | $R^6$ |
|---|---|---|---|---|
| Me | $CH_3$ | H | $CF_3$ | Cl |
| Et | $CH_3$ | H | $CF_3$ | Cl |
| i-Pr | $CH_3$ | H | $CF_3$ | Cl |
| t-Bu | $CH_3$ | H | $CF_3$ | Cl |
| Me | $CH_3$ | H | $CF_3$ | Br |
| Et | $CH_3$ | H | $CF_3$ | Br |
| i-Pr | $CH_3$ | H | $CF_3$ | Br |
| t-Bu | $CH_3$ | H | $CF_3$ | Br |
| Me | $CH_3$ | H | Cl | Cl |
| Et | $CH_3$ | H | Cl | Cl |
| i-Pr | $CH_3$ | H | Cl | Cl |
| t-Bu | $CH_3$ | H | Cl | Cl |

TABLE 7-continued

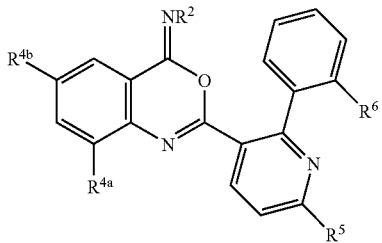

| R² | R⁴ᵃ | R⁴ᵇ | R⁵ | R⁶ |
|---|---|---|---|---|
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |

TABLE 7-continued

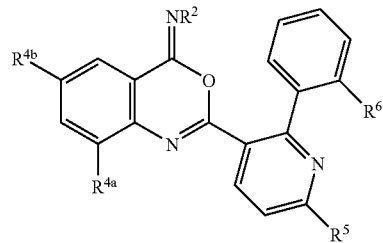

| R² | R⁴ᵃ | R⁴ᵇ | R⁵ | R⁶ |
|---|---|---|---|---|
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| Me | CH₃ | CF₃ | Br | Br |
| Et | CH₃ | CF₃ | Br | Br |
| i-Pr | CH₃ | CF₃ | Br | Br |
| t-Bu | CH₃ | CF₃ | Br | Br |
| n-Pr | CH₃ | Cl | Cl | Cl |
| n-Bu | CH₃ | Cl | Cl | Cl |
| s-Bu | CH₃ | Cl | Cl | Cl |
| i-Bu | CH₃ | Cl | Cl | Cl |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| Me | Cl | H | Cl | Br |

TABLE 7-continued

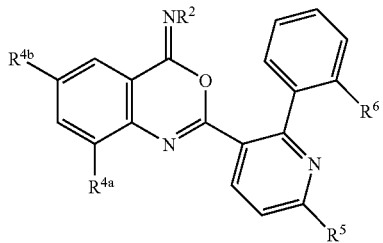

| R² | R⁴ᵃ | R⁴ᵇ | R⁵ | R⁶ |
|---|---|---|---|---|
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| t-Bu | Cl | H | Cl | Cl |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |

TABLE 7-continued

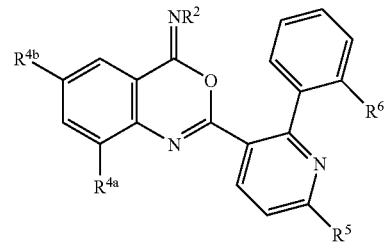

| R² | R⁴ᵃ | R⁴ᵇ | R⁵ | R⁶ |
|---|---|---|---|---|
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |

TABLE 7-continued

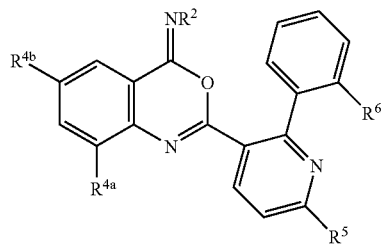

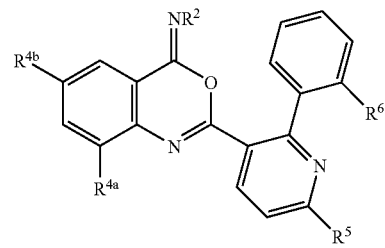

| R² | R⁴ᵃ | R⁴ᵇ | R⁵ | R⁶ | | R² | R⁴ᵃ | R⁴ᵇ | R⁵ | R⁶ |
|---|---|---|---|---|---|---|---|---|---|---|
| Et | Br | I | Br | Cl | | i-Pr | Cl | CF₃ | Br | Cl |
| i-Pr | Br | I | Br | Cl | | t-Bu | Cl | CF₃ | Br | Cl |
| t-Bu | Br | I | Br | Cl | | Me | Cl | CF₃ | Br | Br |
| Me | Br | I | Br | Br | | Et | Cl | CF₃ | Br | Br |
| Et | Br | I | Br | Br | | i-Pr | Cl | CF₃ | Br | Br |
| i-Pr | Br | I | Br | Br | | t-Bu | Cl | CF₃ | Br | Br |
| t-Bu | Br | I | Br | Br | | n-Pr | Cl | Cl | Cl | Cl |
| Me | Cl | Br | Cl | Cl | | n-Bu | Cl | Cl | Cl | Cl |
| Et | Cl | Br | Cl | Cl | | s-Bu | Cl | Cl | Cl | Cl |
| i-Pr | Cl | Br | Cl | Cl | | i-Bu | Cl | Cl | Cl | Cl |
| Me | Cl | Br | Cl | Br | | Me | Br | F | CF₃ | Cl |
| Et | Cl | Br | Cl | Br | | Et | Br | F | CF₃ | Cl |
| i-Pr | Cl | Br | Cl | Br | | i-Pr | Br | F | CF₃ | Cl |
| t-Bu | Cl | Br | Cl | Br | | t-Bu | Br | F | CF₃ | Cl |
| Me | Cl | Br | Br | Cl | | Me | Br | F | CF₃ | Br |
| Et | Cl | Br | Br | Cl | | Et | Br | F | CF₃ | Br |
| i-Pr | Cl | Br | Br | Cl | | i-Pr | Br | F | CF₃ | Br |
| t-Bu | Cl | Br | Br | Cl | | t-Bu | Br | F | CF₃ | Br |
| Me | Cl | Br | Br | Br | | Me | Br | F | Cl | Cl |
| Et | Cl | Br | Br | Br | | Et | Br | F | Cl | Cl |
| i-Pr | Cl | Br | Br | Br | | i-Pr | Br | F | Cl | Cl |
| t-Bu | Cl | Br | Br | Br | | t-Bu | Br | F | Cl | Cl |
| Me | Cl | I | CF₃ | Cl | | Me | Br | F | Cl | Br |
| Et | Cl | I | CF₃ | Cl | | Et | Br | F | Cl | Br |
| i-Pr | Cl | I | CF₃ | Cl | | i-Pr | Br | F | Cl | Br |
| t-Bu | Cl | I | CF₃ | Cl | | t-Bu | Br | F | Cl | Br |
| Me | Cl | I | CF₃ | Br | | Me | Br | F | Br | Cl |
| Et | Cl | I | CF₃ | Br | | Et | Br | F | Br | Cl |
| i-Pr | Cl | I | CF₃ | Br | | i-Pr | Br | F | Br | Cl |
| t-Bu | Cl | I | CF₃ | Br | | t-Bu | Br | F | Br | Cl |
| Me | Cl | I | Cl | Cl | | Me | Br | F | Br | Br |
| Et | Cl | I | Cl | Cl | | Et | Br | F | Br | Br |
| i-Pr | Cl | I | Cl | Cl | | i-Pr | Br | F | Br | Br |
| t-Bu | Cl | I | Cl | Cl | | t-Bu | Br | F | Br | Br |
| Me | Cl | I | Cl | Br | | Me | Br | Cl | CF₃ | Cl |
| Et | Cl | I | Cl | Br | | Et | Br | Cl | CF₃ | Cl |
| i-Pr | Cl | I | Cl | Br | | i-Pr | Br | Cl | CF₃ | Cl |
| t-Bu | Cl | I | Cl | Br | | t-Bu | Br | Cl | CF₃ | Cl |
| Me | Cl | I | Br | Cl | | Me | Br | Cl | CF₃ | Br |
| Et | Cl | I | Br | Cl | | Et | Br | Cl | CF₃ | Br |
| i-Pr | Cl | I | Br | Cl | | i-Pr | Br | Cl | CF₃ | Br |
| t-Bu | Cl | I | Br | Cl | | t-Bu | Br | Cl | CF₃ | Br |
| Me | Cl | I | Br | Br | | Me | Br | Cl | Cl | Cl |
| Et | Cl | I | Br | Br | | Et | Br | Cl | Cl | Cl |
| i-Pr | Cl | I | Br | Br | | i-Pr | Br | Cl | Cl | Cl |
| t-Bu | Cl | I | Br | Br | | t-Bu | Br | Cl | Cl | Cl |
| Me | Cl | CF₃ | CF₃ | Cl | | Me | Br | Cl | Cl | Br |
| Et | Cl | CF₃ | CF₃ | Cl | | Et | Br | Cl | Cl | Br |
| i-Pr | Cl | CF₃ | CF₃ | Cl | | i-Pr | Br | Cl | Cl | Br |
| t-Bu | Cl | CF₃ | CF₃ | Cl | | t-Bu | Br | Cl | Cl | Br |
| Me | Cl | CF₃ | CF₃ | Br | | Me | Br | Cl | Br | Cl |
| Et | Cl | CF₃ | CF₃ | Br | | Et | Br | Cl | Br | Cl |
| i-Pr | Cl | CF₃ | CF₃ | Br | | i-Pr | Br | Cl | Br | Cl |
| t-Bu | Cl | CF₃ | CF₃ | Br | | t-Bu | Br | Cl | Br | Cl |
| Me | Cl | CF₃ | Cl | Cl | | Me | Br | Cl | Br | Br |
| Et | Cl | CF₃ | Cl | Cl | | Et | Br | Cl | Br | Br |
| i-Pr | Cl | CF₃ | Cl | Cl | | i-Pr | Br | Cl | Br | Br |
| t-Bu | Cl | CF₃ | Cl | Cl | | t-Bu | Br | Cl | Br | Br |
| Me | Cl | CF₃ | Cl | Br | | Me | Br | Br | CF₃ | Cl |
| Et | Cl | CF₃ | Cl | Br | | Et | Br | Br | CF₃ | Cl |
| i-Pr | Cl | CF₃ | Cl | Br | | i-Pr | Br | Br | CF₃ | Cl |
| t-Bu | Cl | CF₃ | Cl | Br | | t-Bu | Br | Br | CF₃ | Cl |
| Me | Cl | CF₃ | Br | Cl | | Me | Br | Br | CF₃ | Br |
| Et | Cl | CF₃ | Br | Cl | | Et | Br | Br | CF₃ | Br |

TABLE 7-continued

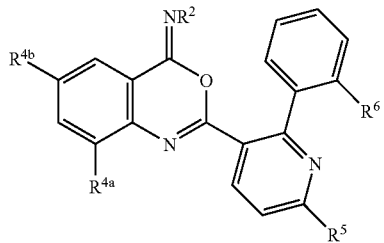

| R² | R⁴ᵃ | R⁴ᵇ | R⁵ | R⁶ |
|---|---|---|---|---|
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| t-Bu | Cl | Br | CF₃ | Br |
| t-Bu | Cl | Br | Cl | Cl |

TABLE 8

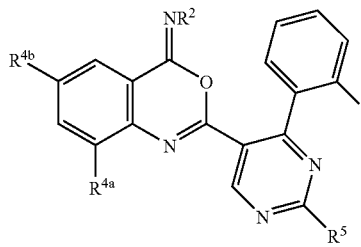

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |

TABLE 8-continued

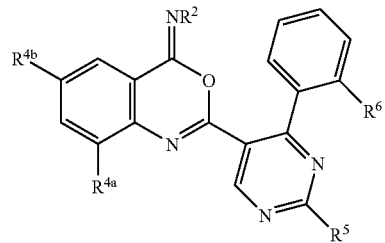

| R² | R⁴ᵃ | R⁴ᵇ | R⁵ | R⁶ |
|---|---|---|---|---|
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |

TABLE 8-continued

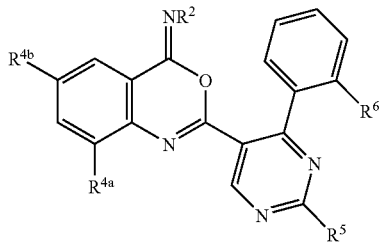

| R² | R⁴ᵃ | R⁴ᵇ | R⁵ | R⁶ |
|---|---|---|---|---|
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| Me | CH₃ | CF₃ | Br | Br |
| Et | CH₃ | CF₃ | Br | Br |
| i-Pr | CH₃ | CF₃ | Br | Br |
| t-Bu | CH₃ | CF₃ | Br | Br |
| n-Pr | CH₃ | Cl | Cl | Cl |
| n-Bu | CH₃ | Cl | Cl | Cl |
| s-Bu | CH₃ | Cl | Cl | Cl |
| i-Bu | CH₃ | Cl | Cl | Cl |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| t-Bu | Cl | H | Cl | Cl |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |

TABLE 8-continued

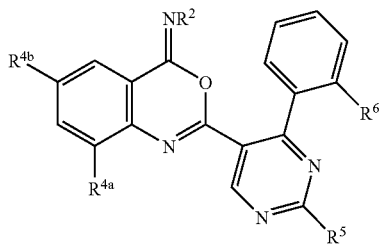

| R² | R⁴ᵃ | R⁴ᵇ | R⁵ | R⁶ |
|---|---|---|---|---|
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Cl | Br | Cl | Cl |
| Et | Cl | Br | Cl | Cl |
| i-Pr | Cl | Br | Cl | Cl |
| Me | Cl | Br | Cl | Br |
| Et | Cl | Br | Cl | Br |

TABLE 8-continued

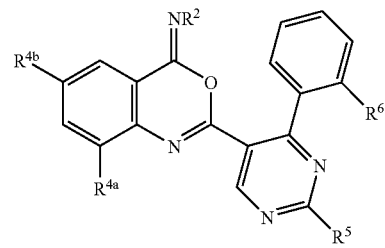

| R² | R⁴ᵃ | R⁴ᵇ | R⁵ | R⁶ |
|---|---|---|---|---|
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| t-Bu | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |

TABLE 8-continued

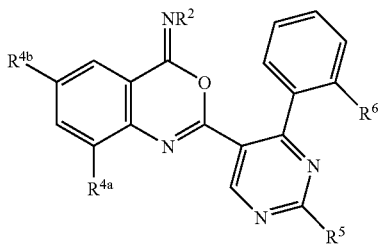

| R² | R⁴ᵃ | R⁴ᵇ | R⁵ | R⁶ |
|---|---|---|---|---|
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| Me | Br | Br | CF₃ | Cl |
| Et | Br | Br | CF₃ | Cl |
| i-Pr | Br | Br | CF₃ | Cl |
| t-Bu | Br | Br | CF₃ | Cl |
| Me | Br | Br | CF₃ | Br |
| Et | Br | Br | CF₃ | Br |
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | Br | Br | Br | Cl |
| Et | Br | Br | Br | Cl |

TABLE 8-continued

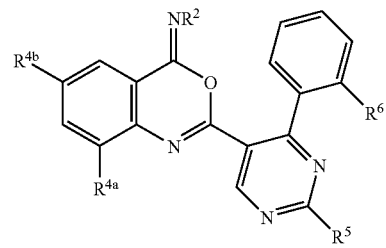

| R² | R⁴ᵃ | R⁴ᵇ | R⁵ | R⁶ |
|---|---|---|---|---|
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| t-Bu | Cl | Br | CF₃ | Br |
| t-Bu | Cl | Br | Cl | Cl |

TABLE 9

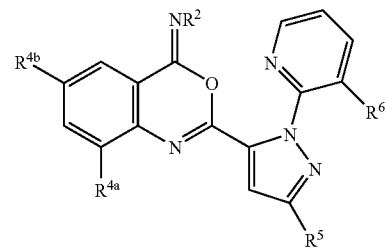

| R² | R⁴ᵃ | R⁴ᵇ | R⁵ | R⁶ |
|---|---|---|---|---|
| H | CH₃ | H | CF₃ | F |
| Me | CH₃ | H | CF₃ | F |
| Et | CH₃ | H | CF₃ | F |
| i-Pr | CH₃ | H | CF₃ | F |
| t-Bu | CH₃ | H | CF₃ | F |
| H | CH₃ | H | CF₃ | Cl |
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| H | CH₃ | H | CF₃ | Br |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| H | CH₃ | H | Cl | F |
| Me | CH₃ | H | Cl | F |
| Et | CH₃ | H | Cl | F |
| i-Pr | CH₃ | H | Cl | F |
| t-Bu | CH₃ | H | Cl | F |
| H | CH₃ | H | Cl | Cl |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| H | CH₃ | H | Cl | Br |
| Me | CH₃ | H | Cl | Br |
| Et | CH₃ | H | Cl | Br |
| i-Pr | CH₃ | H | Cl | Br |
| t-Bu | CH₃ | H | Cl | Br |
| H | CH₃ | H | Br | F |
| Me | CH₃ | H | Br | F |
| Et | CH₃ | H | Br | F |
| i-Pr | CH₃ | H | Br | F |
| t-Bu | CH₃ | H | Br | F |
| H | CH₃ | H | Br | Cl |

TABLE 9-continued

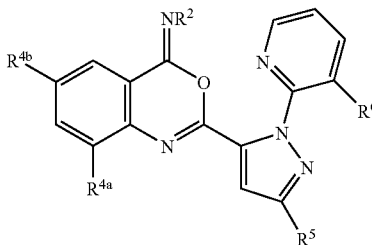

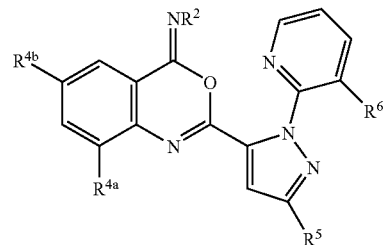

| R² | R⁴ᵃ | R⁴ᵇ | R⁵ | R⁶ |
|---|---|---|---|---|
| Me | CH₃ | H | Br | Cl |
| Et | CH₃ | H | Br | Cl |
| i-Pr | CH₃ | H | Br | Cl |
| t-Bu | CH₃ | H | Br | Cl |
| H | CH₃ | H | Br | Br |
| Me | CH₃ | H | Br | Br |
| Et | CH₃ | H | Br | Br |
| i-Pr | CH₃ | H | Br | Br |
| t-Bu | CH₃ | H | Br | Br |
| H | CH₃ | F | CF₃ | F |
| Me | CH₃ | F | CF₃ | F |
| Et | CH₃ | F | CF₃ | F |
| i-Pr | CH₃ | F | CF₃ | F |
| t-Bu | CH₃ | F | CF₃ | F |
| H | CH₃ | F | CF₃ | Cl |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| H | CH₃ | F | CF₃ | Br |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| H | CH₃ | F | Cl | F |
| Me | CH₃ | F | Cl | F |
| Et | CH₃ | F | Cl | F |
| i-Pr | CH₃ | F | Cl | F |
| t-Bu | CH₃ | F | Cl | F |
| H | CH₃ | F | Cl | Cl |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| H | CH₃ | F | Cl | Br |
| Me | CH₃ | F | Cl | Br |
| Et | CH₃ | F | Cl | Br |
| i-Pr | CH₃ | F | Cl | Br |
| t-Bu | CH₃ | F | Cl | Br |
| H | CH₃ | F | Br | F |
| Me | CH₃ | F | Br | F |
| Et | CH₃ | F | Br | F |
| i-Pr | CH₃ | F | Br | F |
| t-Bu | CH₃ | F | Br | F |
| H | CH₃ | F | Br | Cl |
| Me | CH₃ | F | Br | Cl |
| Et | CH₃ | F | Br | Cl |
| i-Pr | CH₃ | F | Br | Cl |
| t-Bu | CH₃ | F | Br | Cl |
| H | CH₃ | F | Br | Br |
| Me | CH₃ | F | Br | Br |
| Et | CH₃ | F | Br | Br |
| i-Pr | CH₃ | F | Br | Br |
| t-Bu | CH₃ | F | Br | Br |
| H | CH₃ | Cl | CF₃ | F |
| Me | CH₃ | Cl | CF₃ | F |
| Et | CH₃ | Cl | CF₃ | F |
| i-Pr | CH₃ | Cl | CF₃ | F |
| t-Bu | CH₃ | Cl | CF₃ | F |
| H | CH₃ | Cl | CF₃ | Cl |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| H | CH₃ | Cl | CF₃ | Br |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| H | CH₃ | Cl | Cl | F |
| Me | CH₃ | Cl | Cl | F |
| Et | CH₃ | Cl | Cl | F |
| i-Pr | CH₃ | Cl | Cl | F |
| t-Bu | CH₃ | Cl | Cl | F |
| H | CH₃ | Cl | Cl | Cl |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| H | CH₃ | Cl | Cl | Br |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| H | CH₃ | Cl | Br | F |
| Me | CH₃ | Cl | Br | F |
| Et | CH₃ | Cl | Br | F |
| i-Pr | CH₃ | Cl | Br | F |
| t-Bu | CH₃ | Cl | Br | F |
| H | CH₃ | Cl | Br | Cl |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| H | CH₃ | Cl | Br | Br |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| H | CH₃ | Br | CF₃ | F |
| Me | CH₃ | Br | CF₃ | F |
| Et | CH₃ | Br | CF₃ | F |
| i-Pr | CH₃ | Br | CF₃ | F |
| t-Bu | CH₃ | Br | CF₃ | F |
| H | CH₃ | Br | CF₃ | Cl |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| H | CH₃ | Br | CF₃ | Br |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| H | CH₃ | Br | Cl | F |
| Me | CH₃ | Br | Cl | F |
| Et | CH₃ | Br | Cl | F |
| i-Pr | CH₃ | Br | Cl | F |
| t-Bu | CH₃ | Br | Cl | F |
| H | CH₃ | Br | Cl | Cl |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| H | CH₃ | Br | Cl | Br |
| Me | CH₃ | Br | Cl | Br |
| Et | CH₃ | Br | Cl | Br |
| i-Pr | CH₃ | Br | Cl | Br |

TABLE 9-continued

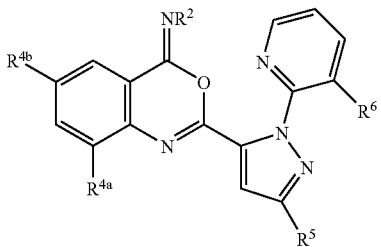

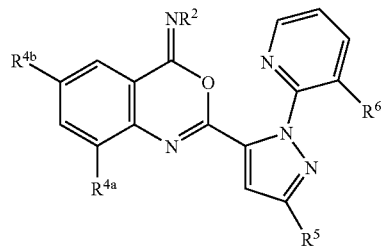

| R² | R⁴ᵃ | R⁴ᵇ | R⁵ | R⁶ | | R² | R⁴ᵃ | R⁴ᵇ | R⁵ | R⁶ |
|---|---|---|---|---|---|---|---|---|---|---|
| t-Bu | CH₃ | Br | Cl | Br | | i-Pr | CH₃ | CF₃ | CF₃ | F |
| H | CH₃ | Br | Br | F | | t-Bu | CH₃ | CF₃ | CF₃ | F |
| Me | CH₃ | Br | Br | F | | H | CH₃ | CF₃ | CF₃ | Cl |
| Et | CH₃ | Br | Br | F | | Me | CH₃ | CF₃ | CF₃ | Cl |
| i-Pr | CH₃ | Br | Br | F | | Et | CH₃ | CF₃ | CF₃ | Cl |
| t-Bu | CH₃ | Br | Br | F | | i-Pr | CH₃ | CF₃ | CF₃ | Cl |
| H | CH₃ | Br | Br | Cl | | t-Bu | CH₃ | CF₃ | CF₃ | Cl |
| Me | CH₃ | Br | Br | Cl | | H | CH₃ | CF₃ | CF₃ | Br |
| Et | CH₃ | Br | Br | Cl | | Me | CH₃ | CF₃ | CF₃ | Br |
| i-Pr | CH₃ | Br | Br | Cl | | Et | CH₃ | CF₃ | CF₃ | Br |
| t-Bu | CH₃ | Br | Br | Cl | | i-Pr | CH₃ | CF₃ | CF₃ | Br |
| H | CH₃ | Br | Br | Br | | t-Bu | CH₃ | CF₃ | CF₃ | Br |
| Me | CH₃ | Br | Br | Br | | H | CH₃ | CF₃ | Cl | F |
| Et | CH₃ | Br | Br | Br | | Me | CH₃ | CF₃ | Cl | F |
| i-Pr | CH₃ | Br | Br | Br | | Et | CH₃ | CF₃ | Cl | F |
| t-Bu | CH₃ | Br | Br | Br | | i-Pr | CH₃ | CF₃ | Cl | F |
| H | CH₃ | I | CF₃ | F | | t-Bu | CH₃ | CF₃ | Cl | F |
| Me | CH₃ | I | CF₃ | F | | H | CH₃ | CF₃ | Cl | Cl |
| Et | CH₃ | I | CF₃ | F | | Me | CH₃ | CF₃ | Cl | Cl |
| i-Pr | CH₃ | I | CF₃ | F | | Et | CH₃ | CF₃ | Cl | Cl |
| t-Bu | CH₃ | I | CF₃ | F | | i-Pr | CH₃ | CF₃ | Cl | Cl |
| H | CH₃ | I | CF₃ | Cl | | t-Bu | CH₃ | CF₃ | Cl | Cl |
| Me | CH₃ | I | CF₃ | Cl | | H | CH₃ | CF₃ | Cl | Br |
| Et | CH₃ | I | CF₃ | Cl | | Me | CH₃ | CF₃ | Cl | Br |
| i-Pr | CH₃ | I | CF₃ | Cl | | Et | CH₃ | CF₃ | Cl | Br |
| t-Bu | CH₃ | I | CF₃ | Cl | | i-Pr | CH₃ | CF₃ | Cl | Br |
| H | CH₃ | I | CF₃ | Br | | t-Bu | CH₃ | CF₃ | Cl | Br |
| Me | CH₃ | I | CF₃ | Br | | H | CH₃ | CF₃ | Br | F |
| Et | CH₃ | I | CF₃ | Br | | Me | CH₃ | CF₃ | Br | F |
| i-Pr | CH₃ | I | CF₃ | Br | | Et | CH₃ | CF₃ | Br | F |
| t-Bu | CH₃ | I | CF₃ | Br | | i-Pr | CH₃ | CF₃ | Br | F |
| H | CH₃ | I | Cl | F | | t-Bu | CH₃ | CF₃ | Br | F |
| Me | CH₃ | I | Cl | F | | H | CH₃ | CF₃ | Br | Cl |
| Et | CH₃ | I | Cl | F | | Me | CH₃ | CF₃ | Br | Cl |
| i-Pr | CH₃ | I | Cl | F | | Et | CH₃ | CF₃ | Br | Cl |
| t-Bu | CH₃ | I | Cl | F | | i-Pr | CH₃ | CF₃ | Br | Cl |
| H | CH₃ | I | Cl | Cl | | t-Bu | CH₃ | CF₃ | Br | Cl |
| Me | CH₃ | I | Cl | Cl | | H | CH₃ | CF₃ | Br | Br |
| Et | CH₃ | I | Cl | Cl | | Me | CH₃ | CF₃ | Br | Br |
| i-Pr | CH₃ | I | Cl | Cl | | Et | CH₃ | CF₃ | Br | Br |
| t-Bu | CH₃ | I | Cl | Cl | | i-Pr | CH₃ | CF₃ | Br | Br |
| H | CH₃ | I | Cl | Br | | t-Bu | CH₃ | CF₃ | Br | Br |
| Me | CH₃ | I | Cl | Br | | n-Pr | CH₃ | Cl | Cl | Cl |
| Et | CH₃ | I | Cl | Br | | n-Bu | CH₃ | Cl | Cl | Cl |
| i-Pr | CH₃ | I | Cl | Br | | s-Bu | CH₃ | Cl | Cl | Cl |
| t-Bu | CH₃ | I | Cl | Br | | i-Bu | CH₃ | Cl | Cl | Cl |
| H | CH₃ | I | Br | F | | H | Cl | H | CF₃ | F |
| Me | CH₃ | I | Br | F | | Me | Cl | H | CF₃ | F |
| Et | CH₃ | I | Br | F | | Et | Cl | H | CF₃ | F |
| i-Pr | CH₃ | I | Br | F | | i-Pr | Cl | H | CF₃ | F |
| t-Bu | CH₃ | I | Br | F | | t-Bu | Cl | H | CF₃ | F |
| H | CH₃ | I | Br | Cl | | H | Cl | H | CF₃ | Cl |
| Me | CH₃ | I | Br | Cl | | Me | Cl | H | CF₃ | Cl |
| Et | CH₃ | I | Br | Cl | | Et | Cl | H | CF₃ | Cl |
| i-Pr | CH₃ | I | Br | Cl | | i-Pr | Cl | H | CF₃ | Cl |
| t-Bu | CH₃ | I | Br | Cl | | t-Bu | Cl | H | CF₃ | Cl |
| H | CH₃ | I | Br | Br | | H | Cl | H | CF₃ | Br |
| Me | CH₃ | I | Br | Br | | Me | Cl | H | CF₃ | Br |
| Et | CH₃ | I | Br | Br | | Et | Cl | H | CF₃ | Br |
| i-Pr | CH₃ | I | Br | Br | | i-Pr | Cl | H | CF₃ | Br |
| t-Bu | CH₃ | I | Br | Br | | t-Bu | Cl | H | CF₃ | Br |
| H | CH₃ | CF₃ | CF₃ | F | | H | Cl | H | Cl | F |
| Me | CH₃ | CF₃ | CF₃ | F | | Me | Cl | H | Cl | F |
| Et | CH₃ | CF₃ | CF₃ | F | | Et | Cl | H | Cl | F |

TABLE 9-continued

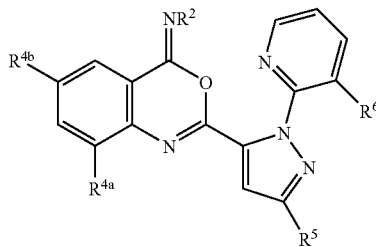

| R² | R⁴ᵃ | R⁴ᵇ | R⁵ | R⁶ |
|---|---|---|---|---|
| i-Pr | Cl | H | Cl | F |
| t-Bu | Cl | H | Cl | F |
| H | Cl | H | Cl | Cl |
| Me | Cl | H | Cl | Cl |
| Et | Cl | H | Cl | Cl |
| i-Pr | Cl | H | Cl | Cl |
| t-Bu | Cl | H | Cl | Cl |
| H | Cl | H | Cl | Br |
| Me | Cl | H | Cl | Br |
| Et | Cl | H | Cl | Br |
| i-Pr | Cl | H | Cl | Br |
| t-Bu | Cl | H | Cl | Br |
| H | Cl | H | Br | F |
| Me | Cl | H | Br | F |
| Et | Cl | H | Br | F |
| i-Pr | Cl | H | Br | F |
| t-Bu | Cl | H | Br | F |
| H | Cl | H | Br | Cl |
| Me | Cl | H | Br | Cl |
| Et | Cl | H | Br | Cl |
| i-Pr | Cl | H | Br | Cl |
| t-Bu | Cl | H | Br | Cl |
| H | Cl | H | Br | Br |
| Me | Cl | H | Br | Br |
| Et | Cl | H | Br | Br |
| i-Pr | Cl | H | Br | Br |
| t-Bu | Cl | H | Br | Br |
| H | Cl | F | CF₃ | F |
| Me | Cl | F | CF₃ | F |
| Et | Cl | F | CF₃ | F |
| i-Pr | Cl | F | CF₃ | F |
| t-Bu | Cl | F | CF₃ | F |
| H | Cl | F | CF₃ | Cl |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| H | Cl | F | CF₃ | Br |
| Me | Cl | F | CF₃ | Br |
| Et | Cl | F | CF₃ | Br |
| i-Pr | Cl | F | CF₃ | Br |
| t-Bu | Cl | F | CF₃ | Br |
| H | Cl | F | Cl | F |
| Me | Cl | F | Cl | F |
| Et | Cl | F | Cl | F |
| i-Pr | Cl | F | Cl | F |
| t-Bu | Cl | F | Cl | F |
| H | Cl | F | Cl | Cl |
| Me | Cl | F | Cl | Cl |
| Et | Cl | F | Cl | Cl |
| i-Pr | Cl | F | Cl | Cl |
| t-Bu | Cl | F | Cl | Cl |
| H | Cl | F | Cl | Br |
| Me | Cl | F | Cl | Br |
| Et | Cl | F | Cl | Br |
| i-Pr | Cl | F | Cl | Br |
| t-Bu | Cl | F | Cl | Br |
| H | Cl | F | Br | F |
| Me | Cl | F | Br | F |
| Et | Cl | F | Br | F |
| i-Pr | Cl | F | Br | F |
| t-Bu | Cl | F | Br | F |
| H | Cl | F | Br | Cl |
| Me | Cl | F | Br | Cl |

TABLE 9-continued

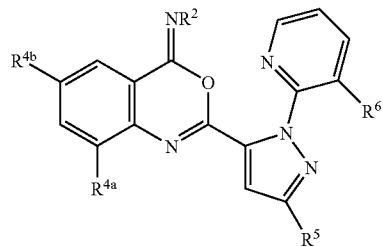

| R² | R⁴ᵃ | R⁴ᵇ | R⁵ | R⁶ |
|---|---|---|---|---|
| Et | Cl | F | Br | Cl |
| i-Pr | Cl | F | Br | Cl |
| t-Bu | Cl | F | Br | Cl |
| H | Cl | F | Br | Br |
| Me | Cl | F | Br | Br |
| Et | Cl | F | Br | Br |
| i-Pr | Cl | F | Br | Br |
| t-Bu | Cl | F | Br | Br |
| H | Cl | Cl | CF₃ | F |
| Me | Cl | Cl | CF₃ | F |
| Et | Cl | Cl | CF₃ | F |
| i-Pr | Cl | Cl | CF₃ | F |
| t-Bu | Cl | Cl | CF₃ | F |
| H | Cl | Cl | CF₃ | Cl |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| H | Cl | Cl | CF₃ | Br |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| H | Cl | Cl | Cl | F |
| Me | Cl | Cl | Cl | F |
| Et | Cl | Cl | Cl | F |
| i-Pr | Cl | Cl | Cl | F |
| t-Bu | Cl | Cl | Cl | F |
| H | Cl | Cl | Cl | Cl |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| H | Cl | Cl | Cl | Br |
| Me | Cl | Cl | Cl | Br |
| Et | Cl | Cl | Cl | Br |
| i-Pr | Cl | Cl | Cl | Br |
| t-Bu | Cl | Cl | Cl | Br |
| H | Cl | Cl | Br | F |
| Me | Cl | Cl | Br | F |
| Et | Cl | Cl | Br | F |
| i-Pr | Cl | Cl | Br | F |
| t-Bu | Cl | Cl | Br | F |
| H | Cl | Cl | Br | Cl |
| Me | Cl | Cl | Br | Cl |
| Et | Cl | Cl | Br | Cl |
| i-Pr | Cl | Cl | Br | Cl |
| t-Bu | Cl | Cl | Br | Cl |
| H | Cl | Cl | Br | Br |
| Me | Cl | Cl | Br | Br |
| Et | Cl | Cl | Br | Br |
| i-Pr | Cl | Cl | Br | Br |
| t-Bu | Cl | Cl | Br | Br |
| H | Cl | Br | CF₃ | F |
| Me | Cl | Br | CF₃ | F |
| Et | Cl | Br | CF₃ | F |
| i-Pr | Cl | Br | CF₃ | F |
| t-Bu | Cl | Br | CF₃ | F |
| H | Cl | Br | CF₃ | Cl |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| H | Cl | Br | CF₃ | Br |

TABLE 9-continued

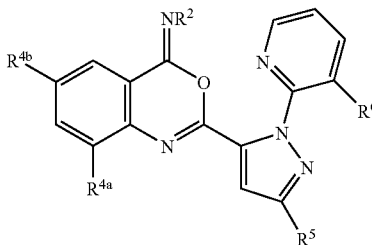

| R² | R⁴ᵃ | R⁴ᵇ | R⁵ | R⁶ |
|---|---|---|---|---|
| Me | Cl | Br | CF₃ | Br |
| Et | Cl | Br | CF₃ | Br |
| i-Pr | Cl | Br | CF₃ | Br |
| t-Bu | Cl | Br | CF₃ | Br |
| H | Cl | Br | Cl | F |
| Me | Cl | Br | Cl | F |
| Et | Cl | Br | Cl | F |
| i-Pr | Cl | Br | Cl | F |
| t-Bu | Cl | Br | Cl | F |
| H | Cl | Br | Cl | Cl |
| Me | Cl | Br | Cl | Cl |
| Et | Cl | Br | Cl | Cl |
| i-Pr | Cl | Br | Cl | Cl |
| t-Bu | Cl | Br | Cl | Cl |
| H | Cl | Br | Cl | Br |
| Me | Cl | Br | Cl | Br |
| Et | Cl | Br | Cl | Br |
| i-Pr | Cl | Br | Cl | Br |
| t-Bu | Cl | Br | Cl | Br |
| H | Cl | Br | Br | F |
| Me | Cl | Br | Br | F |
| Et | Cl | Br | Br | F |
| i-Pr | Cl | Br | Br | F |
| t-Bu | Cl | Br | Br | F |
| H | Cl | Br | Br | Cl |
| Me | Cl | Br | Br | Cl |
| Et | Cl | Br | Br | Cl |
| i-Pr | Cl | Br | Br | Cl |
| t-Bu | Cl | Br | Br | Cl |
| H | Cl | Br | Br | Br |
| Me | Cl | Br | Br | Br |
| Et | Cl | Br | Br | Br |
| i-Pr | Cl | Br | Br | Br |
| t-Bu | Cl | Br | Br | Br |
| H | Cl | I | CF₃ | F |
| Me | Cl | I | CF₃ | F |
| Et | Cl | I | CF₃ | F |
| i-Pr | Cl | I | CF₃ | F |
| t-Bu | Cl | I | CF₃ | F |
| H | Cl | I | CF₃ | Cl |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| H | Cl | I | CF₃ | Br |
| Me | Cl | I | CF₃ | Br |
| Et | Cl | I | CF₃ | Br |
| i-Pr | Cl | I | CF₃ | Br |
| t-Bu | Cl | I | CF₃ | Br |
| H | Cl | I | Cl | F |
| Me | Cl | I | Cl | F |
| Et | Cl | I | Cl | F |
| i-Pr | Cl | I | Cl | F |
| t-Bu | Cl | I | Cl | F |
| H | Cl | I | Cl | Cl |
| Me | Cl | I | Cl | Cl |
| Et | Cl | I | Cl | Cl |
| i-Pr | Cl | I | Cl | Cl |
| t-Bu | Cl | I | Cl | Cl |
| H | Cl | I | Cl | Br |
| Me | Cl | I | Cl | Br |
| Et | Cl | I | Cl | Br |
| i-Pr | Cl | I | Cl | Br |
| t-Bu | Cl | I | Cl | Br |

TABLE 9-continued

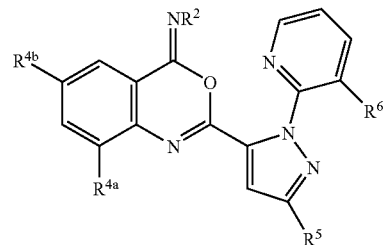

| R² | R⁴ᵃ | R⁴ᵇ | R⁵ | R⁶ |
|---|---|---|---|---|
| H | Cl | I | Br | F |
| Me | Cl | I | Br | F |
| Et | Cl | I | Br | F |
| i-Pr | Cl | I | Br | F |
| t-Bu | Cl | I | Br | F |
| H | Cl | I | Br | Cl |
| Me | Cl | I | Br | Cl |
| Et | Cl | I | Br | Cl |
| i-Pr | Cl | I | Br | Cl |
| t-Bu | Cl | I | Br | Cl |
| H | Cl | I | Br | Br |
| Me | Cl | I | Br | Br |
| Et | Cl | I | Br | Br |
| i-Pr | Cl | I | Br | Br |
| t-Bu | Cl | I | Br | Br |
| H | Cl | CF₃ | CF₃ | F |
| Me | Cl | CF₃ | CF₃ | F |
| Et | Cl | CF₃ | CF₃ | F |
| i-Pr | Cl | CF₃ | CF₃ | F |
| t-Bu | Cl | CF₃ | CF₃ | F |
| H | Cl | CF₃ | CF₃ | Cl |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| H | Cl | CF₃ | CF₃ | Br |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| H | Cl | CF₃ | Cl | F |
| Me | Cl | CF₃ | Cl | F |
| Et | Cl | CF₃ | Cl | F |
| i-Pr | Cl | CF₃ | Cl | F |
| t-Bu | Cl | CF₃ | Cl | F |
| H | Cl | CF₃ | Cl | Cl |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| H | Cl | CF₃ | Cl | Br |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| H | Cl | CF₃ | Br | F |
| Me | Cl | CF₃ | Br | F |
| Et | Cl | CF₃ | Br | F |
| i-Pr | Cl | CF₃ | Br | F |
| t-Bu | Cl | CF₃ | Br | F |
| H | Cl | CF₃ | Br | Cl |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| H | Cl | CF₃ | Br | Br |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |

TABLE 9-continued

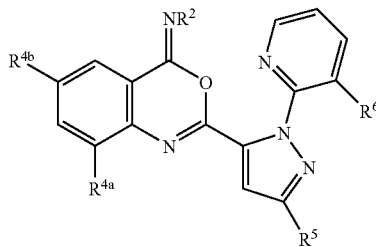

| R² | R⁴ᵃ | R⁴ᵇ | R⁵ | R⁶ |
|---|---|---|---|---|
| H | Br | H | CF₃ | F |
| Me | Br | H | CF₃ | F |
| Et | Br | H | CF₃ | F |
| i-Pr | Br | H | CF₃ | F |
| t-Bu | Br | H | CF₃ | F |
| H | Br | H | CF₃ | Cl |
| Me | Br | H | CF₃ | Cl |
| Et | Br | H | CF₃ | Cl |
| i-Pr | Br | H | CF₃ | Cl |
| t-Bu | Br | H | CF₃ | Cl |
| H | Br | H | CF₃ | Br |
| Me | Br | H | CF₃ | Br |
| Et | Br | H | CF₃ | Br |
| i-Pr | Br | H | CF₃ | Br |
| t-Bu | Br | H | CF₃ | Br |
| H | Br | H | Cl | F |
| Me | Br | H | Cl | F |
| Et | Br | H | Cl | F |
| i-Pr | Br | H | Cl | F |
| t-Bu | Br | H | Cl | F |
| H | Br | H | Cl | Cl |
| Me | Br | H | Cl | Cl |
| Et | Br | H | Cl | Cl |
| i-Pr | Br | H | Cl | Cl |
| t-Bu | Br | H | Cl | Cl |
| H | Br | H | Cl | Br |
| Me | Br | H | Cl | Br |
| Et | Br | H | Cl | Br |
| i-Pr | Br | H | Cl | Br |
| t-Bu | Br | H | Cl | Br |
| H | Br | H | Br | F |
| Me | Br | H | Br | F |
| Et | Br | H | Br | F |
| i-Pr | Br | H | Br | F |
| t-Bu | Br | H | Br | F |
| H | Br | H | Br | Cl |
| Me | Br | H | Br | Cl |
| Et | Br | H | Br | Cl |
| i-Pr | Br | H | Br | Cl |
| t-Bu | Br | H | Br | Cl |
| H | Br | H | Br | Br |
| Me | Br | H | Br | Br |
| Et | Br | H | Br | Br |
| i-Pr | Br | H | Br | Br |
| t-Bu | Br | H | Br | Br |
| H | Br | F | CF₃ | F |
| Me | Br | F | CF₃ | F |
| Et | Br | F | CF₃ | F |
| i-Pr | Br | F | CF₃ | F |
| t-Bu | Br | F | CF₃ | F |
| H | Br | F | CF₃ | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| H | Br | F | CF₃ | Br |
| Me | Br | F | CF₃ | Br |
| Et | Br | F | CF₃ | Br |
| i-Pr | Br | F | CF₃ | Br |
| t-Bu | Br | F | CF₃ | Br |
| H | Br | F | Cl | F |
| Me | Br | F | Cl | F |
| Et | Br | F | Cl | F |
| i-Pr | Br | F | Cl | F |

TABLE 9-continued

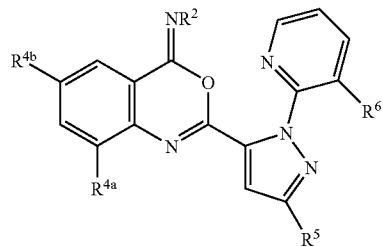

| R² | R⁴ᵃ | R⁴ᵇ | R⁵ | R⁶ |
|---|---|---|---|---|
| t-Bu | Br | F | Cl | F |
| H | Br | F | Cl | Cl |
| Me | Br | F | Cl | Cl |
| Et | Br | F | Cl | Cl |
| i-Pr | Br | F | Cl | Cl |
| t-Bu | Br | F | Cl | Cl |
| H | Br | F | Cl | Br |
| Me | Br | F | Cl | Br |
| Et | Br | F | Cl | Br |
| i-Pr | Br | F | Cl | Br |
| t-Bu | Br | F | Cl | Br |
| H | Br | F | Br | F |
| Me | Br | F | Br | F |
| Et | Br | F | Br | F |
| i-Pr | Br | F | Br | F |
| t-Bu | Br | F | Br | F |
| H | Br | F | Br | Cl |
| Me | Br | F | Br | Cl |
| Et | Br | F | Br | Cl |
| i-Pr | Br | F | Br | Cl |
| t-Bu | Br | F | Br | Cl |
| H | Br | F | Br | Br |
| Me | Br | F | Br | Br |
| Et | Br | F | Br | Br |
| i-Pr | Br | F | Br | Br |
| t-Bu | Br | F | Br | Br |
| H | Br | Cl | CF₃ | F |
| Me | Br | Cl | CF₃ | F |
| Et | Br | Cl | CF₃ | F |
| i-Pr | Br | Cl | CF₃ | F |
| t-Bu | Br | Cl | CF₃ | F |
| H | Br | Cl | CF₃ | Cl |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| H | Br | Cl | CF₃ | Br |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| H | Br | Cl | Cl | F |
| Me | Br | Cl | Cl | F |
| Et | Br | Cl | Cl | F |
| i-Pr | Br | Cl | Cl | F |
| t-Bu | Br | Cl | Cl | F |
| H | Br | Cl | Cl | Cl |
| Me | Br | Cl | Cl | Cl |
| Et | Br | Cl | Cl | Cl |
| i-Pr | Br | Cl | Cl | Cl |
| t-Bu | Br | Cl | Cl | Cl |
| H | Br | Cl | Cl | Br |
| Me | Br | Cl | Cl | Br |
| Et | Br | Cl | Cl | Br |
| i-Pr | Br | Cl | Cl | Br |
| t-Bu | Br | Cl | Cl | Br |
| H | Br | Cl | Br | F |
| Me | Br | Cl | Br | F |
| Et | Br | Cl | Br | F |
| i-Pr | Br | Cl | Br | F |
| t-Bu | Br | Cl | Br | F |
| H | Br | Cl | Br | Cl |
| Me | Br | Cl | Br | Cl |
| Et | Br | Cl | Br | Cl |

TABLE 9-continued

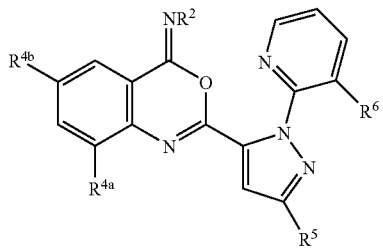

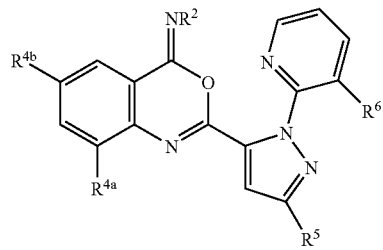

| R² | R⁴ᵃ | R⁴ᵇ | R⁵ | R⁶ |
|---|---|---|---|---|
| i-Pr | Br | Cl | Br | Cl |
| t-Bu | Br | Cl | Br | Cl |
| H | Br | Cl | Br | Br |
| Me | Br | Cl | Br | Br |
| Et | Br | Cl | Br | Br |
| i-Pr | Br | Cl | Br | Br |
| t-Bu | Br | Cl | Br | Br |
| H | Br | Br | CF₃ | F |
| Me | Br | Br | CF₃ | F |
| Et | Br | Br | CF₃ | F |
| i-Pr | Br | Br | CF₃ | F |
| t-Bu | Br | Br | CF₃ | F |
| H | Br | Br | CF₃ | Cl |
| Me | Br | Br | CF₃ | Cl |
| Et | Br | Br | CF₃ | Cl |
| i-Pr | Br | Br | CF₃ | Cl |
| t-Bu | Br | Br | CF₃ | Cl |
| H | Br | Br | CF₃ | Br |
| Me | Br | Br | CF₃ | Br |
| Et | Br | Br | CF₃ | Br |
| i-Pr | Br | Br | CF₃ | Br |
| t-Bu | Br | Br | CF₃ | Br |
| H | Br | Br | Cl | F |
| Me | Br | Br | Cl | F |
| Et | Br | Br | Cl | F |
| i-Pr | Br | Br | Cl | F |
| t-Bu | Br | Br | Cl | F |
| H | Br | Br | Cl | Cl |
| Me | Br | Br | Cl | Cl |
| Et | Br | Br | Cl | Cl |
| i-Pr | Br | Br | Cl | Cl |
| t-Bu | Br | Br | Cl | Cl |
| H | Br | Br | Cl | Br |
| Me | Br | Br | Cl | Br |
| Et | Br | Br | Cl | Br |
| i-Pr | Br | Br | Cl | Br |
| t-Bu | Br | Br | Cl | Br |
| H | Br | Br | Br | F |
| Me | Br | Br | Br | F |
| Et | Br | Br | Br | F |
| i-Pr | Br | Br | Br | F |
| t-Bu | Br | Br | Br | F |
| H | Br | Br | Br | Cl |
| Me | Br | Br | Br | Cl |
| Et | Br | Br | Br | Cl |
| i-Pr | Br | Br | Br | Cl |
| t-Bu | Br | Br | Br | Cl |
| H | Br | Br | Br | Br |
| Me | Br | Br | Br | Br |
| Et | Br | Br | Br | Br |
| i-Pr | Br | Br | Br | Br |
| t-Bu | Br | Br | Br | Br |
| H | Br | I | CF₃ | F |
| Me | Br | I | CF₃ | F |
| Et | Br | I | CF₃ | F |
| i-Pr | Br | I | CF₃ | F |
| t-Bu | Br | I | CF₃ | F |
| H | Br | I | CF₃ | Cl |
| Me | Br | I | CF₃ | Cl |
| Et | Br | I | CF₃ | Cl |
| i-Pr | Br | I | CF₃ | Cl |
| t-Bu | Br | I | CF₃ | Cl |
| H | Br | I | CF₃ | Br |
| Me | Br | I | CF₃ | Br |
| Et | Br | I | CF₃ | Br |
| i-Pr | Br | I | CF₃ | Br |
| t-Bu | Br | I | CF₃ | Br |
| H | Br | I | Cl | F |
| Me | Br | I | Cl | F |
| Et | Br | I | Cl | F |
| i-Pr | Br | I | Cl | F |
| t-Bu | Br | I | Cl | F |
| H | Br | I | Cl | Cl |
| Me | Br | I | Cl | Cl |
| Et | Br | I | Cl | Cl |
| i-Pr | Br | I | Cl | Cl |
| t-Bu | Br | I | Cl | Cl |
| H | Br | I | Cl | Br |
| Me | Br | I | Cl | Br |
| Et | Br | I | Cl | Br |
| i-Pr | Br | I | Cl | Br |
| t-Bu | Br | I | Cl | Br |
| H | Br | I | Br | F |
| Me | Br | I | Br | F |
| Et | Br | I | Br | F |
| i-Pr | Br | I | Br | F |
| t-Bu | Br | I | Br | F |
| H | Br | I | Br | Cl |
| Me | Br | I | Br | Cl |
| Et | Br | I | Br | Cl |
| i-Pr | Br | I | Br | Cl |
| t-Bu | Br | I | Br | Cl |
| H | Br | I | Br | Br |
| Me | Br | I | Br | Br |
| Et | Br | I | Br | Br |
| i-Pr | Br | I | Br | Br |
| t-Bu | Br | I | Br | Br |
| H | Br | CF₃ | CF₃ | F |
| Me | Br | CF₃ | CF₃ | F |
| Et | Br | CF₃ | CF₃ | F |
| i-Pr | Br | CF₃ | CF₃ | F |
| t-Bu | Br | CF₃ | CF₃ | F |
| H | Br | CF₃ | CF₃ | Cl |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| H | Br | CF₃ | CF₃ | Br |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| H | Br | CF₃ | Cl | F |
| Me | Br | CF₃ | Cl | F |
| Et | Br | CF₃ | Cl | F |
| i-Pr | Br | CF₃ | Cl | F |
| t-Bu | Br | CF₃ | Cl | F |
| H | Br | CF₃ | Cl | Cl |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| H | Br | CF₃ | Cl | Br |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| H | Br | CF₃ | Br | F |

TABLE 9-continued

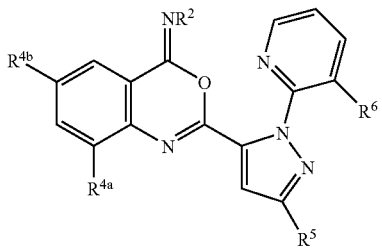

| R² | R⁴ᵃ | R⁴ᵇ | R⁵ | R⁶ |
|---|---|---|---|---|
| Me | Br | CF₃ | Br | F |
| Et | Br | CF₃ | Br | F |
| i-Pr | Br | CF₃ | Br | F |
| t-Bu | Br | CF₃ | Br | F |
| H | Br | CF₃ | Br | Cl |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| H | Br | CF₃ | Br | Br |
| Me | Br | CF₃ | Br | Br |
| Et | Br | CF₃ | Br | Br |
| i-Pr | Br | CF₃ | Br | Br |
| t-Bu | Br | CF₃ | Br | Br |

TABLE 10

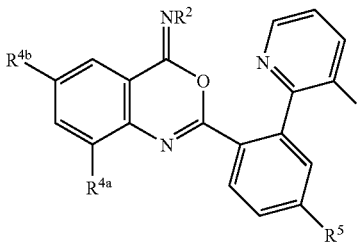

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |

TABLE 10-continued

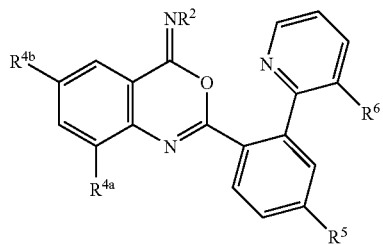

| R² | R⁴ᵃ | R⁴ᵇ | R⁵ | R⁶ |
|---|---|---|---|---|
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |

TABLE 10-continued

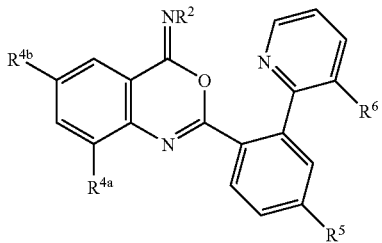

| R² | R⁴ᵃ | R⁴ᵇ | R⁵ | R⁶ |
|---|---|---|---|---|
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Br |
| Et | CH₃ | CF₃ | Br | Br |
| i-Pr | CH₃ | CF₃ | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| t-Bu | Cl | Br | CF₃ | Br |
| Me | Cl | Br | Cl | Cl |
| Et | Cl | Br | Cl | Cl |
| i-Pr | Cl | Br | Cl | Cl |
| t-Bu | Cl | Br | Cl | Cl |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |

TABLE 10-continued

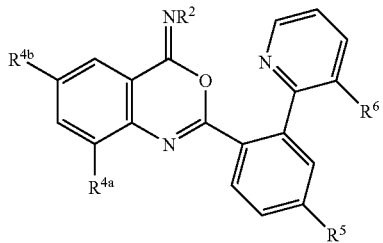

| R² | R⁴ᵃ | R⁴ᵇ | R⁵ | R⁶ |
|---|---|---|---|---|
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | Br | CF₃ | Cl |
| Et | Br | Br | CF₃ | Cl |
| i-Pr | Br | Br | CF₃ | Cl |
| t-Bu | Br | Br | CF₃ | Cl |
| Me | Br | Br | CF₃ | Br |
| Et | Br | Br | CF₃ | Br |
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| n-Pr | CH₃ | Cl | Cl | Cl |
| n-Bu | CH₃ | Cl | Cl | Cl |
| s-Bu | CH₃ | Cl | Cl | Cl |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |

TABLE 10-continued

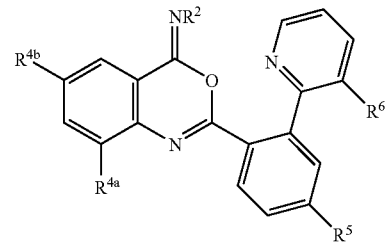

| R² | R⁴ᵃ | R⁴ᵇ | R⁵ | R⁶ |
|---|---|---|---|---|
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| i-Pr | Cl | H | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| i-Pr | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |

TABLE 10-continued

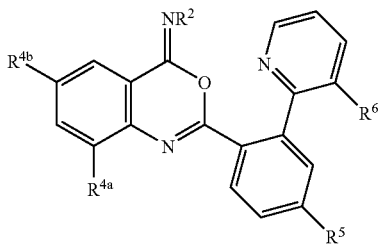

| R² | R⁴ᵃ | R⁴ᵇ | R⁵ | R⁶ |
|---|---|---|---|---|
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |

TABLE 10-continued

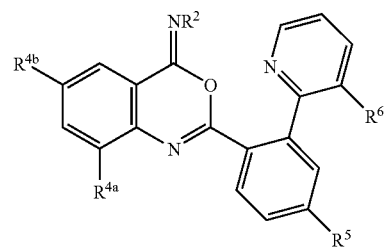

| R² | R⁴ᵃ | R⁴ᵇ | R⁵ | R⁶ |
|---|---|---|---|---|
| t-Bu | CH₃ | CF₃ | Br | Br |
| i-Bu | CH₃ | Cl | Cl | Cl |

TABLE 11

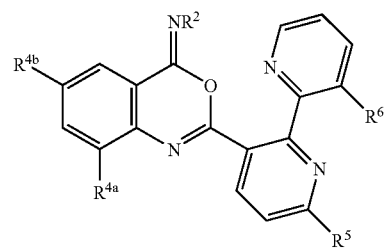

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |

TABLE 11-continued

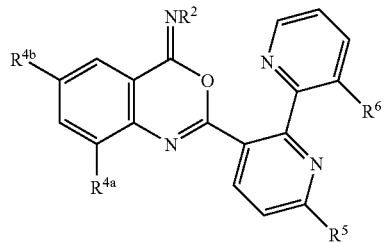

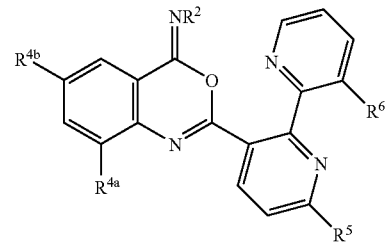

| R² | R⁴ᵃ | R⁴ᵇ | R⁵ | R⁶ |
|---|---|---|---|---|
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Br |
| Et | CH₃ | CF₃ | Br | Br |
| i-Pr | CH₃ | CF₃ | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |

TABLE 11-continued

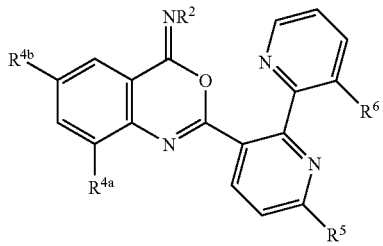

| R² | R⁴ᵃ | R⁴ᵇ | R⁵ | R⁶ |
|---|---|---|---|---|
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| t-Bu | Cl | Br | CF₃ | Br |
| Me | Cl | Br | Cl | Cl |
| Et | Cl | Br | Cl | Cl |
| i-Pr | Cl | Br | Cl | Cl |
| t-Bu | Cl | Br | Cl | Cl |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Br | CF₃ | CF₃ | Cl |
| Et | Br | CF₃ | CF₃ | Cl |
| i-Pr | Br | CF₃ | CF₃ | Cl |

TABLE 11-continued

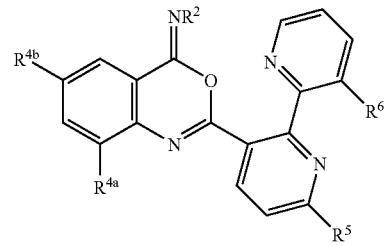

| R² | R⁴ᵃ | R⁴ᵇ | R⁵ | R⁶ |
|---|---|---|---|---|
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | Br | CF₃ | Cl |
| Et | Br | Br | CF₃ | Cl |
| i-Pr | Br | Br | CF₃ | Cl |
| t-Bu | Br | Br | CF₃ | Cl |
| Me | Br | Br | CF₃ | Br |
| Et | Br | Br | CF₃ | Br |
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| n-Pr | CH₃ | Cl | Cl | Cl |
| n-Bu | CH₃ | Cl | Cl | Cl |
| s-Bu | CH₃ | Cl | Cl | Cl |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |

TABLE 11-continued

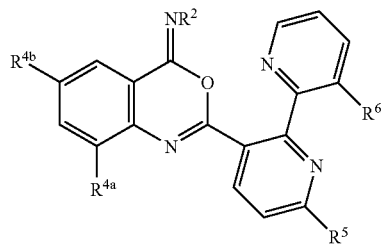

| R² | R⁴ᵃ | R⁴ᵇ | R⁵ | R⁶ |
|---|---|---|---|---|
| Me | Cl | H | Cl | Cl |
| Et | Cl | H | Cl | Cl |
| i-Pr | Cl | H | Cl | Cl |
| i-Pr | Cl | H | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| i-Pr | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |

TABLE 11-continued

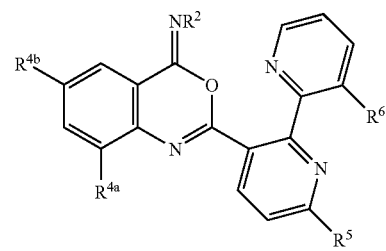

| R² | R⁴ᵃ | R⁴ᵇ | R⁵ | R⁶ |
|---|---|---|---|---|
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| t-Bu | CH₃ | CF₃ | Br | Br |
| i-Bu | CH₃ | Cl | Cl | Cl |

TABLE 12

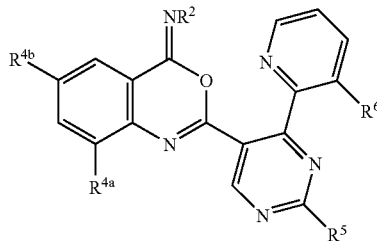

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |

TABLE 12-continued

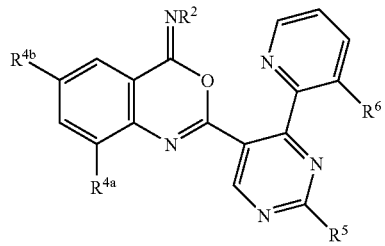

| R² | R⁴ᵃ | R⁴ᵇ | R⁵ | R⁶ |
|---|---|---|---|---|
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Br |
| Et | CH₃ | CF₃ | Br | Br |
| i-Pr | CH₃ | CF₃ | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |

TABLE 12-continued

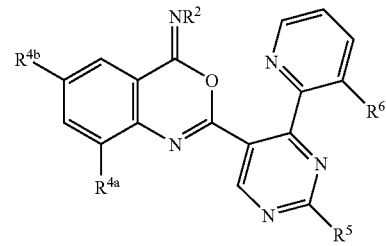

| R² | R⁴ᵃ | R⁴ᵇ | R⁵ | R⁶ |
|---|---|---|---|---|
| Et | Cl | Br | CF₃ | Br |
| i-Pr | Cl | Br | CF₃ | Br |
| t-Bu | Cl | Br | CF₃ | Br |
| Me | Cl | Br | Cl | Cl |
| Et | Cl | Br | Cl | Cl |
| i-Pr | Cl | Br | Cl | Cl |
| t-Bu | Cl | Br | Cl | Cl |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | Br | CF₃ | Cl |

TABLE 12-continued

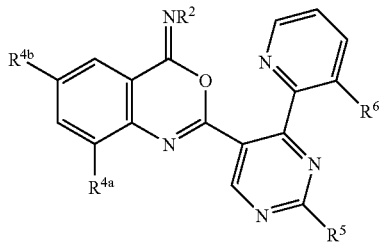

| R² | R⁴ᵃ | R⁴ᵇ | R⁵ | R⁶ |
|---|---|---|---|---|
| Et | Br | Br | CF₃ | Cl |
| i-Pr | Br | Br | CF₃ | Cl |
| t-Bu | Br | Br | CF₃ | Cl |
| Me | Br | Br | CF₃ | Br |
| Et | Br | Br | CF₃ | Br |
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| n-Pr | CH₃ | Cl | Cl | Cl |
| n-Bu | CH₃ | Cl | Cl | Cl |
| s-Bu | CH₃ | Cl | Cl | Cl |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| i-Pr | Cl | H | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| i-Pr | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |

TABLE 12-continued

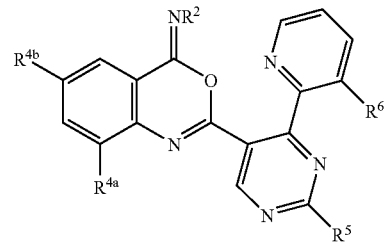

| R² | R⁴ᵃ | R⁴ᵇ | R⁵ | R⁶ |
|---|---|---|---|---|
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |

TABLE 12-continued

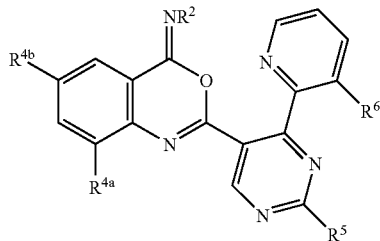

| R² | R⁴ᵃ | R⁴ᵇ | R⁵ | R⁶ |
|---|---|---|---|---|
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| t-Bu | CH₃ | CF₃ | Br | Br |
| i-Bu | CH₃ | Cl | Cl | Cl |

TABLE 13

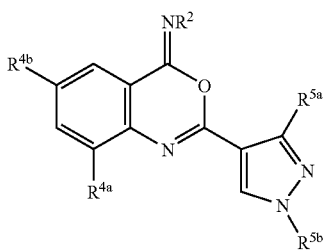

| R² | R⁴ᵃ | R⁴ᵇ | R⁵ᵃ |
|---|---|---|---|
| R⁵ᵇ is CHF₂ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |

TABLE 13-continued

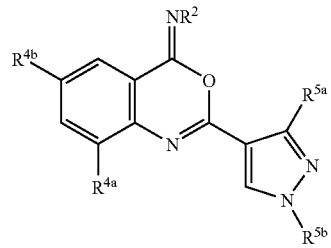

| R² | R⁴ᵃ | R⁴ᵇ | R⁵ᵃ |
|---|---|---|---|
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R⁵ᵇ is CH₂CF₃ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R⁵ᵇ is CF₂CHF₂ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |

TABLE 13-continued

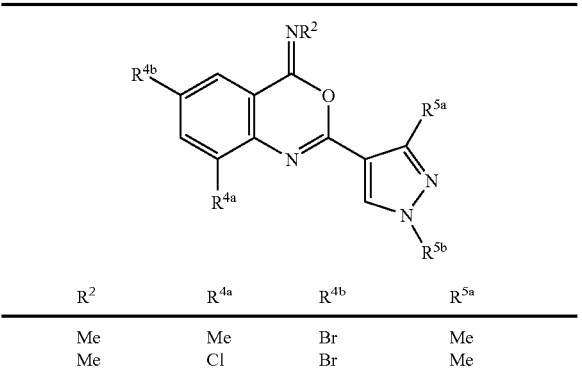

| R² | R⁴ᵃ | R⁴ᵇ | R⁵ᵃ |
|---|---|---|---|
| Me | Me | Br | Me |
| Me | Cl | Br | Me |

TABLE 14

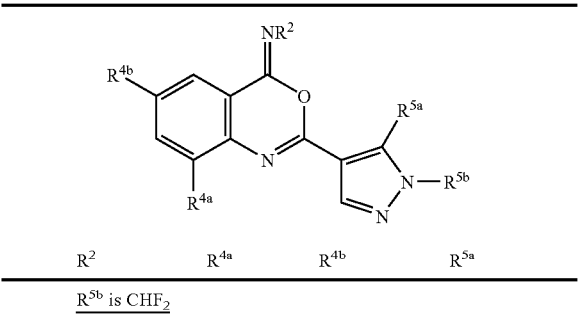

| R² | R⁴ᵃ | R⁴ᵇ | R⁵ᵃ |
|---|---|---|---|
| R⁵ᵇ is CHF₂ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R⁵ᵇ is CH₂CF₃ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |

TABLE 14-continued

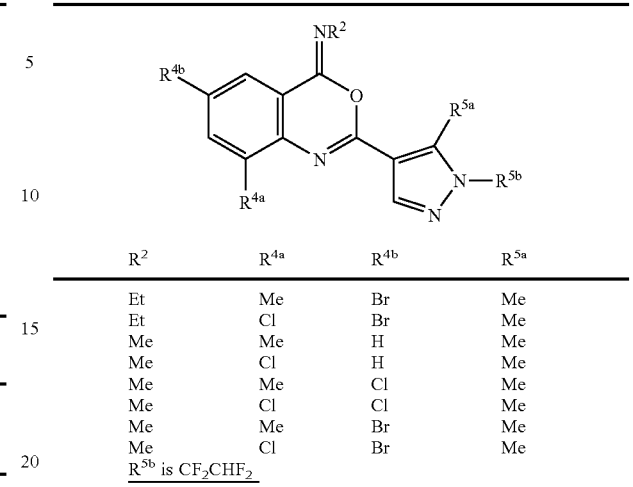

| R² | R⁴ᵃ | R⁴ᵇ | R⁵ᵃ |
|---|---|---|---|
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |
| R⁵ᵇ is CF₂CHF₂ | | | |
| i-Pr | Me | H | Me |
| i-Pr | Cl | H | Me |
| i-Pr | Me | Cl | Me |
| i-Pr | Cl | Cl | Me |
| i-Pr | Me | Br | Me |
| i-Pr | Cl | Br | Me |
| t-Bu | Me | H | Me |
| t-Bu | Cl | H | Me |
| t-Bu | Me | Cl | Me |
| t-Bu | Cl | Cl | Me |
| t-Bu | Me | Br | Me |
| t-Bu | Cl | Br | Me |
| Et | Me | H | Me |
| Et | Cl | H | Me |
| Et | Me | Cl | Me |
| Et | Cl | Cl | Me |
| Et | Me | Br | Me |
| Et | Cl | Br | Me |
| Me | Me | H | Me |
| Me | Cl | H | Me |
| Me | Me | Cl | Me |
| Me | Cl | Cl | Me |
| Me | Me | Br | Me |
| Me | Cl | Br | Me |

TABLE 15

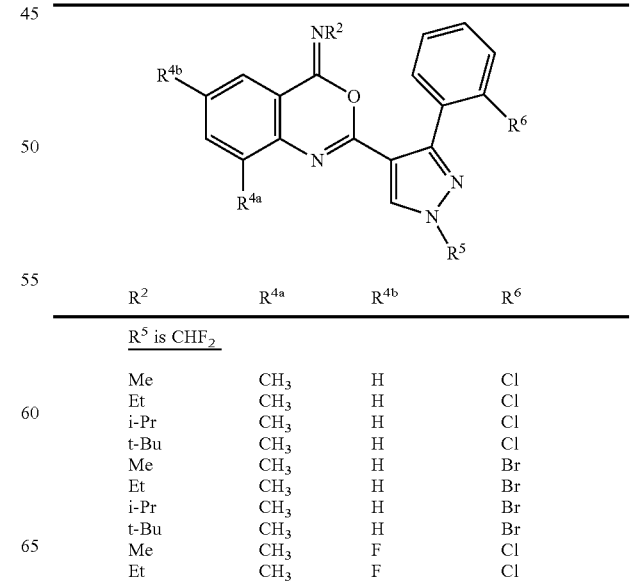

| R² | R⁴ᵃ | R⁴ᵇ | R⁶ |
|---|---|---|---|
| R⁵ is CHF₂ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |

TABLE 15-continued

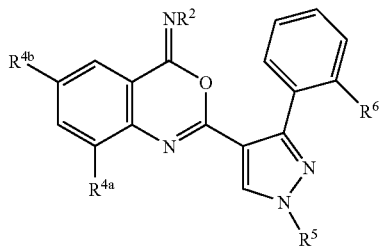

| R² | R⁴ᵃ | R⁴ᵇ | R⁶ |
|---|---|---|---|
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| n-Pr | CH₃ | Cl | Cl |
| n-Bu | CH₃ | Cl | Cl |
| s-Bu | CH₃ | Cl | Cl |
| i-Bu | CH₃ | Cl | Cl |
| Me | Cl | F | Cl |
| Et | Cl | F | Cl |
| i-Pr | Cl | F | Cl |
| t-Bu | Cl | F | Cl |
| Me | Cl | F | Br |
| Et | Cl | F | Br |
| i-Pr | Cl | F | Br |
| t-Bu | Cl | F | Br |
| Me | Cl | Cl | Cl |
| Et | Cl | Cl | Cl |
| i-Pr | Cl | Cl | Cl |
| t-Bu | Cl | Cl | Cl |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | Br | Br |
| Et | Cl | Br | Br |

TABLE 15-continued

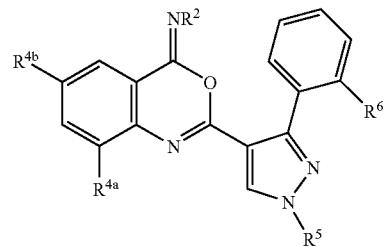

| R² | R⁴ᵃ | R⁴ᵇ | R⁶ |
|---|---|---|---|
| i-Pr | Cl | Br | Br |
| t-Bu | Cl | Br | Br |
| Me | Cl | Br | Cl |
| Et | Cl | Br | Cl |
| i-Pr | Cl | Br | Cl |
| t-Bu | Cl | Br | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |

R⁵ is CH₂CHF₃

| R² | R⁴ᵃ | R⁴ᵇ | R⁶ |
|---|---|---|---|
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |

TABLE 15-continued

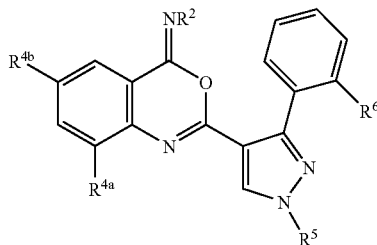

| R² | R⁴ᵃ | R⁴ᵇ | R⁶ |
|---|---|---|---|
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |

TABLE 15-continued

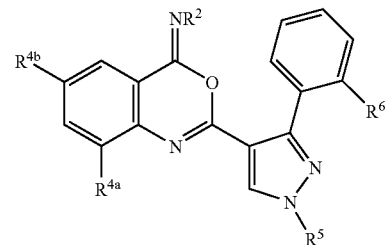

| R² | R⁴ᵃ | R⁴ᵇ | R⁶ |
|---|---|---|---|
| Me | Cl | Br | Br |
| Et | Cl | Br | Br |
| i-Pr | Cl | Br | Br |
| t-Bu | Cl | Br | Br |
| Me | Cl | I | Cl |
| Et | Cl | I | Cl |
| i-Pr | Cl | I | Cl |
| t-Bu | Cl | I | Cl |
| Me | Cl | I | Br |
| Et | Cl | I | Br |
| i-Pr | Cl | I | Br |
| t-Bu | Cl | I | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Cl | CF₃ | Br |
| Et | Cl | CF₃ | Br |
| i-Pr | Cl | CF₃ | Br |
| t-Bu | Cl | CF₃ | Br |
| n-Pr | CH₃ | Cl | Cl |
| n-Bu | CH₃ | Cl | Cl |
| s-Bu | CH₃ | Cl | Cl |
| i-Bu | CH₃ | Cl | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |

R⁵ is CF₂CHF₂

| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |

TABLE 15-continued

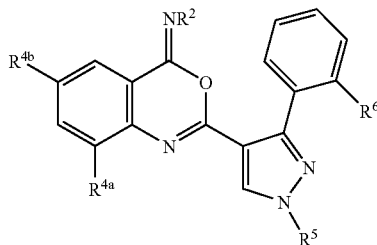

| R² | R⁴ᵃ | R⁴ᵇ | R⁶ |
|---|---|---|---|
| i-Pr | CH₃ | H | Br |
| t-Bu | CH₃ | H | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | F | Br |
| Et | Cl | F | Br |
| i-Pr | Cl | F | Br |
| t-Bu | Cl | F | Br |

TABLE 15-continued

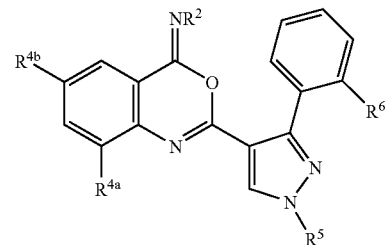

| R² | R⁴ᵃ | R⁴ᵇ | R⁶ |
|---|---|---|---|
| Me | Cl | F | Cl |
| Et | Cl | F | Cl |
| i-Pr | Cl | F | Cl |
| t-Bu | Cl | F | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |
| Me | Br | CF₃ | Cl |
| Et | Br | CF₃ | Cl |
| i-Pr | Br | CF₃ | Cl |
| t-Bu | Br | CF₃ | Cl |
| Me | Br | CF₃ | Br |
| Et | Br | CF₃ | Br |
| i-Pr | Br | CF₃ | Br |
| t-Bu | Br | CF₃ | Br |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |

TABLE 16

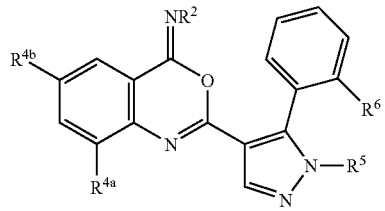

| $R^2$ | $R^{4a}$ | $R^{4b}$ | $R^6$ |
|---|---|---|---|
| $R^5$ is $CHF_2$ | | | |
| Me | $CH_3$ | H | Cl |
| Et | $CH_3$ | H | Cl |
| i-Pr | $CH_3$ | H | Cl |
| t-Bu | $CH_3$ | H | Cl |
| Me | $CH_3$ | H | Br |
| Et | $CH_3$ | H | Br |
| i-Pr | $CH_3$ | H | Br |
| t-Bu | $CH_3$ | H | Br |
| Me | $CH_3$ | F | Cl |
| Et | $CH_3$ | F | Cl |
| i-Pr | $CH_3$ | F | Cl |
| t-Bu | $CH_3$ | F | Cl |
| Me | $CH_3$ | F | Br |
| Et | $CH_3$ | F | Br |
| i-Pr | $CH_3$ | F | Br |
| t-Bu | $CH_3$ | F | Br |
| Me | $CH_3$ | Cl | Cl |
| Et | $CH_3$ | Cl | Cl |
| i-Pr | $CH_3$ | Cl | Cl |
| t-Bu | $CH_3$ | Cl | Cl |
| Me | $CH_3$ | Cl | Br |
| Et | $CH_3$ | Cl | Br |
| i-Pr | $CH_3$ | Cl | Br |
| t-Bu | $CH_3$ | Cl | Br |
| Me | $CH_3$ | Br | Cl |
| Et | $CH_3$ | Br | Cl |
| i-Pr | $CH_3$ | Br | Cl |
| t-Bu | $CH_3$ | Br | Cl |
| Me | $CH_3$ | Br | Br |
| Et | $CH_3$ | Br | Br |
| i-Pr | $CH_3$ | Br | Br |
| t-Bu | $CH_3$ | Br | Br |
| Me | $CH_3$ | I | Cl |
| Et | $CH_3$ | I | Cl |
| i-Pr | $CH_3$ | I | Cl |
| t-Bu | $CH_3$ | I | Cl |
| Me | $CH_3$ | I | Br |
| Et | $CH_3$ | I | Br |
| i-Pr | $CH_3$ | I | Br |
| t-Bu | $CH_3$ | I | Br |
| Me | $CH_3$ | $CF_3$ | Cl |
| Et | $CH_3$ | $CF_3$ | Cl |
| i-Pr | $CH_3$ | $CF_3$ | Cl |
| t-Bu | $CH_3$ | $CF_3$ | Cl |
| Me | $CH_3$ | $CF_3$ | Br |
| Et | $CH_3$ | $CF_3$ | Br |
| i-Pr | $CH_3$ | $CF_3$ | Br |
| t-Bu | $CH_3$ | $CF_3$ | Br |
| n-Pr | $CH_3$ | Cl | Cl |
| n-Bu | $CH_3$ | Cl | Cl |
| s-Bu | $CH_3$ | Cl | Cl |
| i-Bu | $CH_3$ | Cl | Cl |
| Me | Cl | F | Cl |
| Et | Cl | F | Cl |
| i-Pr | Cl | F | Cl |
| t-Bu | Cl | F | Cl |
| Me | Cl | F | Br |
| Et | Cl | F | Br |
| i-Pr | Cl | F | Br |
| t-Bu | Cl | F | Br |
| Me | Cl | Cl | Cl |
| Et | Cl | Cl | Cl |
| i-Pr | Cl | Cl | Cl |
| t-Bu | Cl | Cl | Cl |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | Br | Br |
| Et | Cl | Br | Br |
| i-Pr | Cl | Br | Br |
| t-Bu | Cl | Br | Br |
| Me | Cl | Br | Cl |
| Et | Cl | Br | Cl |
| i-Pr | Cl | Br | Cl |
| t-Bu | Cl | Br | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | $CF_3$ | Br |
| Et | Cl | $CF_3$ | Br |
| i-Pr | Cl | $CF_3$ | Br |
| t-Bu | Cl | $CF_3$ | Br |
| Me | Cl | $CF_3$ | Cl |
| Et | Cl | $CF_3$ | Cl |
| i-Pr | Cl | $CF_3$ | Cl |
| t-Bu | Cl | $CF_3$ | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |

TABLE 16-continued

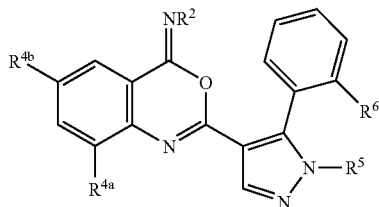

| R² | R⁴ᵃ | R⁴ᵇ | R⁶ |
|---|---|---|---|
| R⁵ is CH₂CHF₃ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |

TABLE 16-continued

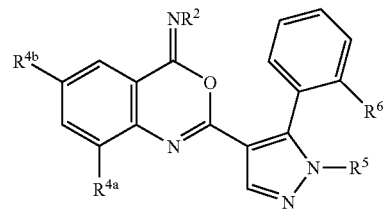

| R² | R⁴ᵃ | R⁴ᵇ | R⁶ |
|---|---|---|---|
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | Br | Br |
| Et | Cl | Br | Br |
| i-Pr | Cl | Br | Br |
| t-Bu | Cl | Br | Br |
| Me | Cl | I | Cl |
| Et | Cl | I | Cl |
| i-Pr | Cl | I | Cl |
| t-Bu | Cl | I | Cl |
| Me | Cl | I | Br |
| Et | Cl | I | Br |
| i-Pr | Cl | I | Br |
| t-Bu | Cl | I | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Cl | CF₃ | Br |
| Et | Cl | CF₃ | Br |
| i-Pr | Cl | CF₃ | Br |
| t-Bu | Cl | CF₃ | Br |
| n-Pr | Cl | Cl | Cl |
| n-Bu | Cl | Cl | Cl |
| s-Bu | Cl | Cl | Cl |
| i-Bu | Cl | Cl | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |

TABLE 16-continued

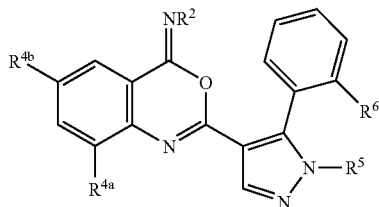

| R² | R⁴ᵃ | R⁴ᵇ | R⁶ |
|---|---|---|---|
| R⁵ is CF₂CHF₂ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |

TABLE 16-continued

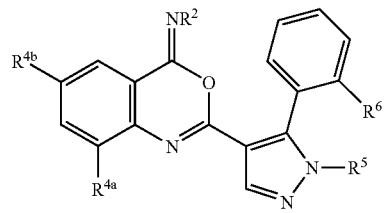

| R² | R⁴ᵃ | R⁴ᵇ | R⁶ |
|---|---|---|---|
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |
| Me | Br | CF₃ | Cl |
| Et | Br | CF₃ | Cl |
| i-Pr | Br | CF₃ | Cl |
| t-Bu | Br | CF₃ | Cl |
| Me | Br | CF₃ | Br |
| Et | Br | CF₃ | Br |
| i-Pr | Br | CF₃ | Br |
| t-Bu | Br | CF₃ | Br |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |

TABLE 17

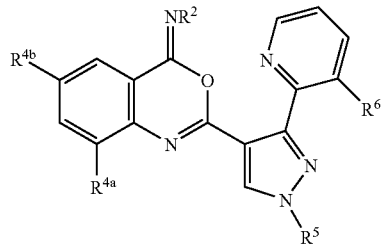

| R² | R⁴ᵃ | R⁴ᵇ | R⁶ |
|---|---|---|---|
| R⁵ is CHF₂ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| n-Pr | CH₃ | Cl | Cl |
| n-Bu | CH₃ | Cl | Cl |
| s-Bu | CH₃ | Cl | Cl |
| i-Bu | CH₃ | Cl | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | H | Br |
| Et | Cl | H | Br |

TABLE 17-continued

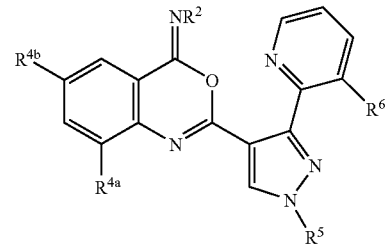

| R² | R⁴ᵃ | R⁴ᵇ | R⁶ |
|---|---|---|---|
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Cl | Br | Br |
| Et | Cl | Br | Br |
| i-Pr | Cl | Br | Br |
| t-Bu | Cl | Br | Br |
| Me | Cl | Br | Cl |
| Et | Cl | Br | Cl |
| i-Pr | Cl | Br | Cl |
| t-Bu | Cl | Br | Cl |
| Me | Cl | F | Br |
| Et | Cl | F | Br |
| i-Pr | Cl | F | Br |
| t-Bu | Cl | F | Br |
| Me | Cl | Cl | Cl |
| Et | Cl | Cl | Cl |
| i-Pr | Cl | Cl | Cl |
| t-Bu | Cl | Cl | Cl |
| Me | Cl | F | Cl |
| Et | Cl | F | Cl |
| i-Pr | Cl | F | Cl |
| t-Bu | Cl | F | Cl |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |

TABLE 17-continued

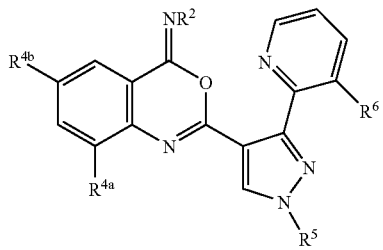

| R² | R⁴ᵃ | R⁴ᵇ | R⁶ |
|---|---|---|---|
| i-Pr | Br | Cl | Br |
| t-Bu | Br | Cl | Br |
| R⁵ is CH₂CHF₃ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | Cl | Br |
| Et | Cl | Cl | Br |
| i-Pr | Cl | Cl | Br |
| t-Bu | Cl | Cl | Br |

TABLE 17-continued

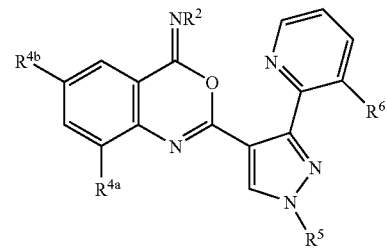

| R² | R⁴ᵃ | R⁴ᵇ | R⁶ |
|---|---|---|---|
| Me | Cl | Cl | Cl |
| Et | Cl | Cl | Cl |
| i-Pr | Cl | Cl | Cl |
| t-Bu | Cl | Cl | Cl |
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | Br | Br |
| Et | Cl | Br | Br |
| i-Pr | Cl | Br | Br |
| t-Bu | Cl | Br | Br |
| Me | Cl | I | Cl |
| Et | Cl | I | Cl |
| i-Pr | Cl | I | Cl |
| t-Bu | Cl | I | Cl |
| Me | Cl | I | Br |
| Et | Cl | I | Br |
| i-Pr | Cl | I | Br |
| t-Bu | Cl | I | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Cl | CF₃ | Br |
| Et | Cl | CF₃ | Br |
| i-Pr | Cl | CF₃ | Br |
| t-Bu | Cl | CF₃ | Br |
| n-Pr | Cl | Cl | Cl |
| n-Bu | Cl | Cl | Cl |
| s-Bu | Cl | Cl | Cl |
| i-Bu | Cl | Cl | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |
| Me | Br | Br | Cl |
| Et | Br | Br | Cl |
| i-Pr | Br | Br | Cl |
| t-Bu | Br | Br | Cl |

TABLE 17-continued

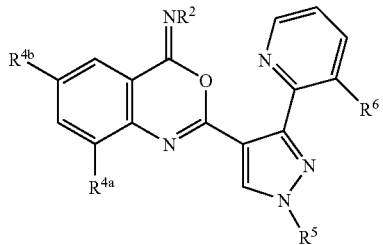

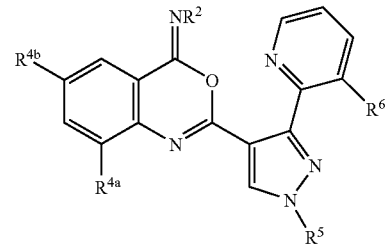

| R² | R⁴ᵃ | R⁴ᵇ | R⁶ |
|---|---|---|---|
| Me | Br | Br | Br |
| Et | Br | Br | Br |
| i-Pr | Br | Br | Br |
| t-Bu | Br | Br | Br |
| R⁵ is CF₂CHF₂ | | | |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| Me | Br | CF₃ | Cl |
| Et | Br | CF₃ | Cl |
| i-Pr | Br | CF₃ | Cl |
| t-Bu | Br | CF₃ | Cl |
| Me | Br | CF₃ | Br |
| Et | Br | CF₃ | Br |
| i-Pr | Br | CF₃ | Br |
| t-Bu | Br | CF₃ | Br |
| Me | Br | I | Cl |
| Et | Br | I | Cl |

TABLE 17-continued

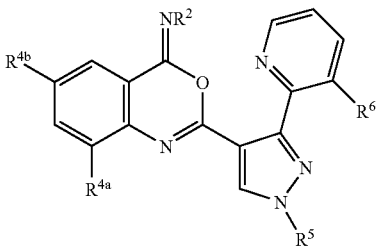

| R² | R⁴ᵃ | R⁴ᵇ | R⁶ |
|---|---|---|---|
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |

TABLE 18

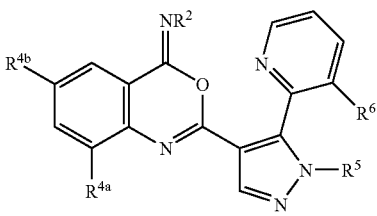

| R² | R⁴ᵃ | R⁴ᵇ | R⁶ |
|---|---|---|---|
| R⁵ is CHF₂ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |

TABLE 18-continued

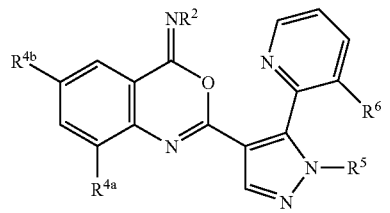

| R² | R⁴ᵃ | R⁴ᵇ | R⁶ |
|---|---|---|---|
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| n-Pr | CH₃ | Cl | Cl |
| n-Bu | CH₃ | Cl | Cl |
| i-Bu | CH₃ | Cl | Cl |
| i-Bu | CH₃ | Cl | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Cl | Br | Br |
| Et | Cl | Br | Br |
| i-Pr | Cl | Br | Br |
| t-Bu | Cl | Br | Br |
| Me | Cl | Br | Cl |
| Et | Cl | Br | Cl |
| i-Pr | Cl | Br | Cl |
| t-Bu | Cl | Br | Cl |
| Me | Cl | F | Br |
| Et | Cl | F | Br |
| i-Pr | Cl | F | Br |
| t-Bu | Cl | F | Br |
| Me | Cl | Cl | Cl |
| Et | Cl | Cl | Cl |
| i-Pr | Cl | Cl | Cl |
| t-Bu | Cl | Cl | Cl |
| Me | Cl | F | Cl |
| Et | Cl | F | Cl |
| i-Pr | Cl | F | Cl |
| t-Bu | Cl | F | Cl |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |

TABLE 18-continued

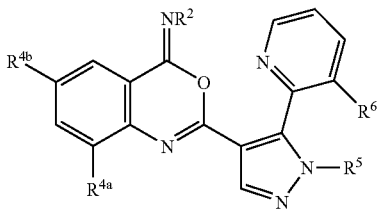

| R² | R⁴ᵃ | R⁴ᵇ | R⁶ |
|---|---|---|---|
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| R⁵ is CH₂F₃ | | | |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | F | Cl |
| Et | CH₃ | F | Cl |
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |

TABLE 18-continued

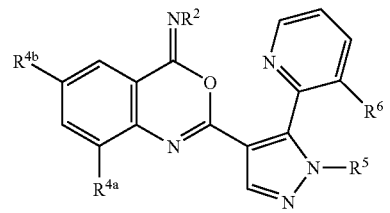

| R² | R⁴ᵃ | R⁴ᵇ | R⁶ |
|---|---|---|---|
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| t-Bu | Cl | H | Cl |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | Br | Br |
| Et | Cl | Br | Br |
| i-Pr | Cl | Br | Br |
| t-Bu | Cl | Br | Br |
| Me | Cl | I | Cl |
| Et | Cl | I | Cl |
| i-Pr | Cl | I | Cl |
| t-Bu | Cl | I | Cl |
| Me | Cl | I | Br |
| Et | Cl | I | Br |
| i-Pr | Cl | I | Br |
| t-Bu | Cl | I | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Cl | CF₃ | Br |
| Et | Cl | CF₃ | Br |
| i-Pr | Cl | CF₃ | Br |
| t-Bu | Cl | CF₃ | Br |
| n-Pr | Cl | Cl | Cl |
| n-Bu | Cl | Cl | Cl |
| s-Bu | Cl | Cl | Cl |
| i-Bu | Cl | Cl | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |

TABLE 18-continued

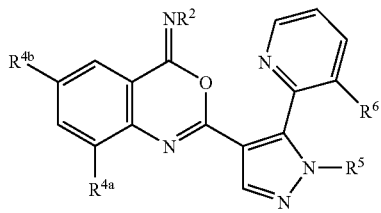

| R² | R⁴ᵃ | R⁴ᵇ | R⁶ |
|---|---|---|---|
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |
| Me | Br | Br | Cl |
| Et | Br | Br | Cl |
| i-Pr | Br | Br | Cl |
| t-Bu | Br | Br | Cl |
| Me | Br | Br | Br |
| Et | Br | Br | Br |
| i-Pr | Br | Br | Br |
| t-Bu | Br | Br | Br |
| R⁵ is CF₂CHF₂ | | | |
| Me | CH₃ | Br | Cl |
| Et | CH₃ | Br | Cl |
| i-Pr | CH₃ | Br | Cl |
| t-Bu | CH₃ | Br | Cl |
| Me | CH₃ | Br | Br |
| Et | CH₃ | Br | Br |
| i-Pr | CH₃ | Br | Br |
| t-Bu | CH₃ | Br | Br |
| Me | CH₃ | I | Cl |
| Et | CH₃ | I | Cl |
| i-Pr | CH₃ | I | Cl |
| t-Bu | CH₃ | I | Cl |
| Me | CH₃ | I | Br |
| Et | CH₃ | I | Br |
| i-Pr | CH₃ | I | Br |
| t-Bu | CH₃ | I | Br |
| Me | CH₃ | CF₃ | Cl |
| Et | CH₃ | CF₃ | Cl |
| i-Pr | CH₃ | CF₃ | Cl |
| t-Bu | CH₃ | CF₃ | Cl |
| Me | CH₃ | CF₃ | Br |
| Et | CH₃ | CF₃ | Br |
| i-Pr | CH₃ | CF₃ | Br |
| t-Bu | CH₃ | CF₃ | Br |
| Me | CH₃ | Cl | Cl |
| Et | CH₃ | Cl | Cl |
| i-Pr | CH₃ | Cl | Cl |
| t-Bu | CH₃ | Cl | Cl |
| Me | CH₃ | Cl | Br |
| Et | CH₃ | Cl | Br |
| i-Pr | CH₃ | Cl | Br |
| t-Bu | CH₃ | Cl | Br |
| Me | CH₃ | H | Cl |
| Et | CH₃ | H | Cl |
| i-Pr | CH₃ | H | Cl |
| t-Bu | CH₃ | H | Cl |
| Me | CH₃ | H | Br |
| Et | CH₃ | H | Br |
| i-Pr | CH₃ | H | Br |
| t-Bu | CH₃ | H | Br |
| Me | CH₃ | F | Cl |
| Et | CH₃ | F | Cl |

TABLE 18-continued

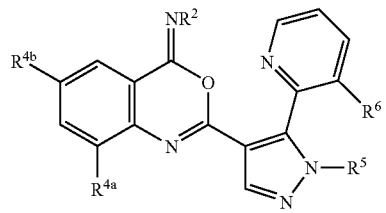

| R² | R⁴ᵃ | R⁴ᵇ | R⁶ |
|---|---|---|---|
| i-Pr | CH₃ | F | Cl |
| t-Bu | CH₃ | F | Cl |
| Me | CH₃ | F | Br |
| Et | CH₃ | F | Br |
| i-Pr | CH₃ | F | Br |
| t-Bu | CH₃ | F | Br |
| Me | Cl | Cl | Br |
| Et | Cl | Cl | Br |
| i-Pr | Cl | Cl | Br |
| t-Bu | Cl | Cl | Br |
| Me | Cl | Cl | Cl |
| Et | Cl | Cl | Cl |
| i-Pr | Cl | Cl | Cl |
| t-Bu | Cl | Cl | Cl |
| Me | Cl | I | Br |
| Et | Cl | I | Br |
| i-Pr | Cl | I | Br |
| t-Bu | Cl | I | Br |
| Me | Cl | I | Cl |
| Et | Cl | I | Cl |
| i-Pr | Cl | I | Cl |
| t-Bu | Cl | I | Cl |
| Me | Cl | F | Br |
| Et | Cl | F | Br |
| i-Pr | Cl | F | Br |
| t-Bu | Cl | F | Br |
| Me | Cl | F | Cl |
| Et | Cl | F | Cl |
| i-Pr | Cl | F | Cl |
| t-Bu | Cl | F | Cl |
| Me | Cl | H | Br |
| Et | Cl | H | Br |
| i-Pr | Cl | H | Br |
| t-Bu | Cl | H | Br |
| Me | Cl | H | Cl |
| Et | Cl | H | Cl |
| i-Pr | Cl | H | Cl |
| i-Pr | Cl | H | Cl |
| Me | Cl | CF₃ | Br |
| Et | Cl | CF₃ | Br |
| i-Pr | Cl | CF₃ | Br |
| t-Bu | Cl | CF₃ | Br |
| Me | Cl | CF₃ | Cl |
| Et | Cl | CF₃ | Cl |
| i-Pr | Cl | CF₃ | Cl |
| t-Bu | Cl | CF₃ | Cl |
| Me | Br | F | Cl |
| Et | Br | F | Cl |
| i-Pr | Br | F | Cl |
| t-Bu | Br | F | Cl |
| Me | Br | F | Br |
| Et | Br | F | Br |
| i-Pr | Br | F | Br |
| t-Bu | Br | F | Br |
| Me | Br | Cl | Cl |
| Et | Br | Cl | Cl |
| i-Pr | Br | Cl | Cl |
| t-Bu | Br | Cl | Cl |
| Me | Br | Cl | Br |
| Et | Br | Cl | Br |
| i-Pr | Br | Cl | Br |
| t-Bu | Br | Cl | Br |
| Me | Br | Br | Cl |
| Et | Br | Br | Cl |
| i-Pr | Br | Br | Cl |
| t-Bu | Br | Br | Cl |

TABLE 18-continued

| R² | R⁴ᵃ | R⁴ᵇ | R⁶ |
|---|---|---|---|
| Me | Br | Br | Br |
| Et | Br | Br | Br |
| i-Pr | Br | Br | Br |
| t-Bu | Br | Br | Br |
| Me | Br | CF₃ | Cl |
| Et | Br | CF₃ | Cl |
| i-Pr | Br | CF₃ | Cl |
| t-Bu | Br | CF₃ | Cl |
| Me | Br | CF₃ | Br |
| Et | Br | CF₃ | Br |
| i-Pr | Br | CF₃ | Br |
| t-Bu | Br | CF₃ | Br |
| Me | Br | I | Cl |
| Et | Br | I | Cl |
| i-Pr | Br | I | Cl |
| t-Bu | Br | I | Cl |
| Me | Br | I | Br |
| Et | Br | I | Br |
| i-Pr | Br | I | Br |
| t-Bu | Br | I | Br |

TABLE 19

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |

TABLE 19-continued

| R² | R⁴ᵃ | R⁴ᵇ | R⁵ | R⁶ |
|---|---|---|---|---|
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |

TABLE 19-continued

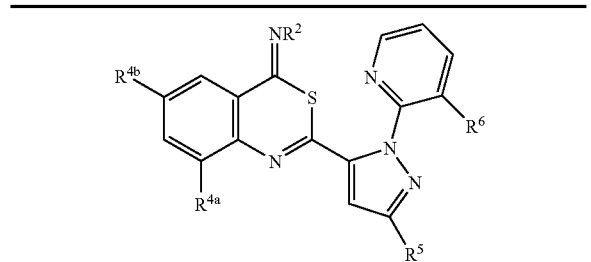
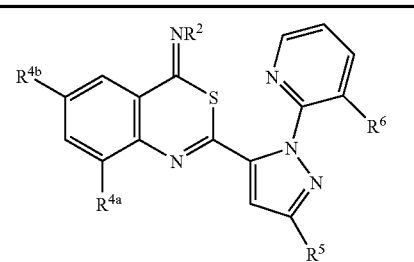

| R² | R⁴ᵃ | R⁴ᵇ | R⁵ | R⁶ |
|---|---|---|---|---|
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Br |
| Et | CH₃ | CF₃ | Br | Br |
| i-Pr | CH₃ | CF₃ | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| t-Bu | Cl | Br | CF₃ | Br |
| Me | Cl | Br | Cl | Cl |
| Et | Cl | Br | Cl | Cl |
| i-Pr | Cl | Br | Cl | Cl |
| t-Bu | Cl | Br | Cl | Cl |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |

TABLE 19-continued

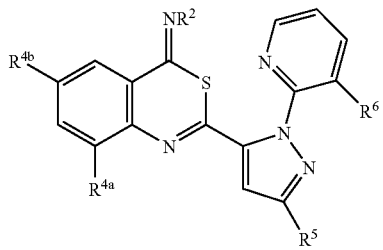

| R² | R⁴ᵃ | R⁴ᵇ | R⁵ | R⁶ |
|---|---|---|---|---|
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |
| Et | Br | CF₃ | Br | Br |
| i-Pr | Br | CF₃ | Br | Br |
| t-Bu | Br | CF₃ | Br | Br |
| Me | Br | Br | CF₃ | Cl |
| Et | Br | Br | CF₃ | Cl |
| i-Pr | Br | Br | CF₃ | Cl |
| t-Bu | Br | Br | CF₃ | Cl |
| Me | Br | Br | CF₃ | Br |
| Et | Br | Br | CF₃ | Br |
| i-Pr | Br | Br | CF₃ | Br |
| t-Bu | Br | Br | CF₃ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | CH₃ | CF₃ | Br | Cl |
| Et | CH₃ | CF₃ | Br | Cl |
| i-Pr | CH₃ | CF₃ | Br | Cl |
| t-Bu | CH₃ | CF₃ | Br | Cl |
| n-Pr | CH₃ | Cl | Cl | Cl |
| n-Bu | CH₃ | Cl | Cl | Cl |
| s-Bu | CH₃ | Cl | Cl | Cl |
| Me | Cl | H | Cl | Br |
| Et | Cl | H | Cl | Br |
| i-Pr | Cl | H | Cl | Br |
| t-Bu | Cl | H | Cl | Br |

TABLE 19-continued

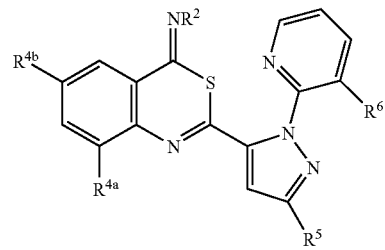

| R² | R⁴ᵃ | R⁴ᵇ | R⁵ | R⁶ |
|---|---|---|---|---|
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF₃ | Cl |
| Et | Cl | H | CF₃ | Cl |
| i-Pr | Cl | H | CF₃ | Cl |
| t-Bu | Cl | H | CF₃ | Cl |
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| t-Bu | Cl | H | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| t-Bu | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |

TABLE 19-continued

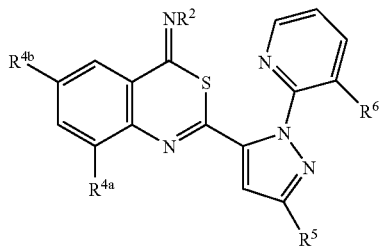

| R² | R⁴ᵃ | R⁴ᵇ | R⁵ | R⁶ |
|---|---|---|---|---|
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |

TABLE 19-continued

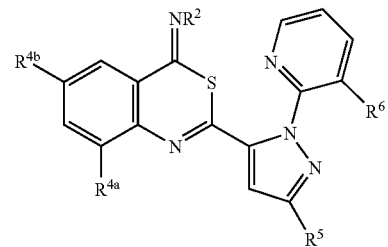

| R² | R⁴ᵃ | R⁴ᵇ | R⁵ | R⁶ |
|---|---|---|---|---|
| Me | Br | Cl | Br | Br |
| Et | Br | Cl | Br | Br |
| i-Pr | Br | Cl | Br | Br |
| t-Bu | Br | Cl | Br | Br |
| t-Bu | CH₃ | CF₃ | Br | Br |
| i-Bu | CH₃ | Cl | Cl | Cl |

TABLE 20

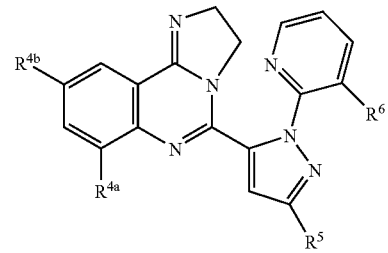

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |

TABLE 20-continued

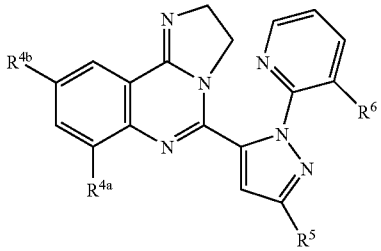

| R² | R⁴ᵃ | R⁴ᵇ | R⁵ | R⁶ |
|---|---|---|---|---|
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |

TABLE 20-continued

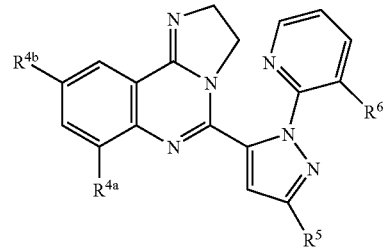

| R² | R⁴ᵃ | R⁴ᵇ | R⁵ | R⁶ |
|---|---|---|---|---|
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Br |
| Et | CH₃ | CF₃ | Br | Br |
| i-Pr | CH₃ | CF₃ | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |

TABLE 20-continued

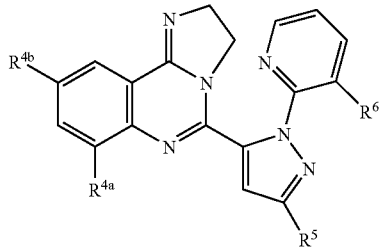

| $R^2$ | $R^{4a}$ | $R^{4b}$ | $R^5$ | $R^6$ |
|---|---|---|---|---|
| t-Bu | Cl | Cl | CF$_3$ | Cl |
| Me | Cl | Cl | CF$_3$ | Br |
| Et | Cl | Cl | CF$_3$ | Br |
| i-Pr | Cl | Cl | CF$_3$ | Br |
| t-Bu | Cl | Cl | CF$_3$ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF$_3$ | Cl |
| Et | Cl | Br | CF$_3$ | Cl |
| i-Pr | Cl | Br | CF$_3$ | Cl |
| t-Bu | Cl | Br | CF$_3$ | Cl |
| Me | Cl | Br | CF$_3$ | Br |
| Et | Cl | Br | CF$_3$ | Br |
| i-Pr | Cl | Br | CF$_3$ | Br |
| t-Bu | Cl | Br | CF$_3$ | Br |
| Me | Cl | Br | Cl | Cl |
| Et | Cl | Br | Cl | Cl |
| i-Pr | Cl | Br | Cl | Cl |
| t-Bu | Cl | Br | Cl | Cl |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| Me | Br | I | CF$_3$ | Cl |
| Et | Br | I | CF$_3$ | Cl |
| i-Pr | Br | I | CF$_3$ | Cl |
| t-Bu | Br | I | CF$_3$ | Cl |
| Me | Br | I | CF$_3$ | Br |
| Et | Br | I | CF$_3$ | Br |
| i-Pr | Br | I | CF$_3$ | Br |
| t-Bu | Br | I | CF$_3$ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |

TABLE 20-continued

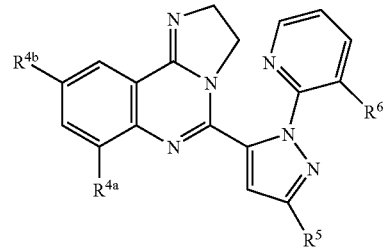

| $R^2$ | $R^{4a}$ | $R^{4b}$ | $R^5$ | $R^6$ |
|---|---|---|---|---|
| t-Bu | Br | I | Br | Br |
| Me | Br | CF$_3$ | CF$_3$ | Cl |
| Et | Br | CF$_3$ | CF$_3$ | Cl |
| i-Pr | Br | CF$_3$ | CF$_3$ | Cl |
| t-Bu | Br | CF$_3$ | CF$_3$ | Cl |
| Me | Br | CF$_3$ | CF$_3$ | Br |
| Et | Br | CF$_3$ | CF$_3$ | Br |
| i-Pr | Br | CF$_3$ | CF$_3$ | Br |
| t-Bu | Br | CF$_3$ | CF$_3$ | Br |
| Me | Br | CF$_3$ | Cl | Cl |
| Et | Br | CF$_3$ | Cl | Cl |
| i-Pr | Br | CF$_3$ | Cl | Cl |
| t-Bu | Br | CF$_3$ | Cl | Cl |
| Me | Br | CF$_3$ | Cl | Br |
| Et | Br | CF$_3$ | Cl | Br |
| i-Pr | Br | CF$_3$ | Cl | Br |
| t-Bu | Br | CF$_3$ | Cl | Br |
| Me | Br | CF$_3$ | Br | Cl |
| Et | Br | CF$_3$ | Br | Cl |
| i-Pr | Br | CF$_3$ | Br | Cl |
| t-Bu | Br | CF$_3$ | Br | Cl |
| Me | Br | CF$_3$ | Br | Br |
| Et | Br | CF$_3$ | Br | Br |
| i-Pr | Br | CF$_3$ | Br | Br |
| t-Bu | Br | CF$_3$ | Br | Br |
| Me | Br | Br | CF$_3$ | Cl |
| Et | Br | Br | CF$_3$ | Cl |
| i-Pr | Br | Br | CF$_3$ | Cl |
| t-Bu | Br | Br | CF$_3$ | Cl |
| Me | Br | Br | CF$_3$ | Br |
| Et | Br | Br | CF$_3$ | Br |
| i-Pr | Br | Br | CF$_3$ | Br |
| t-Bu | Br | Br | CF$_3$ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | CH$_3$ | CF$_3$ | Br | Cl |
| Et | CH$_3$ | CF$_3$ | Br | Cl |
| i-Pr | CH$_3$ | CF$_3$ | Br | Cl |
| t-Bu | CH$_3$ | CF$_3$ | Br | Cl |
| n-Pr | CH$_3$ | Cl | Cl | Cl |
| n-Bu | CH$_3$ | Cl | Cl | Cl |
| s-Bu | CH$_3$ | Cl | Cl | Cl |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF$_3$ | Cl |
| Et | Cl | H | CF$_3$ | Cl |
| i-Pr | Cl | H | CF$_3$ | Cl |
| t-Bu | Cl | H | CF$_3$ | Cl |

TABLE 20-continued

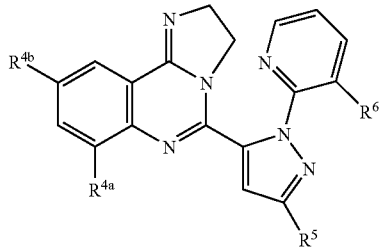

| R² | R⁴ᵃ | R⁴ᵇ | R⁵ | R⁶ |
|---|---|---|---|---|
| Me | Cl | H | CF₃ | Br |
| Et | Cl | H | CF₃ | Br |
| i-Pr | Cl | H | CF₃ | Br |
| t-Bu | Cl | H | CF₃ | Br |
| Me | Cl | H | Cl | Cl |
| Et | Cl | H | Cl | Cl |
| i-Pr | Cl | H | Cl | Cl |
| t-Bu | Cl | H | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| t-Bu | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF₃ | Cl |
| Et | Cl | I | CF₃ | Cl |
| i-Pr | Cl | I | CF₃ | Cl |
| t-Bu | Cl | I | CF₃ | Cl |
| Me | Cl | I | CF₃ | Br |
| Et | Cl | I | CF₃ | Br |
| i-Pr | Cl | I | CF₃ | Br |
| t-Bu | Cl | I | CF₃ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF₃ | CF₃ | Cl |
| Et | Cl | CF₃ | CF₃ | Cl |
| i-Pr | Cl | CF₃ | CF₃ | Cl |
| t-Bu | Cl | CF₃ | CF₃ | Cl |
| Me | Cl | CF₃ | CF₃ | Br |
| Et | Cl | CF₃ | CF₃ | Br |
| i-Pr | Cl | CF₃ | CF₃ | Br |
| t-Bu | Cl | CF₃ | CF₃ | Br |
| Me | Cl | CF₃ | Cl | Cl |
| Et | Cl | CF₃ | Cl | Cl |
| i-Pr | Cl | CF₃ | Cl | Cl |
| t-Bu | Cl | CF₃ | Cl | Cl |
| Me | Cl | CF₃ | Cl | Br |
| Et | Cl | CF₃ | Cl | Br |
| i-Pr | Cl | CF₃ | Cl | Br |
| t-Bu | Cl | CF₃ | Cl | Br |
| Me | Cl | CF₃ | Br | Cl |
| Et | Cl | CF₃ | Br | Cl |
| i-Pr | Cl | CF₃ | Br | Cl |
| t-Bu | Cl | CF₃ | Br | Cl |
| Me | Cl | CF₃ | Br | Br |
| Et | Cl | CF₃ | Br | Br |
| i-Pr | Cl | CF₃ | Br | Br |
| t-Bu | Cl | CF₃ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF₃ | Cl |
| Et | Br | F | CF₃ | Cl |
| i-Pr | Br | F | CF₃ | Cl |
| t-Bu | Br | F | CF₃ | Cl |
| Me | Br | F | CF₃ | Br |
| Et | Br | F | CF₃ | Br |
| i-Pr | Br | F | CF₃ | Br |
| t-Bu | Br | F | CF₃ | Br |
| Me | Br | F | Cl | Cl |
| Et | Br | F | Cl | Cl |
| i-Pr | Br | F | Cl | Cl |
| t-Bu | Br | F | Cl | Cl |
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| t-Bu | CH₃ | CF₃ | Br | Br |
| i-Bu | CH₃ | Cl | Cl | Cl |

TABLE 21

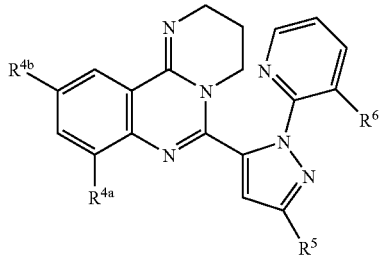

| R² | R⁴ᵃ | R⁴ᵇ | R⁵ | R⁶ |
|---|---|---|---|---|
| Me | CH₃ | H | CF₃ | Cl |
| Et | CH₃ | H | CF₃ | Cl |
| i-Pr | CH₃ | H | CF₃ | Cl |
| t-Bu | CH₃ | H | CF₃ | Cl |
| Me | CH₃ | H | CF₃ | Br |
| Et | CH₃ | H | CF₃ | Br |
| i-Pr | CH₃ | H | CF₃ | Br |
| t-Bu | CH₃ | H | CF₃ | Br |
| Me | CH₃ | H | Cl | Cl |
| Et | CH₃ | H | Cl | Cl |
| i-Pr | CH₃ | H | Cl | Cl |
| t-Bu | CH₃ | H | Cl | Cl |
| Me | CH₃ | H | Cl | Br |
| Et | CH₃ | H | Cl | Br |
| i-Pr | CH₃ | H | Cl | Br |
| t-Bu | CH₃ | H | Cl | Br |
| Me | CH₃ | H | Br | Cl |
| Et | CH₃ | H | Br | Cl |
| i-Pr | CH₃ | H | Br | Cl |
| t-Bu | CH₃ | H | Br | Cl |
| Me | CH₃ | H | Br | Br |
| Et | CH₃ | H | Br | Br |
| i-Pr | CH₃ | H | Br | Br |
| t-Bu | CH₃ | H | Br | Br |
| Me | CH₃ | F | CF₃ | Cl |
| Et | CH₃ | F | CF₃ | Cl |
| i-Pr | CH₃ | F | CF₃ | Cl |
| t-Bu | CH₃ | F | CF₃ | Cl |
| Me | CH₃ | F | CF₃ | Br |
| Et | CH₃ | F | CF₃ | Br |
| i-Pr | CH₃ | F | CF₃ | Br |
| t-Bu | CH₃ | F | CF₃ | Br |
| Me | CH₃ | F | Cl | Cl |
| Et | CH₃ | F | Cl | Cl |
| i-Pr | CH₃ | F | Cl | Cl |
| t-Bu | CH₃ | F | Cl | Cl |
| Me | CH₃ | F | Cl | Br |
| Et | CH₃ | F | Cl | Br |
| i-Pr | CH₃ | F | Cl | Br |
| t-Bu | CH₃ | F | Cl | Br |
| Me | CH₃ | F | Br | Cl |
| Et | CH₃ | F | Br | Cl |
| i-Pr | CH₃ | F | Br | Cl |
| t-Bu | CH₃ | F | Br | Cl |
| Me | CH₃ | F | Br | Br |
| Et | CH₃ | F | Br | Br |
| i-Pr | CH₃ | F | Br | Br |
| t-Bu | CH₃ | F | Br | Br |
| Me | CH₃ | Cl | CF₃ | Cl |
| Et | CH₃ | Cl | CF₃ | Cl |
| i-Pr | CH₃ | Cl | CF₃ | Cl |
| t-Bu | CH₃ | Cl | CF₃ | Cl |
| Me | CH₃ | Cl | CF₃ | Br |
| Et | CH₃ | Cl | CF₃ | Br |
| i-Pr | CH₃ | Cl | CF₃ | Br |
| t-Bu | CH₃ | Cl | CF₃ | Br |
| Me | CH₃ | Cl | Cl | Cl |
| Et | CH₃ | Cl | Cl | Cl |
| i-Pr | CH₃ | Cl | Cl | Cl |
| t-Bu | CH₃ | Cl | Cl | Cl |
| Me | CH₃ | Cl | Cl | Br |
| Et | CH₃ | Cl | Cl | Br |
| i-Pr | CH₃ | Cl | Cl | Br |
| t-Bu | CH₃ | Cl | Cl | Br |
| Me | CH₃ | Cl | Br | Cl |
| Et | CH₃ | Cl | Br | Cl |
| i-Pr | CH₃ | Cl | Br | Cl |
| t-Bu | CH₃ | Cl | Br | Cl |
| Me | CH₃ | Cl | Br | Br |
| Et | CH₃ | Cl | Br | Br |
| i-Pr | CH₃ | Cl | Br | Br |
| t-Bu | CH₃ | Cl | Br | Br |
| Me | CH₃ | Br | CF₃ | Cl |
| Et | CH₃ | Br | CF₃ | Cl |
| i-Pr | CH₃ | Br | CF₃ | Cl |
| t-Bu | CH₃ | Br | CF₃ | Cl |
| Me | CH₃ | Br | CF₃ | Br |
| Et | CH₃ | Br | CF₃ | Br |
| i-Pr | CH₃ | Br | CF₃ | Br |
| t-Bu | CH₃ | Br | CF₃ | Br |
| Me | CH₃ | Br | Cl | Cl |
| Et | CH₃ | Br | Cl | Cl |
| i-Pr | CH₃ | Br | Cl | Cl |
| t-Bu | CH₃ | Br | Cl | Cl |
| Me | CH₃ | Br | Cl | Br |
| Et | CH₃ | Br | Cl | Br |
| i-Pr | CH₃ | Br | Cl | Br |
| t-Bu | CH₃ | Br | Cl | Br |
| Me | CH₃ | Br | Br | Cl |
| Et | CH₃ | Br | Br | Cl |
| i-Pr | CH₃ | Br | Br | Cl |
| t-Bu | CH₃ | Br | Br | Cl |
| Me | CH₃ | Br | Br | Br |
| Et | CH₃ | Br | Br | Br |
| i-Pr | CH₃ | Br | Br | Br |
| t-Bu | CH₃ | Br | Br | Br |
| Me | CH₃ | I | CF₃ | Cl |
| Et | CH₃ | I | CF₃ | Cl |
| i-Pr | CH₃ | I | CF₃ | Cl |
| t-Bu | CH₃ | I | CF₃ | Cl |
| Me | CH₃ | I | CF₃ | Br |
| Et | CH₃ | I | CF₃ | Br |
| i-Pr | CH₃ | I | CF₃ | Br |
| t-Bu | CH₃ | I | CF₃ | Br |
| Me | CH₃ | I | Cl | Cl |
| Et | CH₃ | I | Cl | Cl |
| i-Pr | CH₃ | I | Cl | Cl |
| t-Bu | CH₃ | I | Cl | Cl |
| Me | CH₃ | I | Cl | Br |
| Et | CH₃ | I | Cl | Br |
| i-Pr | CH₃ | I | Cl | Br |
| t-Bu | CH₃ | I | Cl | Br |
| Me | CH₃ | I | Br | Cl |
| Et | CH₃ | I | Br | Cl |
| i-Pr | CH₃ | I | Br | Cl |
| t-Bu | CH₃ | I | Br | Cl |
| Me | CH₃ | I | Br | Br |
| Et | CH₃ | I | Br | Br |
| i-Pr | CH₃ | I | Br | Br |
| t-Bu | CH₃ | I | Br | Br |
| Me | CH₃ | CF₃ | CF₃ | Cl |
| Et | CH₃ | CF₃ | CF₃ | Cl |
| i-Pr | CH₃ | CF₃ | CF₃ | Cl |
| t-Bu | CH₃ | CF₃ | CF₃ | Cl |
| Me | CH₃ | CF₃ | CF₃ | Br |
| Et | CH₃ | CF₃ | CF₃ | Br |

TABLE 21-continued

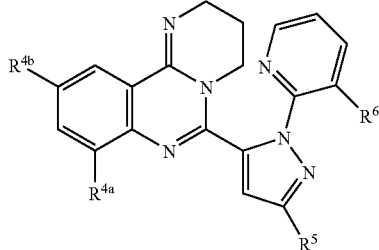

| R² | R⁴ᵃ | R⁴ᵇ | R⁵ | R⁶ |
|---|---|---|---|---|
| i-Pr | CH₃ | CF₃ | CF₃ | Br |
| t-Bu | CH₃ | CF₃ | CF₃ | Br |
| Me | CH₃ | CF₃ | Cl | Cl |
| Et | CH₃ | CF₃ | Cl | Cl |
| i-Pr | CH₃ | CF₃ | Cl | Cl |
| t-Bu | CH₃ | CF₃ | Cl | Cl |
| Me | CH₃ | CF₃ | Cl | Br |
| Et | CH₃ | CF₃ | Cl | Br |
| i-Pr | CH₃ | CF₃ | Cl | Br |
| t-Bu | CH₃ | CF₃ | Cl | Br |
| Me | CH₃ | CF₃ | Br | Br |
| Et | CH₃ | CF₃ | Br | Br |
| i-Pr | CH₃ | CF₃ | Br | Br |
| Me | Cl | F | CF₃ | Cl |
| Et | Cl | F | CF₃ | Cl |
| i-Pr | Cl | F | CF₃ | Cl |
| t-Bu | Cl | F | CF₃ | Cl |
| Me | Cl | F | CF₃ | Br |
| Et | Cl | F | CF₃ | Br |
| i-Pr | Cl | F | CF₃ | Br |
| t-Bu | Cl | F | CF₃ | Br |
| Me | Cl | F | Cl | Cl |
| Et | Cl | F | Cl | Cl |
| i-Pr | Cl | F | Cl | Cl |
| t-Bu | Cl | F | Cl | Cl |
| Me | Cl | F | Cl | Br |
| Et | Cl | F | Cl | Br |
| i-Pr | Cl | F | Cl | Br |
| t-Bu | Cl | F | Cl | Br |
| Me | Cl | F | Br | Cl |
| Et | Cl | F | Br | Cl |
| i-Pr | Cl | F | Br | Cl |
| t-Bu | Cl | F | Br | Cl |
| Me | Cl | F | Br | Br |
| Et | Cl | F | Br | Br |
| i-Pr | Cl | F | Br | Br |
| t-Bu | Cl | F | Br | Br |
| Me | Cl | Cl | CF₃ | Cl |
| Et | Cl | Cl | CF₃ | Cl |
| i-Pr | Cl | Cl | CF₃ | Cl |
| t-Bu | Cl | Cl | CF₃ | Cl |
| Me | Cl | Cl | CF₃ | Br |
| Et | Cl | Cl | CF₃ | Br |
| i-Pr | Cl | Cl | CF₃ | Br |
| t-Bu | Cl | Cl | CF₃ | Br |
| Me | Cl | Cl | Cl | Cl |
| Et | Cl | Cl | Cl | Cl |
| i-Pr | Cl | Cl | Cl | Cl |
| t-Bu | Cl | Cl | Cl | Cl |
| Me | Cl | Cl | Cl | Br |
| Et | Cl | Cl | Cl | Br |
| i-Pr | Cl | Cl | Cl | Br |
| t-Bu | Cl | Cl | Cl | Br |
| Me | Cl | Cl | Br | Cl |
| Et | Cl | Cl | Br | Cl |
| i-Pr | Cl | Cl | Br | Cl |
| t-Bu | Cl | Cl | Br | Cl |
| Me | Cl | Cl | Br | Br |
| Et | Cl | Cl | Br | Br |
| i-Pr | Cl | Cl | Br | Br |
| t-Bu | Cl | Cl | Br | Br |
| Me | Cl | Br | CF₃ | Cl |
| Et | Cl | Br | CF₃ | Cl |

TABLE 21-continued

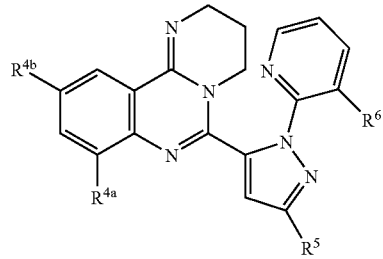

| R² | R⁴ᵃ | R⁴ᵇ | R⁵ | R⁶ |
|---|---|---|---|---|
| i-Pr | Cl | Br | CF₃ | Cl |
| t-Bu | Cl | Br | CF₃ | Cl |
| Me | Cl | Br | CF₃ | Br |
| Et | Cl | Br | CF₃ | Br |
| i-Pr | Cl | Br | CF₃ | Br |
| t-Bu | Cl | Br | CF₃ | Br |
| Me | Cl | Br | Cl | Cl |
| Et | Cl | Br | Cl | Cl |
| i-Pr | Cl | Br | Cl | Cl |
| t-Bu | Cl | Br | Cl | Cl |
| Me | Br | Br | Br | Cl |
| Et | Br | Br | Br | Cl |
| i-Pr | Br | Br | Br | Cl |
| t-Bu | Br | Br | Br | Cl |
| Me | Br | Br | Br | Br |
| Et | Br | Br | Br | Br |
| i-Pr | Br | Br | Br | Br |
| t-Bu | Br | Br | Br | Br |
| Me | Br | I | CF₃ | Cl |
| Et | Br | I | CF₃ | Cl |
| i-Pr | Br | I | CF₃ | Cl |
| t-Bu | Br | I | CF₃ | Cl |
| Me | Br | I | CF₃ | Br |
| Et | Br | I | CF₃ | Br |
| i-Pr | Br | I | CF₃ | Br |
| t-Bu | Br | I | CF₃ | Br |
| Me | Br | I | Cl | Cl |
| Et | Br | I | Cl | Cl |
| i-Pr | Br | I | Cl | Cl |
| t-Bu | Br | I | Cl | Cl |
| Me | Br | I | Cl | Br |
| Et | Br | I | Cl | Br |
| i-Pr | Br | I | Cl | Br |
| t-Bu | Br | I | Cl | Br |
| Me | Br | I | Br | Cl |
| Et | Br | I | Br | Cl |
| i-Pr | Br | I | Br | Cl |
| t-Bu | Br | I | Br | Cl |
| Me | Br | I | Br | Br |
| Et | Br | I | Br | Br |
| i-Pr | Br | I | Br | Br |
| t-Bu | Br | I | Br | Br |
| Me | Br | CF₃ | CF₃ | Cl |
| Et | Br | CF₃ | CF₃ | Cl |
| i-Pr | Br | CF₃ | CF₃ | Cl |
| t-Bu | Br | CF₃ | CF₃ | Cl |
| Me | Br | CF₃ | CF₃ | Br |
| Et | Br | CF₃ | CF₃ | Br |
| i-Pr | Br | CF₃ | CF₃ | Br |
| t-Bu | Br | CF₃ | CF₃ | Br |
| Me | Br | CF₃ | Cl | Cl |
| Et | Br | CF₃ | Cl | Cl |
| i-Pr | Br | CF₃ | Cl | Cl |
| t-Bu | Br | CF₃ | Cl | Cl |
| Me | Br | CF₃ | Cl | Br |
| Et | Br | CF₃ | Cl | Br |
| i-Pr | Br | CF₃ | Cl | Br |
| t-Bu | Br | CF₃ | Cl | Br |
| Me | Br | CF₃ | Br | Cl |
| Et | Br | CF₃ | Br | Cl |
| i-Pr | Br | CF₃ | Br | Cl |
| t-Bu | Br | CF₃ | Br | Cl |
| Me | Br | CF₃ | Br | Br |

TABLE 21-continued

| $R^2$ | $R^{4a}$ | $R^{4b}$ | $R^5$ | $R^6$ |
|---|---|---|---|---|
| Et | Br | CF$_3$ | Br | Br |
| i-Pr | Br | CF$_3$ | Br | Br |
| t-Bu | Br | CF$_3$ | Br | Br |
| Me | Br | Br | CF$_3$ | Cl |
| Et | Br | Br | CF$_3$ | Cl |
| i-Pr | Br | Br | CF$_3$ | Cl |
| t-Bu | Br | Br | CF$_3$ | Cl |
| Me | Br | Br | CF$_3$ | Br |
| Et | Br | Br | CF$_3$ | Br |
| i-Pr | Br | Br | CF$_3$ | Br |
| t-Bu | Br | Br | CF$_3$ | Br |
| Me | Br | Br | Cl | Cl |
| Et | Br | Br | Cl | Cl |
| i-Pr | Br | Br | Cl | Cl |
| t-Bu | Br | Br | Cl | Cl |
| Me | Br | Br | Cl | Br |
| Et | Br | Br | Cl | Br |
| i-Pr | Br | Br | Cl | Br |
| t-Bu | Br | Br | Cl | Br |
| Me | CH$_3$ | CF$_3$ | Br | Cl |
| Et | CH$_3$ | CF$_3$ | Br | Cl |
| i-Pr | CH$_3$ | CF$_3$ | Br | Cl |
| t-Bu | CH$_3$ | CF$_3$ | Br | Cl |
| n-Pr | CH$_3$ | Cl | Cl | Cl |
| n-Bu | CH$_3$ | Cl | Cl | Cl |
| s-Bu | CH$_3$ | Cl | Cl | Cl |
| Me | Cl | H | Cl | Br |
| Et | Cl | H | Cl | Br |
| i-Pr | Cl | H | Cl | Br |
| t-Bu | Cl | H | Cl | Br |
| Me | Cl | H | Br | Cl |
| Et | Cl | H | Br | Cl |
| i-Pr | Cl | H | Br | Cl |
| t-Bu | Cl | H | Br | Cl |
| Me | Cl | H | Br | Br |
| Et | Cl | H | Br | Br |
| i-Pr | Cl | H | Br | Br |
| t-Bu | Cl | H | Br | Br |
| Me | Cl | H | CF$_3$ | Cl |
| Et | Cl | H | CF$_3$ | Cl |
| i-Pr | Cl | H | CF$_3$ | Cl |
| t-Bu | Cl | H | CF$_3$ | Cl |
| Me | Cl | H | CF$_3$ | Br |
| Et | Cl | H | CF$_3$ | Br |
| i-Pr | Cl | H | CF$_3$ | Br |
| t-Bu | Cl | H | CF$_3$ | Br |
| Me | Cl | H | Cl | Cl |
| Et | Cl | H | Cl | Cl |
| i-Pr | Cl | H | Cl | Cl |
| t-Bu | Cl | H | Cl | Cl |
| Me | Cl | Br | Cl | Br |
| Et | Cl | Br | Cl | Br |
| i-Pr | Cl | Br | Cl | Br |
| t-Bu | Cl | Br | Cl | Br |
| Me | Cl | Br | Br | Cl |
| Et | Cl | Br | Br | Cl |
| i-Pr | Cl | Br | Br | Cl |
| t-Bu | Cl | Br | Br | Cl |
| Me | Cl | Br | Br | Br |
| Et | Cl | Br | Br | Br |
| i-Pr | Cl | Br | Br | Br |
| t-Bu | Cl | Br | Br | Br |
| Me | Cl | I | CF$_3$ | Cl |
| Et | Cl | I | CF$_3$ | Cl |
| i-Pr | Cl | I | CF$_3$ | Cl |
| t-Bu | Cl | I | CF$_3$ | Cl |
| Me | Cl | I | CF$_3$ | Br |
| Et | Cl | I | CF$_3$ | Br |
| i-Pr | Cl | I | CF$_3$ | Br |
| t-Bu | Cl | I | CF$_3$ | Br |
| Me | Cl | I | Cl | Cl |
| Et | Cl | I | Cl | Cl |
| i-Pr | Cl | I | Cl | Cl |
| t-Bu | Cl | I | Cl | Cl |
| Me | Cl | I | Cl | Br |
| Et | Cl | I | Cl | Br |
| i-Pr | Cl | I | Cl | Br |
| t-Bu | Cl | I | Cl | Br |
| Me | Cl | I | Br | Cl |
| Et | Cl | I | Br | Cl |
| i-Pr | Cl | I | Br | Cl |
| t-Bu | Cl | I | Br | Cl |
| Me | Cl | I | Br | Br |
| Et | Cl | I | Br | Br |
| i-Pr | Cl | I | Br | Br |
| t-Bu | Cl | I | Br | Br |
| Me | Cl | CF$_3$ | CF$_3$ | Cl |
| Et | Cl | CF$_3$ | CF$_3$ | Cl |
| i-Pr | Cl | CF$_3$ | CF$_3$ | Cl |
| t-Bu | Cl | CF$_3$ | CF$_3$ | Cl |
| Me | Cl | CF$_3$ | CF$_3$ | Br |
| Et | Cl | CF$_3$ | CF$_3$ | Br |
| i-Pr | Cl | CF$_3$ | CF$_3$ | Br |
| t-Bu | Cl | CF$_3$ | CF$_3$ | Br |
| Me | Cl | CF$_3$ | Cl | Cl |
| Et | Cl | CF$_3$ | Cl | Cl |
| i-Pr | Cl | CF$_3$ | Cl | Cl |
| t-Bu | Cl | CF$_3$ | Cl | Cl |
| Me | Cl | CF$_3$ | Cl | Br |
| Et | Cl | CF$_3$ | Cl | Br |
| i-Pr | Cl | CF$_3$ | Cl | Br |
| t-Bu | Cl | CF$_3$ | Cl | Br |
| Me | Cl | CF$_3$ | Br | Cl |
| Et | Cl | CF$_3$ | Br | Cl |
| i-Pr | Cl | CF$_3$ | Br | Cl |
| t-Bu | Cl | CF$_3$ | Br | Cl |
| Me | Cl | CF$_3$ | Br | Br |
| Et | Cl | CF$_3$ | Br | Br |
| i-Pr | Cl | CF$_3$ | Br | Br |
| t-Bu | Cl | CF$_3$ | Br | Br |
| n-Pr | Cl | Cl | Cl | Cl |
| n-Bu | Cl | Cl | Cl | Cl |
| s-Bu | Cl | Cl | Cl | Cl |
| i-Bu | Cl | Cl | Cl | Cl |
| Me | Br | F | CF$_3$ | Cl |
| Et | Br | F | CF$_3$ | Cl |
| i-Pr | Br | F | CF$_3$ | Cl |
| t-Bu | Br | F | CF$_3$ | Cl |
| Me | Br | F | CF$_3$ | Br |
| Et | Br | F | CF$_3$ | Br |
| i-Pr | Br | F | CF$_3$ | Br |
| t-Bu | Br | F | CF$_3$ | Br |
| Me | Br | F | Cl | Cl |
| Et | Br | F | Cl | Cl |
| i-Pr | Br | F | Cl | Cl |
| t-Bu | Br | F | Cl | Cl |

TABLE 21-continued

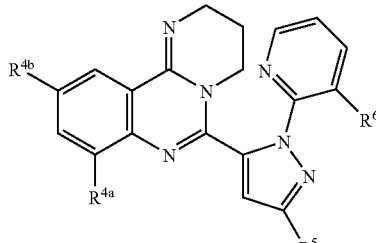

| R² | R⁴ᵃ | R⁴ᵇ | R⁵ | R⁶ |
|---|---|---|---|---|
| Me | Br | F | Cl | Br |
| Et | Br | F | Cl | Br |
| i-Pr | Br | F | Cl | Br |
| t-Bu | Br | F | Cl | Br |
| Me | Br | F | Br | Cl |
| Et | Br | F | Br | Cl |
| i-Pr | Br | F | Br | Cl |
| t-Bu | Br | F | Br | Cl |
| Me | Br | F | Br | Br |
| Et | Br | F | Br | Br |
| i-Pr | Br | F | Br | Br |
| t-Bu | Br | F | Br | Br |
| Me | Br | Cl | CF₃ | Cl |
| Et | Br | Cl | CF₃ | Cl |
| i-Pr | Br | Cl | CF₃ | Cl |
| t-Bu | Br | Cl | CF₃ | Cl |
| Me | Br | Cl | CF₃ | Br |
| Et | Br | Cl | CF₃ | Br |
| i-Pr | Br | Cl | CF₃ | Br |
| t-Bu | Br | Cl | CF₃ | Br |
| Me | Br | Cl | Cl | Cl |
| Et | Br | Cl | Cl | Cl |
| i-Pr | Br | Cl | Cl | Cl |
| t-Bu | Br | Cl | Cl | Cl |
| Me | Br | Cl | Cl | Br |
| Et | Br | Cl | Cl | Br |
| i-Pr | Br | Cl | Cl | Br |
| t-Bu | Br | Cl | Cl | Br |
| Me | Br | Cl | Br | Cl |
| Et | Br | Cl | Br | Cl |
| i-Pr | Br | Cl | Br | Cl |
| t-Bu | Br | Cl | Br | Cl |
| Me | Br | Cl | Br | Br |
| Et | Br | Cl | Br | Br |
| i-Pr | Br | Cl | Br | Br |
| t-Bu | Br | Cl | Br | Br |
| t-Bu | CH₃ | CF₃ | Br | Br |
| i-Bu | CH₃ | Cl | Cl | Cl |

Formulation/Utility

Compounds used in accordance with this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)-encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid-diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene-block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th-Ed., Blackwell Scientific Publications, Oxford, 1989.

In the following Examples, all percentages are by weight and all formulations are prepared in conventional ways. Compound numbers refer to compounds in Index Table A.

EXAMPLE A

| Wettable Powder | |
|---|---|
| Compound 4 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
|---|---|
| Compound 4 | 10.0% |
| attapulgite granules (low volatile matter, 0.71/0.30 mm; U.S.S. No. 25-50 sieves) | 90.0%. |

EXAMPLE C

| Extruded Pellet | |
|---|---|
| Compound 4 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

| Emulsifiable Concentrate | |
|---|---|
| Compound 4 | 20.0% |
| blend of oil soluble sulfonates and polyoxyethylene ethers | 10.0% |
| isophorone | 70.0%. |

EXAMPLE E

| Granule | |
|---|---|
| Compound 4 | 0.5% |
| cellulose | 2.5% |
| lactose | 4.0% |
| cornmeal | 93.0%. |

Compounds used in accordance with this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds used in accordance with this invention display activity against economically important agronomic and nonagronomic pests. The term "agronomic" refers to the production of field crops such as for food and fiber and includes the growth of cereal crops (e.g., wheat, oats, barley, lye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectino-

*phora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brown-banded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adult, of the order Coleoptera including weevils from the families Anthribidae, Bruchidae, and Curculionidae (e.g., boll weevil (*Anthonomus grandis* Boheman), rice water weevil (*Lissorhoptris oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cincticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds used in accordance with this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent Examples of such biologically active compounds or agents with which compounds used in accordance with this invention can be formulated are: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), myclobutanil, neo-asozin (ferric methanearsonate), oxadixyl, penconazole, pencycuron, probenazole, prochloraz, proparmocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitaz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Compounds used in accordance with this invention and compositions thereof may be applied to plants genetically transformed to express proteins toxic to invertebrate pests (such as *Bacillus thuringiensis* toxin). The effect of the exogenous invertebrate pest control compounds and compositions may be synergistic with the expressed toxin proteins.

A general reference for these agricultural protectants is *The Pesticide Manual, 12th Edition,* C. D. S. Tomlin, Ed., British Crop Protection Council, Farnham, Surrey, U.K., 2000.

Preferred insecticides and acaricides for mixing with compounds used in accordance with this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds used in accordance with this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound used in accordance with this invention with cyhalothrin; a mixture of a compound used in accordance with this invention with beta-cyfluthrin; a mixture of a compound used in accordance with this invention with esfenvalerate; a mixture of a compound used in accordance with this invention with methomyl; a mixture of a compound used in accordance with this invention with imidacloprid; a mixture of a compound used in accordance with this invention with thiacloprid; a mixture of a compound used in accordance with this invention with indoxacarb; a mixture of a compound used in accordance with this invention with abamectin; a mixture of a compound used in accordance with this invention with endosulfan; a mixture of a compound used in accordance with this invention with ethiprole; a mixture of a compound used in accordance with this invention with fipronil; a mixture of a compound used in accordance with this invention with flufenoxuron; a mixture of a compound used in accordance with this invention with pyriproxyfen; a mixture of a compound used in accordance with this invention with pymetrozine; a mixture of a compound used in accordance with this invention with amitraz; a mixture of a compound used in accordance with this invention with *Bacillus thuringiensis* and a mixture of a compound used in accordance with this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds used in accordance with this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound is present on the same granule as the compound of the invention or on granules separate from those of the compound used in accordance with this invention.

A preferred method of contact is by spraying. Alternatively, a granular composition comprising a compound of the invention can be applied to the plant foliage or the soil. Compounds used in accordance with this invention are also effectively delivered through plant uptake by contacting the plant with a composition comprising a compound used in accordance with this invention applied as a soil drench of a liquid formulation, a granular formulation to the soil, a nursery box treatment or a dip of transplants. Compounds are also effective by topical application of a composition comprising a compound used in accordance with this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds used in accordance with this invention may also be impregnated into materials for fabricating invertebrate control devices (e.g. insect netting).

The compounds used in accordance with this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds used in accordance with this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following Tests in the Biological Examples of the Invention demonstrate the efficacy of methods of the invention for protecting plants from specific invertebrate pests. "Control efficacy" represents inhibition of invertebrate development (including mortality) that causes significantly reduced feeding. The pest control protection afforded by the compounds is not limited, however, to these species. See Index Tables A through D for compound descriptions. The following abbreviations are used in the Index Tables that follow: i is iso, Me is methyl, Ph is phenyl and Pr is propyl (accordingly i-Pr is isopropyl). In Index Tables B and C, the moiety $R^1$-$R^2$ is listed such that the left end of the moiety is attached at the $R^1$ location and the right end of the moiety is attached at the $R^2$ location. The abbreviation "Ex." stands for "Example" and is followed by a number indicating in which example the compound is prepared.

INDEX TABLE A

| Compound | $R^{4b}$ | $R^2$ | $R^5$ | V | m.p. (° C) |
|---|---|---|---|---|---|
| 1 | H | CH(Me)CH$_3$Cl | CF$_3$ | CH | 129-131 |
| 2 (Ex. 2) | H | i-Pr | CF$_3$ | CH | 133-135 |
| 3 | H | Me | CF$_3$ | CH | 158-163 |
| 4 (Ex. 1) | H | i-Pr | CF$_3$ | N | 175-176 |
| 5 | Br | i-Pr | CF$_3$ | N | 173-174 |
| 6 | Br | propargyl | CF$_3$ | N | 187-190 |
| 7 | Cl | i-Pr | Br | N | 207-209 |
| 8 | Cl | Me | Br | N | 234-236 |
| 9 | Cl | i-Pr | CF$_3$ | N | 165-166 |
| 10 | Cl | Me | CF$_3$ | N | 181-182 |
| 11 | Cl | i-Pr | Cl | N | 182-183 |
| 12 | Cl | i-Pr | Br | N | 174-175 |

INDEX TABLE B

| Compound | $R^{4a}$ | $R^{4b}$ | $R^1$-$R^2$ | $R^5$ | V | m.p. (° C) |
|---|---|---|---|---|---|---|
| 13 (Ex. 3) | Cl | Cl | —CH$_2$CH$_2$— | CF$_3$ | N | * |
| 14 | Cl | Cl | —CH$_2$CH$_2$C(=O)— | CF$_3$ | N | * |
| 15 | Cl | Cl | —CH=C(CH$_3$)— | CF$_3$ | N | * |
| 16 | Cl | Cl | —C(CH$_3$)=CH— | CF$_3$ | N | * |

*See Index Table D for $^1$H NMR Data

INDEX TABLE C

| Compound | $R^{4a}$ | $R^{4b}$ | $R^1$-$R^2$ | J | m.p. (° C) |
|---|---|---|---|---|---|
| 17 | H | H | —CH$_2$CH$_2$— | 2,4-Cl$_2$—Ph | |
| 18 | H | H | —CH=N— | 3-Me—Ph | |
| 19 | H | H | —CH=N— | 4-Cl—Ph | |

INDEX TABLE D

| Compd. No. | ¹H NMR Data (CDCl₃ solution unless indicated otherwise)[a] |
|---|---|
| 13 | δ 8.4(d, 1H), 7.9(m, 2H), 7.45(d, 1H), 7.4(dd, 1H), 7.1(s, 1H), 4.4(m, 2H), 4.3-4.2(m, 2H). |
| 14 | δ 8.5-8.4(d, 1H), 8.4-8.3(dd, 1H), 8.0-7.9(dd, 1H), 7.6-7.5(d, 1H), 7.4(m, 2H), 7.09(s, 1H), 4.52(t, 2H), 2.78(t, 2H), 2.13(s, 3H). |
| 15 | δ 8.41(d, 1H), 8.39(dd, 1H), 7.90(dd, 1H), 7.81(q, 1H), 7.59(d, 1H), 7.46(s, 1H), 7.41(dd, 1H), 2.57(d, 3H). |
| 16 | δ 8.42(d, 1H), 8.09(dd, 1H), 7.90(dd, 1H), 7.62(d, 1H), 7.46(m, 1H), 7.27(dd, 1H), 7.05(s, 1H), 2.33(d, 3H). |

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on apiece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm (or less) and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided very good levels of plant protection (20% or less feeding damage) at the rates tested: 1*, 2*, 3*, 4*, 5*, 6*, 7, 8, 9, 10, 11, 12, 13**, 14.

Test B

For evaluating control of fall armyworm (*Spodoptera frugiperda*) the test unit consisted of a small open container with a 4-5-day-old corn (maize) plant inside. This was pre-infested with 10-15 1-day-old larvae on a piece of insect diet by use of a core sampler as described for Test A.

Test compounds were formulated and sprayed at 250 ppm (or less) as described for Test A. The applications were replicated three times. After spraying, the test units were maintained in a growth chamber and then visually rated as described for Test A.

Of the compounds tested, the following provided very good levels of plant protection (20% or less feeding damage) at the rates tested: 1*, 2*, 3*, 4*, 5*, 6*, 7, 8, 9, 10, 11, 12, 13.

Test C

For evaluating control of tobacco budworm (*Heliothis virescens*) the test unit consisted of a small open container with a 6-7 day old cotton plant inside. This was pre-infested with 8 2-day-old larvae on a piece of insect diet by use of a core sampler as described for Test A.

Test compounds were formulated and sprayed at 250 ppm (or less) as described for Test A. The applications were replicated three times. After spraying, the test units were maintained in a growth chamber and then visually rated as described for Test A.

Of the compounds tested, the following provided very good levels of plant protection (20% or less feeding damage) at the rates tested: 1*, 2*, 3*, 4*, 5*, 6*, 7, 8, 9, 10, 11, 12.

Test D

For evaluating control of beet armyworm (*Spodoptera exigua*) the test unit consisted of a small open container with a 45-day-old corn (maize) plant inside. This was pre-infested with 10-15 1-day-old larvae on a piece of insect diet by use of a core sampler as described for Test A.

Test compounds were formulated and sprayed at 250 ppm (or less) as described for Test A. The applications were replicated three times. After spraying, the test units were maintained in a growth chamber and then visually rated as described for Test A.

Of the compounds tested, the following provided very good levels of plant protection (20% or less feeding damage) at the rates tested: 1*, 2*, 3*, 4*, 5*, 6*, 7, 8, 9, 10, 11, 12.

* Tested at 50 ppm; ** Tested at 10 ppm.

What is claimed is:

1. A method for controlling an invertebrate pest comprising contacting the invertebrate pest or its environment with a biologically effective amount of a compound of Formula Is or an N-oxide or an agriculturally suitable salt thereof

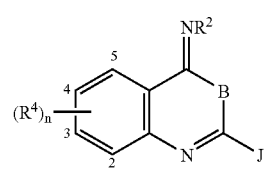

wherein
B is O;
J is selected from the group consisting of J-6, J-7, J-8, J-9, J-10, J-11, J-12 and J-13

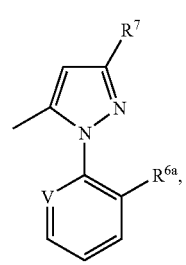

-continued

J-7 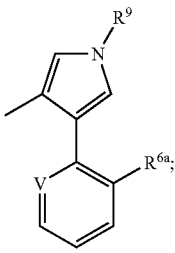

J-8 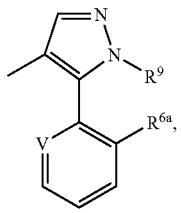

J-9 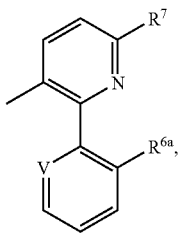

J-10 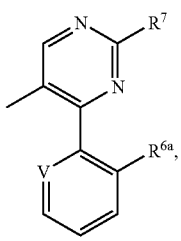

J-11 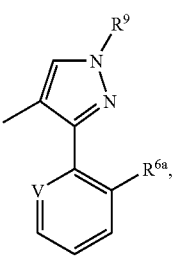

J-12 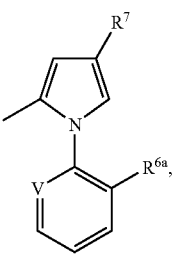

J-13 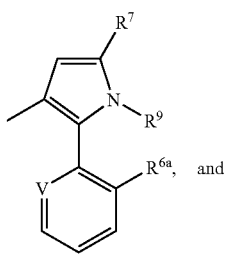

V is N, CH, CF, CCl, CBr or CI;

$R^2$ is H; G; $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of halogen, G, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, and a phenyl, phenoxy or 5- or 6-membered heteroaromatic ring, each ring optionally substituted with one to three substituents independently selected from $R^6$; hydroxy; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl and $C_2$-$C_6$ alkylcarbonyl;

G is a 5- or 6-membered nonaromatic carbocyclic or heterocyclic ring, optionally including one or two ring members selected from the group consisting of C(=O), SO and S(O)$_2$ and optionally substituted with 1 to 4 substituents selected from $R^3$;

each $R^3$ is independently $C_1$-$C_2$ alkyl, halogen, CN, $NO_2$ or $C_1$-$C_2$ alkoxy;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_5$ alkoxyalkyl, $C_1$-$C_4$ hydroxyalkyl, C(O)$R^{10}$, CO$_2R^{10}$, C(O)NR$^{10}$R$^{11}$, NR$^{10}$R$^{11}$, N(R$^{11}$)CO$_2$R$^{10}$ or $C_3$-$C_6$ trialkylsilyl; or each $R^4$ is independently a phenyl, benzyl, phenoxy or a 5- or 6-membered heteroaromatic ring, each ring optionally substituted with one to three substituents independently selected from $R^6$;

$R^6$ is $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ haloalkoxy or $C_1$-$C_4$ haloalkylthio;

each $R^{6a}$ is independently H or $R^6$;

each $R^7$ is independently $C_1$-$C_6$ alkyl, $C_1$-$C_6$ haloalkyl, halogen, CN, $C_1$-$C_4$ alkoxy, $C_1$-$C_4$ haloalkoxy or $C_1$-$C_4$ haloalkylthio;

$R^9$ is $C_2$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl;

$R^{10}$ is $C_1$-$C_4$ alkyl or $C_1$-$C_4$ haloalkyl;

$R^{11}$ is $C_1$-$C_4$ alkyl; and n is 1 or 2.

2. The method of claim 1 wherein $R^2$ is $C_1$-$C_4$ alkyl optionally substituted with halogen, CN, OHC$_3$ or S(O)$_p$CH$_3$; or CH$_2$C≡CH;

one R⁴ group is attached to the phenyl ring at the 2-position and said R⁴ is $CH_3$, $CF_3$, $OCF_3$, $OCHF_2$, $S(O)_p CF_3$, $S(O)_p CHF_2$, CN or halogen;
a second R⁴ is H, F, Cl, Br, I, CN or $CF_3$;
$R^{6a}$ is H, $C_1$-$C_4$ alkyl, $C_1$-$C_4$ haloalkyl, halogen or CN;
$R^7$ is $CH_3$, $CF_3$, $OCH_2CF_3$, $OCHF_2$ or halogen;
$R^9$ is $C_2$-$C_6$alkyl or $C_1$-$C_6$haloalkyl; and
p is 0, 1 or 2.

3. The method of claim 2 wherein J substituted with 1 to 3 $R^5$ is J-6; V is N or CH; and $R^7$ is $CH_3$, $CF_3$, $OCH_2CF_3$, $OCHF_2$ or halogen.

4. The method of claim 3 wherein $R^{6a}$ is F, Cl or Br; and $R^7$ is halogen or $CF_3$.

5. The method of claim 2 wherein J substituted with 1 to 3 $R^5$ is J-7.

6. The method of claim 2 wherein J substituted with 1 to 3 $R^5$ is J-8; V is N; $R^{6a}$ is Cl or Br; and $R^7$ is halogen or $CF_3$.

7. The method of claim 2 wherein J substituted with 1 to 3 $R^5$ is J-9; $R^{6a}$ is Cl or Br; and $R^7$ is $CF_3$.

8. The method of claim 2 wherein J substituted with 1 to 3 $R^5$ is J-10; $R^{6a}$ is Cl or Br; and $R^9$ is $CH_2CF_3$, $CHF_2$ or $CF_3$.

9. The method of claim 2 wherein J substituted with 1 to 3 $R^5$ is J-11; $R^{6a}$ is Cl or Br; and $R^7$ is halogen, $OCH_2CF_3$, $OCHF_2$ or $CF_3$.

10. The method of claim 2 wherein J substituted with 1 to 3 $R^5$ is J-12; $R^{6a}$ is Cl or Br; $R^7$ is halogen, $OCH_2CF_3$, $OCHF_2$ or $CF_3$; and $R^9$ is $CH_2CF_3$, $CHF_2$ or $CF_3$.

11. The method of claim 2 wherein J substituted with 1 to 3 $R^5$ is J-13; $R^{6a}$ is Cl or Br; and $R^9$ is $CH_2CF_3$, $CHF_2$ or $CF_3$.

12. The method of claim 3 comprising a compound selected from the group consisting of:
N-[2-[3-bromo-1-(3-chloro-2-pyridinyl)-1H-pyrazol-5-yl]-6-chloro-8-methyl-4H-3,1-benzoxazin-4-ylidene]methanamine,
N-[2-[3-bromo-1-(3-chloro-2-pyridinyl)-1H-pyrazol-5-yl]-6-chloro-8-methyl-4H-3,1-benzoxazin-4-ylidene]-2-propanamine,
N-[2-[3-bromo-1-(3-chloro-2-pyridinyl)-1H-pyrazol-5-yl]-6-chloro-8-methyl-4H-3,1-benzoxazin-4-ylidene]ethanamine,
N-[6-chloro-2-[3-chloro-1-(3-chloro-2-pyridinyl)-1H-pyrazol-5-yl]-8-methyl-4H-3,1-benzoxazin-4-ylidene]methanamine,
N-[6-chloro-2-[3-chloro-1-(3-chloro-2-pyridinyl)-1H-pyrazol-5-yl]-8-methyl-4H-3,1-benzoxazin-4-ylidene]-2-propanamine,
N-[6-chloro-2-[3-chloro-1-(3-chloro-2-pyridinyl)-1H-pyrazol-5-yl]-8-methyl-4H-3,1-benzoxazin-4-ylidene]ethanamine,
N-[6-chloro-2-[1-(3-chloro-2-pyridinyl)-3-(trifluoromethyl)-1H-pyrazol-5-yl]-8-methyl-4H-3,1-benzoxazin-4-ylidene]methanamine,
N-[6-chloro-2-[1-(3-chloro-2-pyridinyl)-3-(trifluoromethyl)-1H-pyrazol-5-yl]-8-methyl-4H-3,1-benzoxazin-4-ylidene]-2-propanamine,
N-[6-chloro-2-[1-(3-chloro-2-pyridinyl)-3-(trifluoromethyl)-1H-pyrazol-5-yl]-8-methyl-4H-3,1-benzoxazin-4-ylidene]ethanamine,
N-[6-chloro-2-[1-(3-chloro-2-pyridinyl)-3-(trifluoromethyl-1H-pyrazol-5-yl]-8-methyl-4H-3,1-benzoxazin-4-ylidene]-2-methyl-2-propanamine,
N-[2-[3-bromo-1-(3-chloro-2-pyridinyl)-1H-pyrazol-S-yl]-8-methyl-4H-3,1-benzoxazin-4-ylidene]-2-propanamine,
N-[2-[3-bromo-1-(3-chloro-2-pyridinyl)-1H-pyrazol-5-yl]-8-methyl-4H-3,1-benzoxazin-4-ylidene]-2-methyl-2-propanamine,
N-[2-[1-(3-chloro-2-pyridinyl)-3-(trifluoromethyl)-1H-pyrazol-5-yl]-8-methyl-4H-3,1-benzoxazin-4-ylidene]-2-propanamine and
N-[2-[1-(3-chloro-2-pyridinyl)-3-(trifluoromethyl)-1H-pyrazol-5-yl]-8-methyl-4H-3,1-benzoxazin-4-ylidene]-2-methyl-2-propanamine.

13. The method of claim 1 wherein the compound of Formula Is is comprised in a composition, said composition optionally further comprising an effective amount of at least one additional biologically active compound or agent.

* * * * *

UNITED STATES PATENT AND TRADEMARK OFFICE
CERTIFICATE OF CORRECTION

PATENT NO. : 7,326,704 B2
APPLICATION NO. : 11/490898
DATED : February 5, 2008
INVENTOR(S) : Thomas Paul Selby It is certified that error appears in the above-identified patent and that said Letters Patent is hereby corrected as shown below:

Column 188, line 67, "OHC$_3$" should read -- OCH$_3$ --.

Column 190, line 24, "-1H-pyrazol-S-" should read -- -1H-pyrazole-5- --.

Signed and Sealed this

Twenty-fourth Day of June, 2008

JON W. DUDAS
*Director of the United States Patent and Trademark Office*